(12) United States Patent
Barlow et al.

(10) Patent No.: US 7,985,756 B2
(45) Date of Patent: Jul. 26, 2011

(54) MODULATION OF NEUROGENESIS BY PDE INHIBITION

(75) Inventors: Carrolee Barlow, Del Mar, CA (US); Todd A. Carter, San Diego, CA (US); Kym I. Lorrain, San Diego, CA (US); Jammieson C. Pires, San Diego, CA (US); Kai Treuner, San Diego, CA (US)

(73) Assignee: BrainCells Inc., San Diego, CA (US)

( * ) Notice: Subject to any disclaimer, the term of this patent is extended or adjusted under 35 U.S.C. 154(b) by 925 days.

(21) Appl. No.: 11/551,667

(22) Filed: Oct. 20, 2006

(65) Prior Publication Data

US 2007/0208029 A1 Sep. 6, 2007

Related U.S. Application Data

(60) Provisional application No. 60/729,366, filed on Oct. 21, 2005, provisional application No. 60/784,605, filed on Mar. 21, 2006, provisional application No. 60/807,594, filed on Jul. 17, 2006.

(51) Int. Cl.
*A61K 31/505* (2006.01)
*A61K 31/40* (2006.01)
*A61K 31/44* (2006.01)
*A61K 31/445* (2006.01)

(52) U.S. Cl. ......... 514/275; 514/315; 514/354; 514/424

(58) Field of Classification Search ........................ None
See application file for complete search history.

(56) References Cited

U.S. PATENT DOCUMENTS

| | | |
|---|---|---|
| 3,819,631 A | 6/1974 | Marshall et al. |
| 3,932,407 A | 1/1976 | Beverung, Jr. et al. |
| 3,941,785 A | 3/1976 | Clarke et al. |
| 4,036,840 A | 7/1977 | O'Brien et al. |
| 4,051,236 A | 9/1977 | Harris et al. |
| 4,093,617 A | 6/1978 | Robins et al. |
| 4,096,257 A | 6/1978 | Menschik et al. |
| 4,107,307 A | 8/1978 | Paul et al. |
| 4,107,309 A | 8/1978 | Paul et al. |
| 4,123,534 A | 10/1978 | Credner et al. |
| 4,146,718 A | 3/1979 | Jenks et al. |
| 4,188,391 A | 2/1980 | Campbell et al. |
| RE30,511 E | 2/1981 | Paul et al. |
| 4,298,734 A | 11/1981 | Temple, Jr. |
| 4,298,772 A | 11/1981 | Kobayashi et al. |
| 4,366,156 A | 12/1982 | Temple, Jr. |
| 4,370,328 A | 1/1983 | Campbell et al. |
| 4,404,380 A | 9/1983 | Temple, Jr. |
| RE31,617 E | 6/1984 | Beverung, Jr. et al. |
| 4,460,765 A | 7/1984 | Naito et al. |
| 4,489,078 A | 12/1984 | Temple, Jr. |
| 4,490,371 A | 12/1984 | Jones et al. |
| 4,564,619 A | 1/1986 | Tanaka et al. |
| 4,593,029 A | 6/1986 | Venuti et al. |
| 4,642,345 A | 2/1987 | Temple, Jr. |
| 4,663,320 A | 5/1987 | Jones et al. |
| 4,670,434 A | 6/1987 | Venuti |
| 4,701,459 A | 10/1987 | Meanwell et al. |
| 4,721,784 A | 1/1988 | Combs |
| 4,739,056 A | 4/1988 | Venuti |
| 4,761,416 A | 8/1988 | Fried et al. |
| 4,775,674 A | 10/1988 | Meanwell et al. |
| 4,776,118 A | 10/1988 | Mizuno |
| 4,861,891 A | 8/1989 | Saccomano et al. |
| 4,906,628 A | 3/1990 | Coates |
| 4,943,573 A | 7/1990 | Meanwell |
| 4,963,561 A | 10/1990 | Lesher et al. |
| 4,971,972 A | 11/1990 | Doll et al. |
| 5,010,086 A | 4/1991 | Lesher et al. |
| 5,066,653 A | 11/1991 | Coates |
| 5,081,242 A | 1/1992 | Combs |
| 5,091,431 A | 2/1992 | Tulshian et al. |
| 5,116,837 A | 5/1992 | Combs |
| 5,250,534 A | 10/1993 | Bell et al. |
| 5,294,612 A | 3/1994 | Bacon et al. |
| 5,340,827 A | 8/1994 | Beeley et al. |
| 5,346,901 A | 9/1994 | Bell et al. |
| 5,488,055 A | 1/1996 | Kumar et al. |
| 5,491,147 A | 2/1996 | Boyd et al. |
| 5,502,072 A | 3/1996 | Masamune |
| 5,521,187 A | 5/1996 | Freyne et al. |
| 5,550,137 A | 8/1996 | Beeley et al. |
| 5,580,888 A | 12/1996 | Warrellow et al. |
| 5,608,070 A | 3/1997 | Alexander et al. |

(Continued)

FOREIGN PATENT DOCUMENTS

EP 579496 A1 1/1994

(Continued)

OTHER PUBLICATIONS

Kato et al., European Journal of Pharmacology, 1995, vol. 272, pp. 107-110.*

(Continued)

*Primary Examiner* — James Anderson
*Assistant Examiner* — Gregg Polansky
(74) *Attorney, Agent, or Firm* — Sughrue Mion, PLLC

(57) ABSTRACT

The instant disclosure describes methods for treating diseases and conditions of the central and peripheral nervous system by stimulating or increasing neurogenesis. The disclosure includes compositions and methods based on use of a PDE agent, optionally in combination with one or more other neurogenic agents, to stimulate or activate the formation of new nerve cells.

2 Claims, 6 Drawing Sheets

U.S. PATENT DOCUMENTS

| | | | |
|---|---|---|---|
| 5,622,977 A | 4/1997 | Warrellow et al. |
| 5,633,257 A | 5/1997 | Warrellow et al. |
| 5,665,754 A | 9/1997 | Feldman et al. |
| 5,674,880 A | 10/1997 | Boyd et al. |
| 5,686,434 A | 11/1997 | Kleinman |
| 5,693,659 A | 12/1997 | Head et al. |
| 5,710,160 A | 1/1998 | Guay et al. |
| 5,710,170 A | 1/1998 | Guay et al. |
| 5,712,298 A | 1/1998 | Amschler |
| 5,716,967 A | 2/1998 | Kleinman |
| 5,719,283 A | 2/1998 | Bell et al. |
| 5,723,460 A | 3/1998 | Warrellow et al. |
| 5,739,144 A | 4/1998 | Warrellow et al. |
| 5,776,958 A | 7/1998 | Warrellow et al. |
| 5,780,477 A | 7/1998 | Head et al. |
| 5,780,478 A | 7/1998 | Alexander et al. |
| 5,786,354 A | 7/1998 | Warrellow et al. |
| 5,798,373 A | 8/1998 | Warrellow |
| 5,814,651 A | 9/1998 | Duplantier et al. |
| 5,817,670 A | 10/1998 | Takayama et al. |
| 5,849,770 A | 12/1998 | Head et al. |
| 5,859,006 A | 1/1999 | Daugan |
| 5,859,009 A | 1/1999 | Schaper et al. |
| 5,859,034 A | 1/1999 | Warrellow et al. |
| 5,866,593 A | 2/1999 | Warrellow et al. |
| 5,869,516 A | 2/1999 | Arlt et al. |
| 5,877,190 A | 3/1999 | Dhainaut et al. |
| 5,885,834 A | 3/1999 | Epstein |
| 5,891,896 A | 4/1999 | Warrellow et al. |
| 5,902,824 A | 5/1999 | Ulrich |
| 5,932,465 A | 8/1999 | Loughney |
| 5,962,483 A | 10/1999 | Warrellow et al. |
| 5,962,492 A | 10/1999 | Warrellow et al. |
| 5,972,927 A | 10/1999 | Pascal et al. |
| 5,981,527 A | 11/1999 | Daugan et al. |
| 6,011,037 A | 1/2000 | Bar et al. |
| 6,043,252 A | 3/2000 | Bombrun |
| 6,043,263 A | 3/2000 | Bar et al. |
| 6,054,475 A | 4/2000 | Martin et al. |
| 6,069,151 A | 5/2000 | Dyke et al. |
| 6,077,854 A | 6/2000 | Warrellow et al. |
| 6,080,782 A | 6/2000 | Ulrich et al. |
| 6,080,790 A | 6/2000 | Boyd et al. |
| 6,103,718 A | 8/2000 | Sterk |
| 6,107,295 A | 8/2000 | Rochus et al. |
| 6,117,881 A | 9/2000 | Bombrun |
| 6,121,279 A | 9/2000 | Gutterer |
| 6,127,363 A | 10/2000 | Doherty, Jr. et al. |
| 6,127,378 A | 10/2000 | Gutterer |
| 6,130,333 A | 10/2000 | Huang et al. |
| 6,136,821 A | 10/2000 | Hersperger |
| 6,140,329 A | 10/2000 | Daugan |
| 6,143,777 A | 11/2000 | Jonas et al. |
| 6,146,876 A | 11/2000 | Robision et al. |
| 6,156,753 A | 12/2000 | Doherty, Jr. et al. |
| 6,166,041 A | 12/2000 | Cavalla et al. |
| 6,191,138 B1 | 2/2001 | Gutterer |
| 6,197,792 B1 | 3/2001 | Alexander et al. |
| 6,211,203 B1 | 4/2001 | Amschler |
| 6,228,859 B1 | 5/2001 | Cavalla et al. |
| 6,245,774 B1 | 6/2001 | Warrellow et al. |
| 6,251,904 B1 | 6/2001 | Bunnage et al. |
| 6,251,923 B1 | 6/2001 | Hofgen et al. |
| 6,258,833 B1 | 7/2001 | Martins et al. |
| 6,258,843 B1 | 7/2001 | Manley |
| 6,294,561 B1 | 9/2001 | Fowler et al. |
| 6,297,248 B1 | 10/2001 | Shimamoto et al. |
| 6,297,257 B1 | 10/2001 | Napoletano et al. |
| 6,297,264 B1 | 10/2001 | Head et al. |
| 6,303,789 B1 | 10/2001 | Bar |
| 6,306,869 B1 | 10/2001 | Flockerzi |
| 6,306,870 B1 | 10/2001 | Bombrun |
| 6,313,116 B1 | 11/2001 | Dyke et al. |
| 6,313,156 B1 | 11/2001 | Fowler et al. |
| 6,316,472 B1 | 11/2001 | Frenette et al. |
| 6,331,543 B1 | 12/2001 | Garvey et al. |
| 6,331,548 B1 | 12/2001 | Shimamoto et al. |
| 6,333,354 B1 | 12/2001 | Schudt |
| 6,348,602 B1 | 2/2002 | Fowler et al. |
| 6,362,178 B1 | 3/2002 | Niewohner et al. |
| 6,362,213 B1 | 3/2002 | Gaudino |
| 6,365,585 B1 | 4/2002 | Jacobelli et al. |
| 6,372,777 B1 | 4/2002 | Martins et al. |
| 6,376,485 B1 | 4/2002 | Martin |
| 6,376,489 B1 | 4/2002 | Martins et al. |
| 6,376,535 B2 | 4/2002 | Ohshima et al. |
| 6,384,236 B1 | 5/2002 | Kleinman |
| 6,407,108 B1 | 6/2002 | Ferrer et al. |
| 6,410,547 B1 | 6/2002 | Manley |
| 6,423,710 B1 | 7/2002 | Martins et al. |
| 6,444,671 B1 | 9/2002 | Gaudino |
| 6,455,562 B1 | 9/2002 | Fowler et al. |
| 6,458,787 B1 | 10/2002 | Martins et al. |
| 6,458,951 B1 | 10/2002 | Bunnage et al. |
| 6,462,047 B1 | 10/2002 | Bombrun et al. |
| 6,469,012 B1 | 10/2002 | Ellis et al. |
| 6,479,494 B1 | 11/2002 | Rochus et al. |
| 6,486,186 B2 | 11/2002 | Fowler et al. |
| 6,492,358 B2 | 12/2002 | Sui et al. |
| 6,498,160 B2 | 12/2002 | Napoletano et al. |
| 6,500,856 B2 | 12/2002 | Fowler et al. |
| 6,514,996 B2 | 2/2003 | Ohshima et al. |
| 6,541,480 B2 | 4/2003 | Shimamoto et al. |
| 6,545,025 B2 | 4/2003 | Hofgen et al. |
| 6,545,158 B2 | 4/2003 | Hofgen et al. |
| 6,555,572 B2 | 4/2003 | Lauener et al. |
| 6,559,168 B2 | 5/2003 | Marfat et al. |
| 6,566,360 B1 | 5/2003 | Niewohner et al. |
| 6,569,885 B1 | 5/2003 | Martins et al. |
| 6,569,890 B2 | 5/2003 | Martins et al. |
| 6,576,644 B2 | 6/2003 | Bi et al. |
| 6,582,351 B1 | 6/2003 | Sawada et al. |
| 6,602,890 B2 | 8/2003 | Hofgen et al. |
| 6,613,778 B1 | 9/2003 | Eggenweiler et al. |
| 6,613,794 B2 | 9/2003 | Hofgen et al. |
| 6,617,357 B2 | 9/2003 | Aubart et al. |
| 6,635,638 B2 | 10/2003 | Sui et al. |
| 6,642,250 B2 | 11/2003 | Aotsuka et al. |
| 6,677,335 B1 | 1/2004 | Bunnage et al. |
| 6,680,336 B2 | 1/2004 | Martins et al. |
| 6,686,349 B2 | 2/2004 | Jiang et al. |
| 6,716,987 B1 | 4/2004 | Ohshima et al. |
| 6,737,436 B1 | 5/2004 | Eggenweiler et al. |
| 6,740,655 B2 | 5/2004 | Magee et al. |
| 6,740,662 B1 | 5/2004 | Iwata et al. |
| 6,743,802 B2 | 6/2004 | Guay et al. |
| 6,747,035 B2 | 6/2004 | Guadilliere et al. |
| 6,761,987 B2 | 7/2004 | Marvin et al. |
| 6,787,548 B1 | 9/2004 | Jonas et al. |
| 6,787,554 B2 | 9/2004 | Gaudilliere et al. |
| RE38,624 E | 10/2004 | Hofgen et al. |
| 6,800,625 B2 | 10/2004 | Jiang et al. |
| 6,818,646 B2 | 11/2004 | Sui et al. |
| 6,818,651 B2 | 11/2004 | Weinbrenner et al. |
| 6,821,975 B1 | 11/2004 | Anderson et al. |
| 6,825,197 B2 | 11/2004 | Orme et al. |
| 6,828,315 B1 | 12/2004 | Gaudilliere et al. |
| 6,828,333 B2 | 12/2004 | Marfat et al. |
| 6,838,559 B2 | 1/2005 | Vaccaro et al. |
| 6,864,253 B2 | 3/2005 | Sui et al. |
| 6,869,945 B2 | 3/2005 | Marfat et al. |
| 6,884,800 B1 | 4/2005 | Eggenweiler et al. |
| 6,894,041 B2 | 5/2005 | Marfat et al. |
| 6,900,205 B2 | 5/2005 | Wang et al. |
| 6,924,292 B2 | 8/2005 | Kawano et al. |
| 6,930,114 B2 | 8/2005 | Niewohner et al. |
| 6,943,166 B1 | 9/2005 | Pullman et al. |
| 6,943,253 B2 | 9/2005 | Vidal Juan et al. |
| 6,949,573 B2 | 9/2005 | Bailey et al. |
| 6,953,810 B2 | 10/2005 | Chambers et al. |
| 2002/0106731 A1 | 8/2002 | Ruben et al. |
| 2002/0115176 A1 | 8/2002 | Lanfear et al. |
| 2002/0132754 A1 | 9/2002 | Boss et al. |
| 2002/0198198 A1 | 12/2002 | Bernardelli et al. |
| 2003/0045490 A1 | 3/2003 | Dale et al. |
| 2003/0045557 A1 | 3/2003 | Vergne et al. |
| 2003/0092721 A1 | 5/2003 | Pitts et al. |

| | | | |
|---|---|---|---|
| 2003/0092908 | A1 | 5/2003 | Pitts et al. |
| 2003/0100571 | A1 | 5/2003 | Vaccaro et al. |
| 2003/0104974 | A1 | 6/2003 | Pitts et al. |
| 2003/0162802 | A1 | 8/2003 | Guo et al. |
| 2003/0166641 | A1 | 9/2003 | Sui et al. |
| 2003/0190672 | A1 | 10/2003 | Omori et al. |
| 2004/0018542 | A1 | 1/2004 | Lanfear et al. |
| 2004/0023945 | A1 | 2/2004 | Martins et al. |
| 2004/0067945 | A1 | 4/2004 | Niewohner et al. |
| 2004/0106631 | A1 | 6/2004 | Bernardelli et al. |
| 2004/0138249 | A1 | 7/2004 | Niewohner et al. |
| 2004/0138279 | A1 | 7/2004 | Eggenweiler et al. |
| 2004/0152754 | A1 | 8/2004 | Martins et al. |
| 2004/0185429 | A1 | 9/2004 | Kelleher-Andersson et al. |
| 2004/0214843 | A1 | 10/2004 | Bernardelli et al. |
| 2004/0229291 | A1 | 11/2004 | Zhou et al. |
| 2004/0249148 | A1 | 12/2004 | Erguden et al. |
| 2004/0254152 | A1 | 12/2004 | Monje et al. |
| 2005/0004046 | A1 | 1/2005 | Praag et al. |
| 2005/0009062 | A1 | 1/2005 | Loughney |
| 2005/0009742 | A1 | 1/2005 | Bertilsson et al. |
| 2005/0009847 | A1 | 1/2005 | Bertilsson et al. |
| 2005/0026913 | A1 | 2/2005 | Tehim et al. |
| 2005/0031538 | A1 | 2/2005 | Steindler et al. |
| 2005/0032702 | A1 | 2/2005 | Eriksson |
| 2005/0059686 | A1 | 3/2005 | Eggenweiler et al. |
| 2005/0070541 | A1 | 3/2005 | Niewohner et al. |
| 2005/0113402 | A1 | 5/2005 | Sui et al. |
| 2005/0119225 | A1 | 6/2005 | Schumacher et al. |
| 2005/0148604 | A1 | 7/2005 | Inoue et al. |
| 2005/0222138 | A1 | 10/2005 | Ohhata et al. |
| 2006/0106085 | A1* | 5/2006 | Zeldis et al. |

FOREIGN PATENT DOCUMENTS

| | | | |
|---|---|---|---|
| EP | 685479 | A1 | 12/1995 |
| EP | 0763534 | A1 | 3/1997 |
| EP | 819688 | A1 | 1/1998 |
| EP | 0702555 | B1 | 3/1998 |
| EP | 1579862 | A2 | 9/2005 |
| WO | WO93/07124 | A1 | 4/1993 |
| WO | WO94/22852 | A1 | 10/1994 |
| WO | WO94/28902 | A1 | 12/1994 |
| WO | WO95/01338 | A1 | 1/1995 |
| WO | WO95/19978 | A1 | 7/1995 |
| WO | WO95/35283 | A1 | 12/1995 |
| WO | WO96/00215 | A1 | 1/1996 |
| WO | WO96/16644 | A1 | 6/1996 |
| WO | WO96/16657 | A1 | 6/1996 |
| WO | WO96/26940 | A1 | 6/1996 |
| WO | WO97/22585 | A1 | 6/1997 |
| WO | WO97/36905 | A1 | 10/1997 |
| WO | WO97/42174 | A1 | 11/1997 |
| WO | WO97/43287 | A1 | 11/1997 |
| WO | WO97/44036 | A1 | 11/1997 |
| WO | WO97/44322 | A1 | 11/1997 |
| WO | WO97/44337 | A1 | 11/1997 |
| WO | WO97/48697 | A1 | 12/1997 |
| WO | WO97/49702 | A1 | 12/1997 |
| WO | WO98/02440 | A1 | 1/1998 |
| WO | WO98/06704 | A1 | 2/1998 |
| WO | WO98/14432 | A1 | 4/1998 |
| WO | WO98/17896 | A1 | 5/1998 |
| WO | WO98/20007 | A1 | 5/1998 |
| WO | WO99/07704 | A1 | 2/1999 |
| WO | WO99/65880 | A1 | 12/1999 |
| WO | WO00/26201 | A1 | 5/2000 |
| WO | WO00/40714 | A2 | 7/2000 |
| WO | WO00/59890 | A1 | 10/2000 |
| WO | WO01/19802 | A1 | 3/2001 |
| WO | WO02/096423 | A2 | 12/2002 |
| WO | WO02/096463 | A1 | 12/2002 |
| WO | WO2004/014911 | A1 | 2/2004 |
| WO | WO2006/050057 | A2 | 5/2006 |
| WO | WO2007/030697 | A2 | 3/2007 |

OTHER PUBLICATIONS

Bielenberg et al., Stroke, 1990, vol. 21(12) Supplement IV, pp. IV161-IV163.*

Angel et al., AIDS, 1995, vol. 9(10), pp. 1137-1144; Abstract provided, 3 pages.*

Hirsch et al., International Conference on AIDS, Jun. 20-23, 1990 6:184, abstract No. S.B.395; 2 pages.*

Aoki, Motonori, et al. "A Novel Phosphodiesterase Type 4 Inhibitor, YM976 (4-(3-Chlorophenyl)-1,7-diethylpyrido[2,3-*d*]pyrimidin-2(1*H*-one), with Little Emetogenic Activity", *J. Pharmacol. Exp. Ther.* (2000) 295(1):255-260.

Ashton, Michael J., et al. "Selective Type IV Phosphodiesterase Inhibitors as Antiasthmatic Agents. The Synthese and Biological Activities of 3-(Chyclopentyloxy)-4-methoxy benzamides and Analogues", *J. Med. Chem.* (1994) 37:1696-1703.

Atienza, Josephine M., et al. "Identification of Inhibitor Specificity Determinants in a Mammalian Phosphodiesterase", *J. Biol. Chem.* (1997) 274:4839-4847.

Barnette, et al. "Phosphodiesterase 4: Biological Underpinnings for the Design of Improved Inhibitors", *Pharmcol. Rev. Commun.* (1997) 8:65-73.

Bi, Yingzhi, et al. "The Discovery of Novel, Potent and Selective PDE5 Inhibitors", *Bioorg Med. Chem. Lett.* (2001) 11(18):2461-2464.

Boess, Frank G., et al. "Inhibition of phosphodiesterase 2 increases neuronal cGMP, synaptic plasticity and memory performance", *Neuropharmacology* (2004) 47(7):1081-1092.

Boyle, Craig D., et al. "Optimization of purine based PDE1/PDE5 inhibitors to a potent ans selective PDE5 inhibitor for the treatment of male ED", *Bioorg Med Chem Lett.* (2005) 15(9):2365-2369.

Brown, Jason, et al. "Enriched environment and physical activity stimulate hippocampal but not olfactory bulb neurogenesis", *Eur J Neurosci.* (2003) 17(10):2042-2046.

Cameron, H.A., et al. "Adult neurogenesis is regulated by adrenal steroids in the dentate gyrus", *Neuroscience* (1994) 61(2):203-209.

Chen, Jieli, et al. "Statins Induce Angiogenesis, Neurogenesis, and Synaptogenesis After Stroke", *Annals of Neurology* (2003) 53(6):743-751.

Daugan, Alain, et al. "The Discovery of Tadalafil: A Novel and Highly Selective PDE5 Inhibitor. 2:2,3,6,7,12,12a-hexahydropyrazino[1',2':1,6]pyrido[3,4-*b*] indole-1,4-dione Analogues",*J. Med. Chem.* (2003) 46(2):4533-4542.

Daugan, et al. "The Discovery of Tadalafil: A Novel and Highly Selective PDE5 Inhibitor. 1:5,6,11,11a-Tetrahydro-1*H*-Imidazo[1',5':1,6]pyrido[3,4-*b*]indole-1,3(2*H*)-dione Analogues", *J. Med. Chem.* (2003) 9;46(21):4525-4532.

Davis, Craig, et al. "Assessment of Selective Inhibition of Rat Cerebral Cortical Calcium-Independent and Calcium-Dependent Phosphodiesterases in Crude Extracts Using Deoxycyclic AMP and Potassium Ions", *Biochim. Biophys. Acta* (1984) 797:354-362.

Dal Piaz, et al. "Phosphodiesterase 4 inhibitors, structurally unrelated to Rolipram, as promising agents for the treatment of asthma and other pathologies", *Eur. J. Med. Chem.* (2000) 35:463-480.

Dunn, Peter J. "Synthesis of Commercial Phosphodiesterase(V) Inhibitors", *Organic Process Research & Development.* (2005) 9:88-97.

Eddahibi, Saadia, et al. "Effect of DMPPO, a phosphodiesterase type 5 inhibitor, on hypoxic pulmonary hypertension in rats", *Br. J. Pharmacol.* (1988) 125(4):681-688.

Eisch, Amelia, J., et al. "Drug dependence and addiction II: Adult neurogenesis and drug addiction", *Am J Psychiatry* (2004) 161(3):426.

Fujimaki, Koichiro, et al. "Administration of a cAMP Phosphodiesterase 4 Inhibitor Enhances Antidepressant-Induction of BDNF mRNA in Rat Hippocampus", *Neuropsychopharmacology* (2000) 22(1):42-51.

Gage, F.H., et al. "Adult brain neurogenesis and psychiatry: a novel theory of depression", *Molecular Psychiatry*. (2000) 5(3):262-269.

Gould, Elizabeth, et al. "Neurogenesis in the neocortex of adult primates", *Science.* (1999) 286(5439):548-552.

Hersperger, Rene, et al. "Palladium-Catalyzed Cross-Coupling Reactions for the Synthesis of 6,8-Disubstituted 1,7-Naphthyridines: A Novel Class of Potent and Selective Phosphodiesterase Type 4D Inhibitors", *J. Med. Chem.* (2000) 43(4):675-682.

Jin, S.-L. Catherine, et al. "Characterization of the Structure of a Low K$_m$, Rolipram-sensitive cAMP Phosphodiesterase", *J. Biol Chem.* (1992) 267:18929-18939.

Keller, Thomas H., et al. "Synthesis and Structure—Activity Relationship of N-Arylrolipram Derivatives as Inhibitors of PDE4 Isozymes" *Chem. Pharm Bull* (Tokyo) (2001) 8:1009-1017.

Kim, J.E., et al. "Chronic Administration of Rolipram, A Cyclic-Amp Phosphodiesterase-4 Inhibitor, Upregulates Neurogenesis in the Adult Mouse Hippocampus", *Abstracts of the Society for Neuroscience, Society for Neuroscience* (2001) 26(102):2316.

Kincaid, Randall, L., et al. "Purification and Properties of Calmodulin-stimulated Phosphodiesterase from Mammalian Brain", *J. Biol. Chem.* (1984) 259(8):5158-5166.

Kincaid, Randall L., et al. "Assay of Cyclic Nucleotide Phosphodiesterase Using Radiolabeled and Fluorescent Substrates", *Methods in Enzymology.* (1988) 159:457-470.

Kuhn, H. George, et al. "Neurogenesis in the gentate gyrus of the adult rat: Age-related decrease neuronal progenitor proliferation", *Neurosci.* (1996) 16(6):2027-2033.

Lee, Mi Eun, et al. Crystal structure of phosphodiesterase 4D and Inhibitor complex, *FEBS LETT* (2002) 530(1-3):53-58.

Loughney, Kate, et al., "Isolation and Characterization of cDNAs Corresponding to Two Human Calcium, Calmodulin-regulated, 3',5'-Cyclic Nucleotide Phosphodiesterases", *J. Biol. Chem.* (1996) 271:796-806.

Malberg, Jessica E., et al. "Chronic Antidepressant Treatment Increases Neurogenesis in Adult Rat Hippocampus", *The Journal of Neuroscience* (2000) 20(24):9104-9110.

Maw, Graham, N., et al. "Design, Synthesis and Biological Activity of β-Carboline-Based Type-5 Phosphodiesterase Inhibitors", *Bioorg Med Chem Lett* (2003) 13(8):1425-1428.

McEwen, Bruce S., et al. "Hippocampal remodeling and damage by corticosteroids: Implications for mood disorders", *Neuropsychopharmacology.* (1999) 21(4):474-84.

Nagakawa, Shin, et al. "Regulation of Neurogenesis in Adult Mouse Hippocampus by cAMP and the cAMP Response Element-Binding Protein", *The Journal of Neuroscience* (2002) 22(9):3673-3682.

Perrier, Hlène, et al. "Substituted Furans as Inhibitors of the PDE4 Enzyme", *Bioorg. Med. Che. Lett.* (1999) 9:323-326.

Rich, Thomas C., et al. "In Vivo Assessment of Local Phosophodiesterase Activity Using Tailored Cyclic Nucleotide-gated Channels as cAMP Sensors", *J. Gen. Physiology* (2001) 118(1):63-78.

Richter, Wito et al. "Identification of substrate specificity determinants in human cAMP-specific phosphodiesterase 4A by single-point mutagenesis", *Cell Signal* (2001) 13(3):159-167.

Santarelli, Luca, et al. "Requirement of hippocampal neurogenesis for the behavioral effects of antidepressants", *Science.* (2003) 301(5634):805-809.

Thompson, W. Joseph, et al. "Multiple Cyclis Nucleotide Phosphodiesterase activities from Rat Brain", *Biochemistry* (1971) 10:311-316.

Trifilieff, Alexandre, et al. "Pharmacological Profile of a Novel Phosphodiesterase 4 Inhibitor, 4-(8-Benzo[1,2,5]oxadiazol-5-yl-[1,7]naphthyridin-6-yl)-benzoic Acid (NVP-ABE171), a 1,7-Naphthyridine Derivative, with Anti-Inflammatory Activities", *Pharmacology* (2002) 301(1):241-248.

Ukita, Tatsuzo, et al. "1-Arylnapthalene Lignan: A Novel Scaffold for Type 5 Phosphodiesterase Inhibitor", *J. Med. Chem.* (1999) 42(7):1293-1305.

van Praag, Henriette, et al. "Running enhances neurogenesis, learning and long-term potentiation in mice", *Proc Natl Acad Sci U S A.* (1999) 96(23):13427-13431.

Weeks, et al. "Radiolabeled Ligand Binding to the Catalytic or Allosteric Sites of PDE5 and PDE11", *Methods Mol Biol.* (2005) 307:239-262.

Wong, Ma-Li, et al. "Phosphodiesterase genes are associated with susceptibility to major depression and antidepressant treatment response", *PNAS* (2006) 103(41):15124-15129.

Xu, Robert X. et al. "Atomic Structure of PDE4: Insights into Phosphodiesterase Mechanism and Specificity", *Science (Wash DC)* (2000) 288:1822-1825.

Yehuda, Rachel, et al. "Enhanced Brain Cell Proliferation Following Early Adrenalectomy in Rats", *J Neurochem.* (1989) 53(1):241-8.

\* cited by examiner

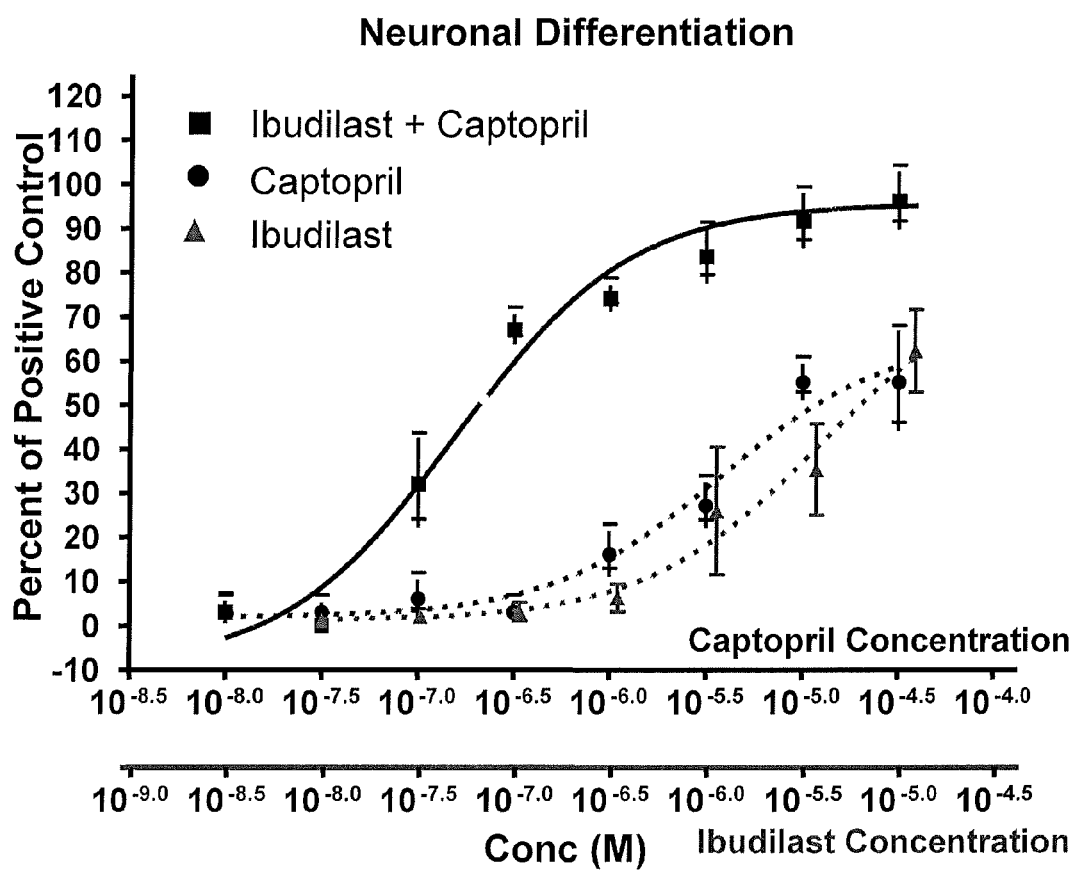
Figure 1: Human Neurogenesis Assay: Ibudilast + Captopril

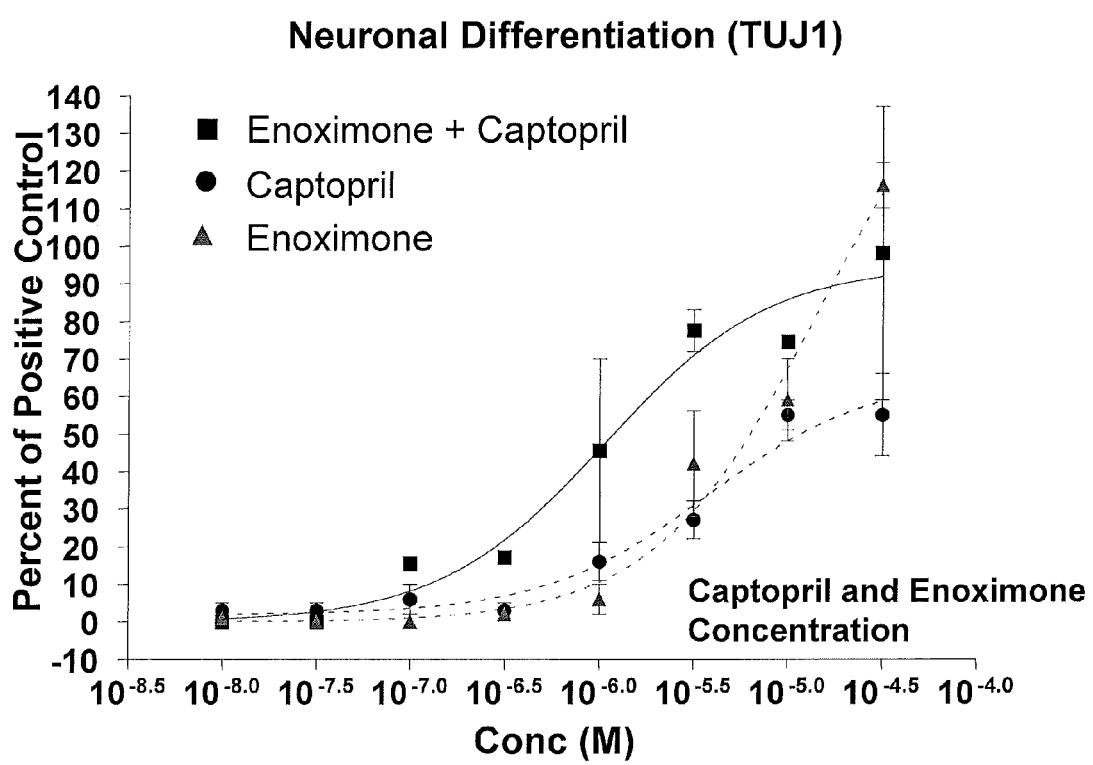
Figure 2: Human Neurogenesis Assay: Enoximone + Captopril

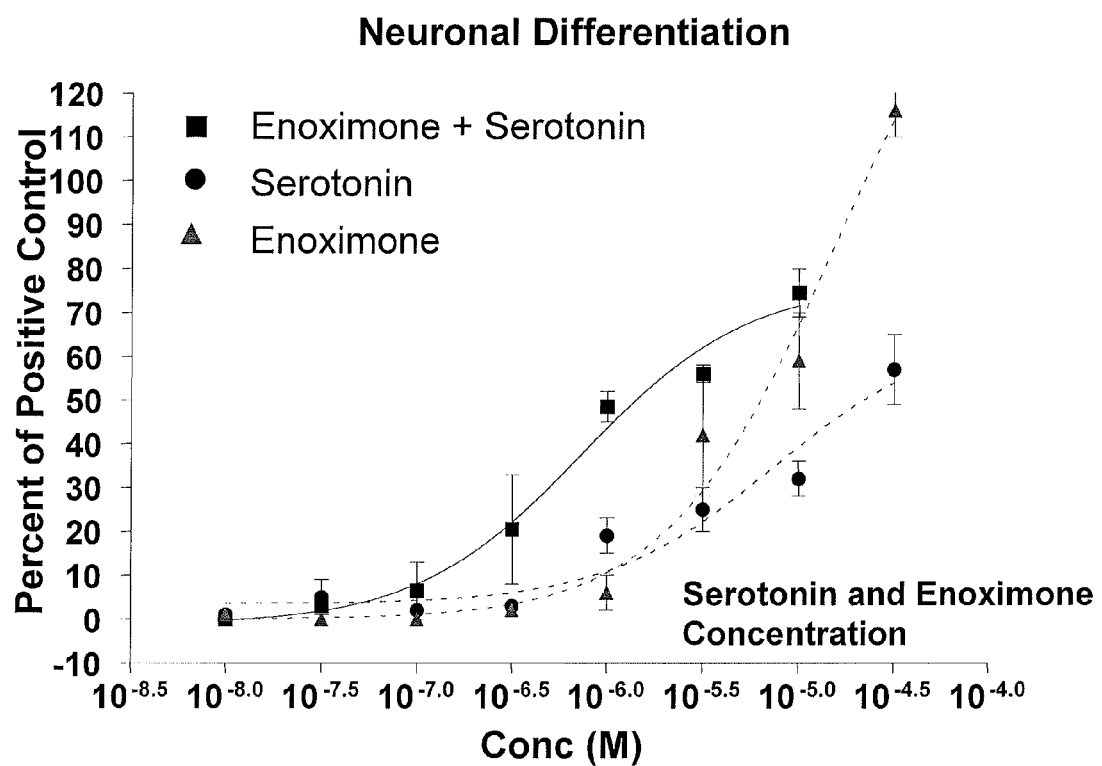
Figure 3: Human Neurogenesis Assay: Enoximone + Serotonin

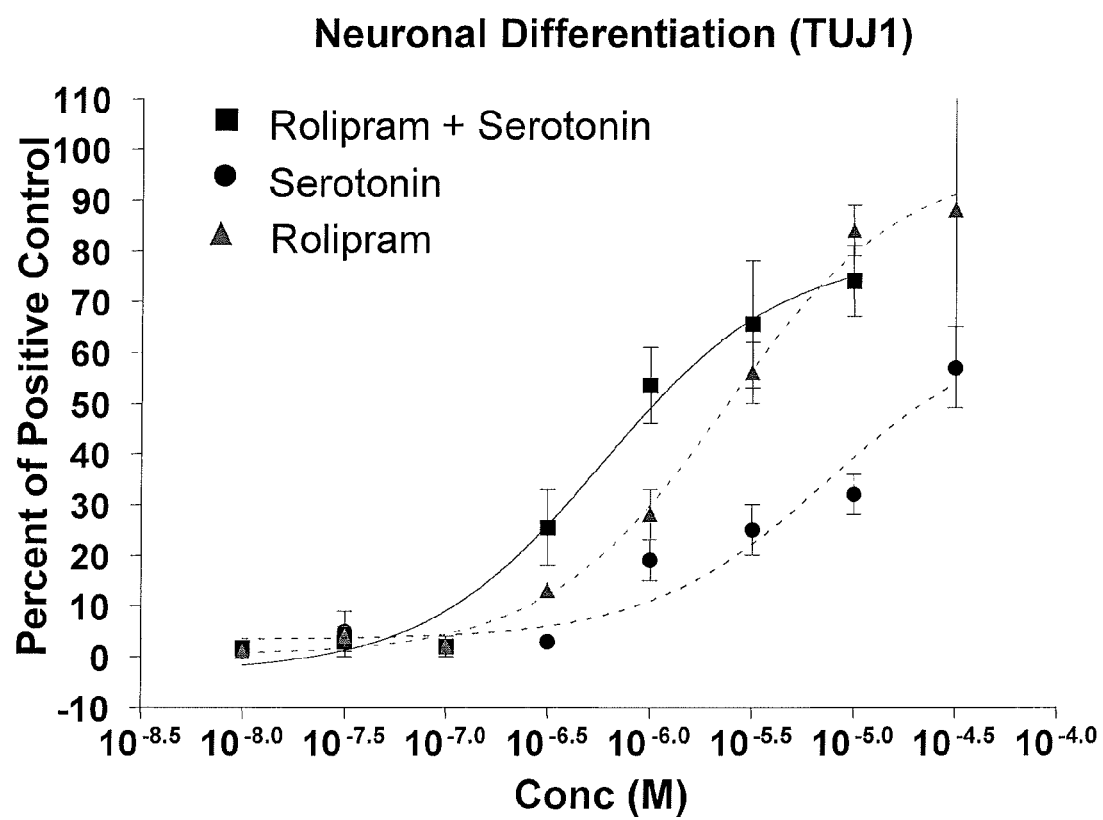

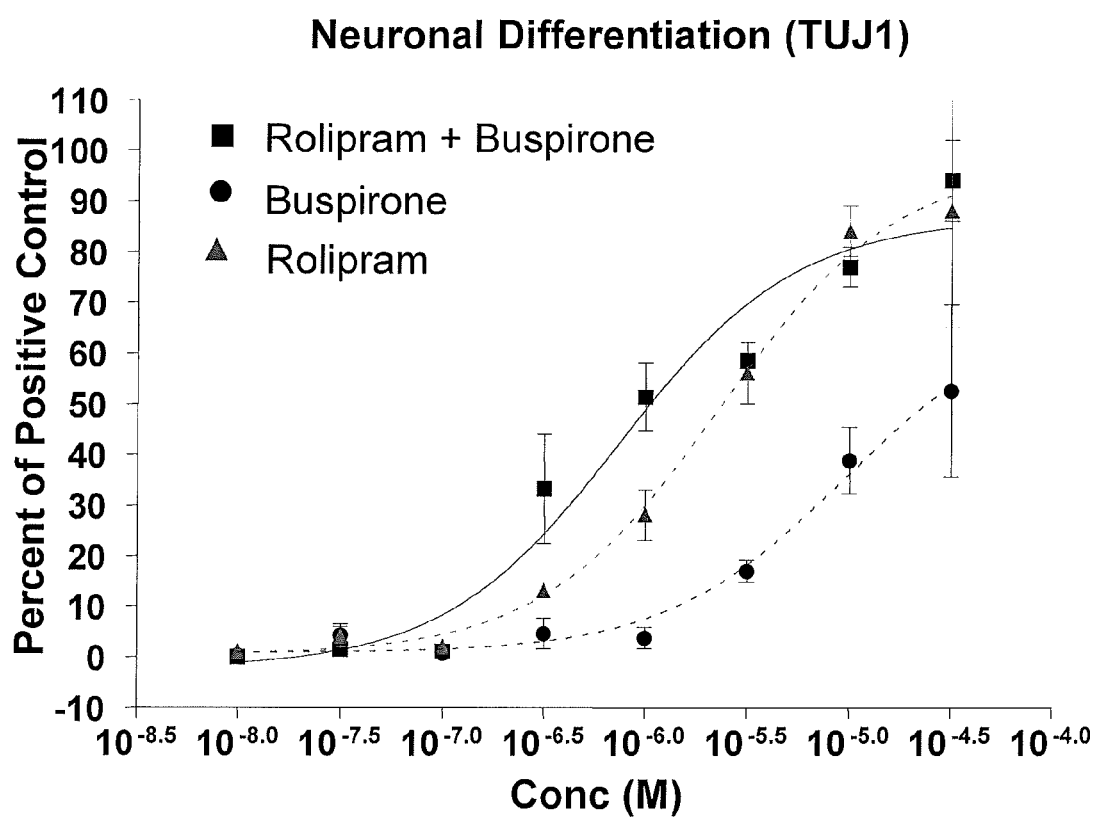
Figure 5: Human Neurogenesis Assay: Rolipram + Buspirone

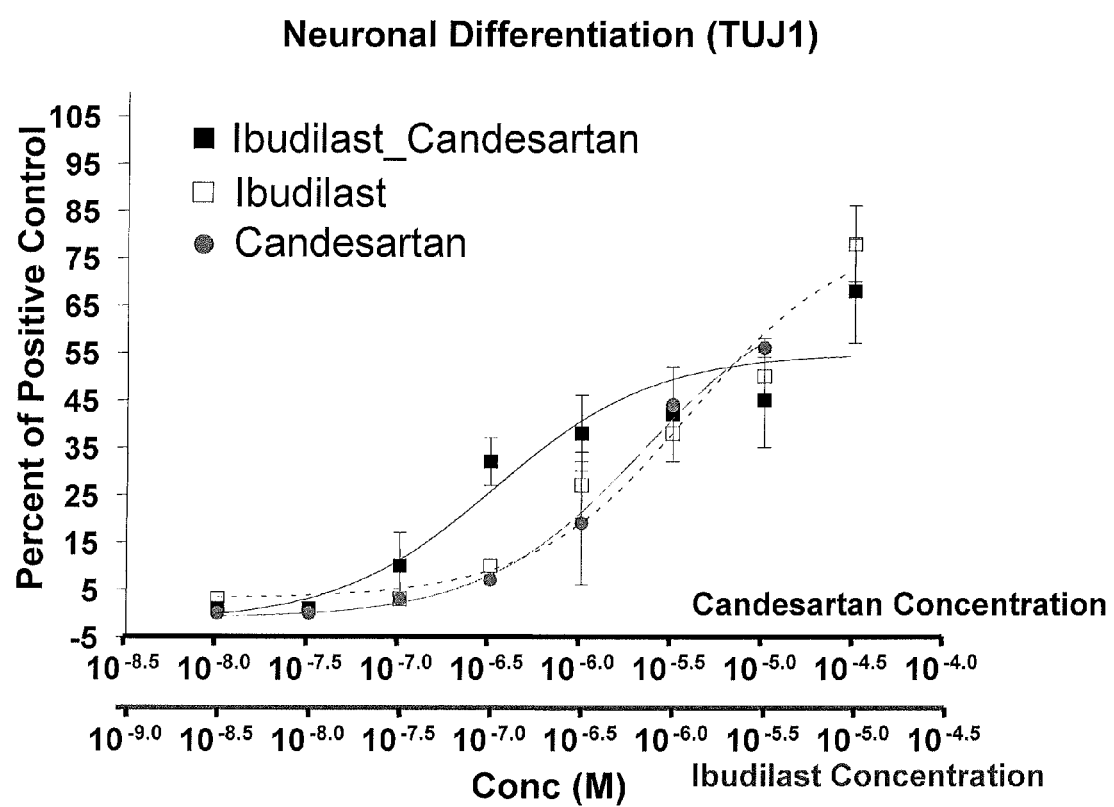
Figure 6: Human Neurogenesis Assay:
Ibudilast + Candesartan

MODULATION OF NEUROGENESIS BY PDE INHIBITION

RELATED APPLICATIONS

This application claims benefit of priority from U.S. Provisional Patent Application 60/729,366, filed Oct. 21, 2005, 60/784,605, filed Mar. 21, 2006, and 60/807,594, filed Jul. 17, 2006. All three of these applications are hereby incorporated by reference as if fully set forth.

FIELD OF THE DISCLOSURE

The instant disclosure relates to methods for treating diseases and conditions of the central and peripheral nervous system by stimulating or increasing neurogenesis via inhibition of cyclic nucleotide phosphodiesterase ("PDE") activity, optionally in combination with another neurogenic agent. The disclosure includes methods based on the application of an PDE inhibitor and another neurogenic agent to stimulate or activate the formation of new nerve cells.

BACKGROUND OF THE DISCLOSURE

Neurogenesis is a vital process in the brains of animals and humans, whereby new nerve cells are continuously generated throughout the life span of the organism. The newly born cells are able to differentiate into functional cells of the central nervous system and integrate into existing neural circuits in the brain. Neurogenesis is known to persist throughout adulthood in two regions of the mammalian brain: the subventricular zone (SVZ) of the lateral ventricles and the dentate gyrus of the hippocampus. In these regions, multipotent neural progenitor cells (NPCs) continue to divide and give rise to new functional neurons and glial cells (for review Gage 2000). It has been shown that a variety of factors can stimulate adult hippocampal neurogenesis, e.g., adrenalectomy, voluntary exercise, enriched environment, hippocampus dependent learning and anti-depressants (Yehuda 1989, van Praag 1999, Brown J 2003, Gould 1999, Malberg 2000, Santarelli 2003). Other factors, such as adrenal hormones, stress, age and drugs of abuse negatively influence neurogenesis (Cameron 1994, McEwen 1999, Kuhn 1996, Eisch 2004).

Cyclic adenosine monophosphate (cAMP) and cyclic guanosine monophosphate (cGMP) are ubiquitous second messengers that mediate a wide range of processes in mammalian cells, including vision, olfaction, platelet aggregation, aldosterone synthesis, insulin secretion, T cell activation, and smooth muscle relaxation. Cyclic nucleotide phosphodiesterases ("PDEs") regulate intracellular levels of cAMP and cGMP by catalyzing their hydrolysis to the corresponding nucleotide 5'-monophosphates. Over 20 PDE genes have been cloned, encoding 11 gene families (PDE1-PDE11), which are classified according to sequence homology, as well as the biochemical and pharmacological properties of the encoded PDEs (e.g., specificity for cAMP and/or cGMP, response to modulatory compounds).

PDE families that specifically/preferentially hydrolyze cAMP include PDE4, PDE7, and PDE8, whereas families that specifically/preferentially hydrolyze cGMP include PDE5, PDE6, and PDE9. The PDE1, PDE2, PDE3, PDE10, and PDE11 families show substantial activity agonist both cAMP and cGMP. Many PDE gene families comprise multiple genes, which give rise to distinct isozymes. For example, the PDE3, PDE6, PDE7, and PDE8 families each comprise at least two genes (3A, 3B; 6A, 6B; 7A, 7B; 8A, 8B), while the PDE1 family comprises at least three genes (1A, 1B, 1C), and the PDE4 family comprises at least four genes (4A, 4B, 4C, 4D). In addition, the majority of PDE gene transcripts are subject to alternative splicing, giving rise to multiple isozymes within each family. PDE isozymes are differentially expressed in various tissues, cell types, and subcellular locations, and numerous PDE isozymes have been detected throughout the CNS.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

BRIEF SUMMARY OF THE DISCLOSURE

Disclosed herein are compositions and methods for the prophylaxis and treatment of diseases, conditions and injuries of the central and peripheral nervous systems by stimulating or increasing neurogenesis. Aspects of the methods, and activities of the compositions, include increasing or potentiating neurogenesis in cases of a disease, disorder, or condition of the nervous system. Embodiments of the disclosure include methods of treating a neurodegenerative disorder, neurological trauma including brain or central nervous system trauma and/or recovery therefrom, depression, anxiety, psychosis, learning and memory disorders, and ischemia of the central and/or peripheral nervous systems. In other embodiments, the disclosed methods are used to improve cognitive outcomes and mood disorders.

In one aspect, methods of modulating, such as by stimulating or increasing, neurogenesis are disclosed. The neurogenesis may be at the level of a cell or tissue. The cell or tissue may be present in an animal subject or a human being, or alternatively be in an in vitro or ex vivo setting. In some embodiments, neurogenesis is stimulated or increased in a neural cell or tissue, such as that of the central or peripheral nervous system of an animal or human being. In cases of an animal or human, the methods may be practiced in connection with one or more diseases, disorders, or conditions of the nervous system as present in the animal or human subject. Thus, embodiments disclosed herein include methods of treating a disease, disorder, or condition by administering at least one neurogenesis modulating agent having inhibitory activity against a cyclic nucleotide phosphodiesterase ("PDE"), hereinafter referred to as a "PDE agent". A PDE agent may be formulated or used alone, or in combination with one or more additional neurogenic agents, such as another PDE agent or a non-PDE agent.

The disclosure thus includes a method of using a chemical entity as a PDE agent to increase neurogenesis. In some embodiments, a chemical entity used as an agent is a therapeutically or pharmaceutically acceptable reversible PDE inhibitor. Alternatively, an acceptable irreversible PDE inhibitor may also be used in some embodiments of the disclosure. Additional embodiments comprise an inhibitor that is a tertiary amine which crosses the blood brain barrier.

While a PDE agent may be considered a "direct" agent in that it has direct activity against a PDE by interactions therewith, the disclosure includes a PDE agent that may be considered an "indirect" agent in that it does not directly interact with a PDE. Thus, an indirect agent acts on a PDE indirectly, or via production, generation, stability, or retention of an intermediate agent which directly interacts with a PDE.

Embodiments of the disclosure include a combination of a PDE agent and one or more other neurogenic agents disclosed herein or known to the skilled person. An additional neurogenic agent as described herein may be a direct PDE agent, an indirect PDE agent, or a neurogenic agent that does not act, directly or indirectly, through a PDE. Thus in some embodiments, an additional neurogenic agent is one that acts, directly or indirectly, through a mechanism other than a PDE. An additional neurogenic agent as described herein may be one which acts through a known receptor or one which is known for the treatment of a disease or condition. The disclosure further includes a composition comprising a combination of a PDE agent with one or more other neurogenic agents.

In a second aspect, the disclosure includes a method of lessening and/or reducing a decline or decrease of cognitive function in a subject or patient. In some cases, the method may be applied to maintain and/or stabilize cognitive function in the subject or patient. The method may comprise administering a PDE agent, optionally in combination with one or more other neurogenic agents, to a subject or patient in an amount effective to lessen or reduce a decline or decrease of cognitive function.

In an additional aspect, the disclosure includes a method of treating mood disorders with use of a PDE agent, optionally in combination with one or more other neurogenic agents. In some embodiments, the method may be used to moderate or alleviate a mood disorder in a subject or patient. Non-limiting examples include a subject or patient having, or diagnosed with, a disease or condition as described herein. In other embodiments, the method may be used to improve, maintain, or stabilize mood in a subject or patient. Of course the method may be optionally combined with any other therapy or condition used in the treatment of a mood disorder.

In a third aspect, the disclosed methods include identifying a patient suffering from one or more diseases, disorders, or conditions, or a symptom thereof, and administering to the patient a PDE agent, optionally in combination with one or more other neurogenic agents, as described herein. In some embodiments, a method including identification of a subject as in need of an increase in neurogenesis, and administering to the subject a PDE agent, optionally in combination with one or more other neurogenic agents is disclosed herein. In other embodiments, the subject is a patient, such as a human patient.

Another aspect of the disclosure describes a method including administering a PDE agent, optionally in combination with one or more other neurogenic agents, to a subject exhibiting the effects of insufficient amounts of, or inadequate levels of, neurogenesis. In some embodiments, the subject may be one that has been subjected to an agent that decreases or inhibits neurogenesis. Non-limiting examples of an inhibitor of neurogenesis include opioid receptor agonists, such as a mu receptor subtype agonist like morphine. In other cases, the need for additional neurogenesis is that detectable as a reduction in cognitive function, such as that due to age-related cognitive decline, Alzheimer's Disease, epilepsy, or a condition associated with epilepsy as non-limiting examples.

In a related manner, a method may include administering a PDE agent, optionally in combination with one or more other neurogenic agents, to a subject or person that will be subjected to an agent that decreases or inhibits neurogenesis. Non-limiting embodiments include those where the subject or person is about to be administered morphine or another opioid receptor agonist, like another opiate, and so about to be subject to a decrease or inhibition of neurogenesis. Non-limiting examples include administering a PDE agent, optionally in combination with one or more other neurogenic agents, to a subject before, simultaneously with, or after the subject is administered morphine or other opiate in connection with a surgical procedure.

In a fifth aspect, the disclosure includes methods for preparing a population of neural stem cells suitable for transplantation, comprising culturing a population of neural stem cells (NSCs) in vitro, and contacting the cultured neural stem cells with a PDE agent, optionally in combination with one or more other neurogenic agents. In some embodiments, the stem cells are prepared and then transferred to a recipient host animal or human. Non-limiting examples of preparation include 1) contact with a PDE agent, optionally in combination with one or more other neurogenic agents, until the cells have undergone neurogenesis, such as that which is detectable by visual inspection or cell counting, or 2) contact with a PDE agent, optionally in combination with one or more other neurogenic agents, until the cells have been sufficiently stimulated or induced toward or into neurogenesis. The cells prepared in such a non-limiting manner may be transplanted to a subject, optionally with simultaneous, nearly simultaneous, or subsequent administration of another neurogenic agent to the subject. While the neural stem cells may be in the form of an in vitro culture or cell line, in other embodiments, the cells may be part of a tissue which is subsequently transplanted into a subject.

In yet another aspect, the disclosure includes methods of modulating, such as by stimulating or increasing, neurogenesis in a subject by administering a PDE agent, optionally in combination with one or more other neurogenic agents. In some embodiments, the neurogenesis occurs in combination with the stimulation of angiogenesis which provides new cells with access to the circulatory system.

The details of additional embodiments are set forth in the accompanying drawings and the description below. Other features, objects, and advantages of the embodiments will be apparent from the drawings and detailed description, and from the claims.

BRIEF DESCRIPTION OF THE DRAWINGS

FIG. 1 is a dose-response curve showing the effect of the neurogenic agents captopril (angiotensin converting enzyme, or ACE, inhibitor) and ibudilast (PDE inhibitor) in combination on neuronal differentiation compared to the effect of either agent alone. When run independently, ibudilast was tested in a concentration response curve (CRC) ranging from 0.01 µM to 10.0 µM and captopril was tested in a CRC ranging from 0.01 µM to 31.6 µM. In combination, ibudilast was tested in a CRC ranging from 0.003 µM to 10.0 µM and captopril was added at a concentration 3.16-fold higher at each point (for example, the first point in the combined curve reflects a combination of 0.003 µM ibudilast and 0.01 µM captopril). Data is presented as the percentage of the neuronal positive control, with basal media values subtracted. When used alone, $EC_{50}$ was observed at a captopril concentration of 3.8 µM or an ibudilast concentration of 6.2 µM in test cells. When used in combination, $EC_{50}$ was observed in a combination of captopril at a concentration of 0.15 µM and ibudilast at a concentration of 0.05 µM FIG. 2 is a dose-response curve showing the effect of the neurogenic agents captopril (ACE inhibitor) and enoximone (PDE-3 inhibitor) in combination on neuronal differentiation compared to the effect of either agent alone. When run independently, each compound was tested in a concentration response curve ranging from 0.01 µM to 31.6 µM. In combination, the compounds were combined at equal concentrations at each point (for example, the first point in the combined curve consisted of a test of 0.01 µM captopril and 0.01

µM enoximone). Data is presented as the percentage of the neuronal positive control, with basal media values subtracted. When used alone, $EC_{50}$ was observed at a captopril concentration of 3.8 µM or an enoximone concentration of 6.8 µM in test cells. When used in combination, $EC_{50}$ was observed at a combination of captopril and enoximone at concentrations of 1.1 µM each.

FIG. 3 is a dose-response curve analogous to FIG. 2 and showing the effect of the neurogenic agents serotonin and enoximone (PDE-3 inhibitor) in combination on neuronal differentiation compared to the effect of either agent alone. When used alone, $EC_{50}$ was observed at a serotonin concentration of 7.4 µM or an enoximone concentration of 6.8 µM in test cells. When used in combination, $EC_{50}$ was observed at a combination of serotonin and enoximone at concentrations of 0.74 µM each.

FIG. 4 is a dose-response curve analogous to FIGS. 2 and 3 which shows the effect of the neurogenic agents serotonin and rolipram (PDE-4 inhibitor) in combination on neuronal differentiation compared to the effect of either agent alone. When used alone, $EC_{50}$ was observed at a serotonin concentration of 7.4 µM or a rolipram concentration of 2.3 µM in test cells. When used in combination, $EC_{50}$ was observed at a combination of serotonin and rolipram at concentrations of 0.58 µM each.

FIG. 5 is a dose-response curve analogous to FIG. 2 to 4 and showing the effect of the neurogenic agents buspirone (5-HT1a receptor agonist) and rolipram (PDE-4 inhibitor) in combination on neuronal differentiation compared to the effect of either agent alone. When used alone, $EC_{50}$ was observed at a buspirone concentration of 9.4 µM or a rolipram concentration of 2.3 µM in test cells. When used in combination, $EC_{50}$ was observed at a combination of buspirone and rolipram at concentrations of 0.74 µM each.

FIG. 6 is a dose-response curve analogous to that of FIG. 1 and showing the effect of the neurogenic agents ibudilast (PDE inhibitor) and candesartan (angiotensin II AT1 receptor antagonist) in combination on neuronal differentiation compared to the effect of either agent alone. When used alone, $EC_{50}$ was observed at a candesartan concentration of 2.2 µM or an ibudilast concentration of 6.2 µM in test cells. When used in combination, $EC_{50}$ was observed at the combination of candesartan at a concentration of 0.35 µM and ibudilast at a concentration of 0.11 µM.

DEFINITIONS

"Neurogenesis" is defined herein as proliferation, differentiation, migration and/or survival of a neural cell in vivo or in vitro. In some embodiments, the neural cell is an adult, fetal, or embryonic neural stem cell or population of cells. The cells may be located in the central nervous system or elsewhere in an animal or human being. The cells may also be in a tissue, such as neural tissue. In some embodiments, the neural cell is an adult, fetal, or embryonic progenitor cell or population of cells, or a population of cells comprising a mixture of stem cells and progenitor cells. Neural cells include all brain stem cells, all brain progenitor cells, and all brain precursor cells. Neurogenesis includes neurogenesis as it occurs during normal development, as well as neural regeneration that occurs following disease, damage or therapeutic intervention, such as by the treatment described herein.

A "neurogenic agent" is defined as a chemical agent or reagent that can promote, stimulate, or otherwise increase the amount or degree or nature of neurogenesis in vivo or ex vivo or in vitro relative to the amount, degree, or nature of neurogenesis in the absence of the agent or reagent. In some embodiments, treatment with a neurogenic agent increases neurogenesis if it promotes neurogenesis by at least about 5%, at least about 10%, at least about 25%, at least about 50%, at least about 100%, at least about 500%, or more in comparison to the amount, degree, and/or nature of neurogenesis in the absence of the agent, under the conditions of the method used to detect or determine neurogenesis. As described herein, a PDE agent that promotes, stimulates, or otherwise increases the amount or degree or nature of neurogenesis is a neurogenic agent.

The term "astrogenic" is defined in relation to "astrogenesis" which refers to the activation, proliferation, differentiation, migration and/or survival of an astrocytic cell in vivo or in vitro. Non-limiting examples of astrocytic cells include astrocytes, activated microglial cells, astrocyte precursors and potentiated cells, and astrocyte progenitor and derived cells. In some embodiments, the astrocyte is an adult, fetal, or embryonic astrocyte or population of astrocytes. The astrocytes may be located in the central nervous system or elsewhere in an animal or human being. The astrocytes may also be in a tissue, such as neural tissue. In some embodiments, the astrocyte is an adult, fetal, or embryonic progenitor cell or population of cells, or a population of cells comprising a mixture of stem and/or progenitor cells, that is/are capable of developing into astrocytes. Astrogenesis includes the proliferation and/or differentiation of astrocytes as it occurs during normal development, as well as astrogenesis that occurs following disease, damage or therapeutic intervention.

The term "stem cell" (or neural stem cell (NSC)), as used herein, refers to an undifferentiated cell that is capable of self-renewal and differentiation into neurons, astrocytes, and/or oligodendrocytes.

The term "progenitor cell" (e.g., neural progenitor cell), as used herein, refers to a cell derived from a stem cell that is not itself a stem cell. Some progenitor cells can produce progeny that are capable of differentiating into more than one cell type.

The terms "animal" or "animal subject" refers to a non-human mammal, such as a primate, canine, or feline. In other embodiments, the terms refer to an animal that is domesticated (e.g. livestock) or otherwise subject to human care and/or maintenance (e.g. zoo animals and other animals for exhibition). In other non-limiting examples, the terms refer to ruminants or carnivores, such as dogs, cats, birds, horses, cattle, sheep, goats, marine animals and mammals, penguins, deer, elk, and foxes.

The term "PDE agent" as used herein includes a neurogenic agent, as defined herein, that elicits an observable response upon contacting a PDE, including one or more of the known isozymes. "PDE agents" useful in the methods described herein include compounds or agents that, under certain conditions, may act as modulators or inhibitors of PDE activity (able to modulator or inhibit one or more characteristic activities of a PDE, for example, by competitively or non-competitively binding to the PDE, a ligand of PDE, and/or a downstream signaling molecule).

The term "PDE inhibitor" refers generally to a neurogenic agent, as disclosed herein, that decreases PDE activity relative to PDE activity in the absence of the agent. In some embodiments, PDE activity is reduced by at least about 50%, or at least about 75%, or at least about 90%. In further embodiments, PDE activity is reduced by at least about 95%, or by at least about 99%. PDE inhibitors useful in methods described herein may act as competitive inhibitors, non-competitive inhibitors, allosteric inhibitors, and/or any mechanism that inhibits a target PDE activity.

In various embodiments, a PDE agent may act directly against a PDE, or indirectly in connection with a co-factor, substrate, or other molecule. For example, some PDE isozymes are subject to allosteric regulation by endogenous activators and/or inhibitors, wherein binding of an allosteric regulator modulates enzymatic activity. Examples of PDEs subject to allosteric regulation include PDE1, which is allosterically activated by $Ca^{2+}$/calmodulin, and PDE2 and PDE5, which are allosterically activated by cGMP. Allosteric regulators often modulate the susceptibility of PDEs to inhibition with particular inhibitors. For example, binding of cGMP to the allosteric site of PDE5 enhances binding of PDE5 inhibitors, such as sildenafil. Thus, in some embodiments, a PDE agent is administered in conjunction with an allosteric regulator of the target PDE, or an agent that modulates the activity and/or levels of an endogenous allosteric regulator of the target PDE (e.g., calcium-channel modulators, cyclic nucleotide cyclase activators). Methods for detecting allosteric binding to PDEs are described, e.g., in Weeks et al., Methods Mol. Biol. 2005; 307:239-62. In some embodiments, a PDE agent may modulate the activity of a PDE in response to another compound or treatment modality.

In other embodiments, the PDE agent(s) used in the methods described herein has "selective" activity under certain conditions against one or more PDE isozymes with respect to the degree and/or nature of activity against one or more other PDE isozymes. In certain embodiments, selective activity of one or more PDE agents results in enhanced efficacy, fewer side effects, lower effective dosages, less frequent dosing, or other desirable attributes.

The terms "cGMP-specific PDE" and "cAMP-specific PDE" refer to PDEs that specifically and/or preferentially hydrolyze cGMP or cAMP, respectively. In some embodiments, a PDE preferentially or specifically hydrolyzes a particular cyclic nucleotide if the $K_m$ for the non-preferred substrate nucleotide is 2-fold, 5-fold, 10-fold, 20-fold, 50-fold, or greater than the $K_m$ for the preferred substrate. For example, PDE4, which is selective for cAMP, has an approximately 1000-fold greater $K_m$ for cGMP than cAMP, whereas PDE5, which is selective for cGMP, has an approximately 100-fold greater $K_m$ for cAMP than cGMP. In some embodiments, a PDE preferentially or specifically hydrolyzes a particular cyclic nucleotide if the $V_{max}$ for the preferred substrate nucleotide is 2-fold, 5-fold, 10-fold, 20-fold, 50-fold, or greater than the $V_{max}$ for the non-preferred substrate. For example, PDE3, which preferentially hydrolyzes cAMP, has a substantially similar $K_m$ for cAMP and cGMP, but has an approximately 5-fold greater $V_{max}$ for cAMP. In some embodiments, a PDE specifically/preferentially hydrolyzes cAMP or cGMP due to other and/or additional factors, such as the localization of the PDE in the cell, the interaction of the PDE with endogenous regulators, etc. The term "dual-specificity PDE" refers generally to a PDE capable of hydrolyzing both cAMP and cGMP under physiologically relevant conditions. Generally, PDE1, PDE2, PDE10, and PDE11 are dual-specificity PDEs, PDE3, PDE4, and PDE8 are cAMP-specific PDEs, and PDE5, PDE6, and PDE9 are cGMP-specific PDEs. The substrate-specificities of PDEs may vary according to a number of factors, such as the conditions under which they are determined, species differences, tissue-specific or disease-specific isoforms/splice variants, and the like. Thus, the above definitions are not intended to be universally applicable.

In some embodiments, the PDE agent(s) used in the methods described herein are substantially inactive with respect to other receptors (i.e., non-PDE), such as muscarinic receptors, 5-HT receptors, dopamine receptors, epinephrine receptors, histamine receptors, glutamate receptors, and the like. However, in other embodiments, PDE agent(s) are active against one or more additional receptor subtypes.

In additional embodiments, a PDE agent as used herein includes a neurogenesis modulating agent, as defined herein, that elicits an observable neurogenic response by producing, generating, stabilizing, or increasing the retention of an intermediate agent which, when contacted with a PDE, results in the neurogenic response. As used herein, "increasing the retention of" or variants of that phrase or the term "retention" refer to decreasing the degradation of, or increasing the stability of, an intermediate agent.

In some cases, a PDE agent, optionally in combination with one or more other neurogenic agents, results in improved efficacy, fewer side effects, lower effective dosages, less frequent dosing, and/or other desirable effects relative to use of the neurogenesis modulating agents individually (such as at higher doses), due, e.g., to synergistic activities and/or the targeting of molecules and/or activities that are differentially expressed in particular tissues and/or cell-types.

The term "neurogenic combination of a PDE agent with one or more other neurogenic agents" refers to a combination of neurogenesis modulating agents. In some embodiments, administering a neurogenic, or neuromodulating, combination according to methods provided herein modulates neurogenesis in a target tissue and/or cell-type by at least about 50%, at least about 75%, or at least about 90% or more in comparison to the absence of the combination. In further embodiments, neurogenesis is modulated by at least about 95% or by at least about 99% or more.

A neuromodulating combination may be used to inhibit a neural cell's proliferation, division, or progress through the cell cycle. Alternatively, a neuromodulating combination may be used to stimulate survival and/or differentiation in a neural cell. As an additional alternative, a neuromodulating combination may be used to inhibit, reduce, or prevent astrocyte activation and/or astrogenesis or astrocyte differentiation.

"$IC_{50}$" refers to the concentration of a PDE inhibitor that reduces the activity of the PDE to half-maximal level. $IC_{50}$ values, as described herein, can be determined using in vitro assays (e.g., cell-free assays) or cell-based assays. Without being bound by theory, and offered to improve the understanding of the disclosure, cell-free assays generally detect compounds that exert their effect directly on a PDE activity and/or required co-factors, whereas cell-based assays detect compounds that exert effects directly and/or indirectly. Assays for determining and quantifying inhibitory activity against various PDE activities are known in the art and, are described, e.g., in U.S. Pat. Nos. 6,348,602, 5,932,465, US20030190672, US20020115176, US20040018542, US20050009062, Loughney et al., J. Biol. Chem., 271, pp. 796-806 (1996), Thompson et al., Biochemistry 10: 311-316 (1971), Kincaid et al., J Biol. Chem., 259(8):5158-66 (1984), Davis et al., Biochim. Biophys. Acta 797, 354-362 (1984) and Kincaid et al., Methods Enzymol., 159:457-70 (1988), all of which are herein incorporated by reference. PDE activity can be assayed in vivo, for example as described in Rich et al., J. Gen. Physiology, 118(1); 63-78 (2001), herein incorporated by reference.

PDE inhibitors used in methods described herein preferably have $IC_{50}$ values with respect to one or more target PDE activities residing in the CNS of less than about 10 µM, or less than about 1 µM, or less than about 0.1 µM. In some embodiments, the PDE inhibitor has an $IC_{50}$ of less than about 50 µM, or less than about 10 µM, or less than about 1 µM. In some embodiments, administration of a PDE inhibitor according to methods described herein reduces PDE activity within a target tissue by at least about 50%, or at least about 75%, or at least about 90%. In further embodiments, PDE activity is reduced by at least about 95% or by at least about 99%. In some embodiments, the PDE inhibitor has the desired activity at a concentration that is lower than the concentration of the inhibitor that is required to produce another, unrelated biological effect. In some exemplary embodiments, the concentration of the inhibitor required for PDE inhibitory activity is at least about 2-fold lower, or at least about 5-fold lower, or at least about 10-fold lower, or at least about 20-fold lower than the concentration required to produce an unrelated biological effect.

Isozyme-selectivity can be measured as the ratio of $IC_{50}$ for a target PDE:$IC_{50}$ for a non-target PDE. Methods for determining isozyme-selectivity are known in the art, and are described, e.g., in Weeks et al., Int J Impot Res. 2005 January-February; 17(1):5-9 and Gupta et al., Methods Find Exp Clin Pharmacol. 2005 March; 27(2):101-18. In some embodiments, a "isozyme-selective" PDE agent has an isozyme selectivity that is less than about 1:2, or less than about 1:5, or less than about 1:10, or less than about 1:50. In further embodiments, the isozyme-selective activity of a PDE agent used in methods described herein results in improved efficacy, fewer side effects, lower effective dosages, less frequent dosing, and/or other desirable attributes relative to non-selective inhibitors, due, e.g., to targeting of tissue and/or cell-specific PDE isozymes.

"$IC_{50}$" and "$EC_{50}$" values also refer to concentrations of an agent, in a combination of a PDE agent with one or more other neurogenic agents, that reduce and promote, respectively, neurogenesis or another physiological activity (e.g., the activity of a receptor) to a half-maximal level. $IC_{50}$ and $EC_{50}$ values can be assayed in a variety of environments, including cell-free environments, cellular environments (e.g., cell culture assays), multicellular environments (e.g., in tissues or other multicellular structures), and/or in vivo. In some embodiments, one or more neurogenesis modulating agents in a combination or method disclosed herein individually have $IC_{50}$ or $EC_{50}$ values of less than about 10 µM, less than about 1 µM, or less than about 0.1 µM or lower. In other embodiments, an agent in a combination has an $IC_{50}$ of less than about 50 nM, less than about 10 nM, or less than about 1 nM or lower.

In some embodiments, selectivity of one or more agents, in a combination of a PDE agent with one or more other neurogenic agents, is individually measured as the ratio of the $IC_{50}$ or $EC_{50}$ value for a desired effect (e.g., modulation of neurogenesis) relative to the $IC_{50}$ or $EC_{50}$ value for an undesired effect. In some embodiments, a "selective" agent in a combination has a selectivity of less than about 1:2, less than about 1:10, less than about 1:50, or less than about 1:100. In some embodiments, one or more agents in a combination individually exhibits selective activity in one or more organs, tissues, and/or cell types relative to another organ, tissue, and/or cell type. For example, in some embodiments, an agent in a combination selectively modulates neurogenesis in a neurogenic region of the brain, such as the hippocampus (e.g., the dentate gyrus), the subventricular zone, and/or the olfactory bulb.

In other embodiments, modulation by a combination of agents is in a region containing neural cells affected by disease or injury, region containing neural cells associated with disease effects or processes, or region containing neural cells affect other event injurious to neural cells. Non-limiting examples of such events include stroke or radiation therapy of the region. In additional embodiments, a neuromodulating combination substantially modulates two or more physiological activities or target molecules, while being substantially inactive against one or more other molecules and/or activities.

The term "cognitive function" refers to mental processes of an animal or human subject relating to information gathering and/or processing; the understanding, reasoning, and/or application of information and/or ideas; the abstraction or specification of ideas and/or information; acts of creativity, problem-solving, and possibly intuition; and mental processes such as learning, perception, and/or awareness of ideas and/or information. The mental processes are distinct from those of beliefs, desires, and the like. In some embodiments, cognitive function may be assessed, and thus optionally defined, via one or more tests or assays for cognitive function. Non-limiting examples of a test or assay for cognitive function include CANTAB (see for example Fray et al. "CANTAB battery: proposed utility in neurotoxicology." *Neurotoxicol Teratol.* 1996; 18(4):499-504), Stroop Test, Trail Making, Wechsler Digit Span, or the CogState computerized cognitive test (see also Dehaene et al. "Reward-dependent learning in neuronal networks for planning and decision making." *Prog Brain Res.* 2000; 126:217-29; Iverson et al. "Interpreting change on the WAIS-III/WMS-III in clinical samples." *Arch Clin Neuropsychol.* 2001; 16(2):183-91; and Weaver et al. "Mild memory impairment in healthy older adults is distinct from normal aging." *Brain Cogn.* 2006; 60(2):146-55).

DETAILED DESCRIPTION OF MODES OF PRACTICING THE DISCLOSURE

General

Methods described herein can be used to treat any disease or condition for which it is beneficial to promote or otherwise stimulate or increase neurogenesis. One focus of the methods described herein is to achieve a therapeutic result by stimulating or increasing neurogenesis via modulation of PDE activity. Thus, certain methods described herein can be used to treat any disease or condition susceptible to treatment by increasing neurogenesis.

In some embodiments, a disclosed method is applied to modulating neurogenesis in vivo, in vitro, or ex vivo. In in vivo embodiments, the cells may be present in a tissue or organ of a subject animal or human being. Non-limiting examples of cells include those capable of neurogenesis, such as to result, whether by differentiation or by a combination of differentiation and proliferation, in differentiated neural cells. As described herein, neurogenesis includes the differentiation of neural cells along different potential lineages. In some embodiments, the differentiation of neural stem or progenitor cells is along a neuronal cell lineage to produce neurons. In other embodiments, the differentiation is along both neuronal and glial cell lineages. In additional embodiments, the disclosure further includes differentiation along a neuronal cell lineage to the exclusion of one or more cell types in a glial cell lineage. Non-limiting examples of glial cell types include oligodendrocytes and radial glial cells, as well as astrocytes, which have been reported as being of an "astroglial lineage". Therefore, embodiments of the disclosure include differentiation along a neuronal cell lineage to the exclusion of one or more cell types selected from oligodendrocytes, radial glial cells, and astrocytes.

In applications to an animal or human being, the disclosure includes a method of bringing cells into contact with a PDE agent, optionally in combination with one or more other neurogenic agents, in effective amounts to result in an increase in neurogenesis in comparison to the absence of the agent or combination. A non-limiting example is in the administration of the agent or combination to the animal or human being. Such contacting or administration may also be described as exogenously supplying the combination to a cell or tissue.

Embodiments of the disclosure include a method to treat, or lessen the level of, a decline or impairment of cognitive function. Also included is a method to treat a mood disorder. In additional embodiments, a disease or condition treated with a disclosed method is associated with pain and/or addiction, but in contrast to known methods, the disclosed treatments are substantially mediated by increasing neurogenesis. As a further non-limiting example, a method described herein may involve increasing neurogenesis ex vivo, such that a composition containing neural stem cells, neural progenitor cells, and/or differentiated neural cells can subsequently be administered to an individual to treat a disease or condition.

In further embodiments, methods described herein allow treatment of diseases characterized by pain, addiction, and/or depression by directly replenishing, replacing, and/or supplementing neurons and/or glial cells. In further embodiments, methods described herein enhance the growth and/or survival of existing neural cells, and/or slow or reverse the loss of such cells in a neurodegenerative condition.

Where a method comprises contacting a neural cell with a PDE agent, the result may be an increase in neurodifferentiation. The method may be used to potentiate a neural cell for proliferation, and thus neurogenesis, via the one or more other agents used with the PDE agent in combination. Thus the disclosure includes a method of maintaining, stabilizing, stimulating, or increasing neurodifferentiation in a cell or tissue by use of a PDE agent, optionally in combination with one or more other neurogenic agents that also increase neurodifferentiation. The method may comprise contacting a cell or tissue with a PDE agent, optionally in combination with one or more other neurogenic agents, to maintain, stabilize stimulate, or increase neurodifferentiation in the cell or tissue.

The disclosure also includes a method comprising contacting the cell or tissue with a PDE agent in combination with one or more other neurogenic agents where the combination stimulates or increases proliferation or cell division in a neural cell. The increase in neuroproliferation may be due to the one or more other neurogenic agents and/or to the PDE agent. In some cases, a method comprising such a combination may be used to produce neurogenesis (in this case both neurodifferentiation and/or proliferation) in a population of neural cells. In some embodiments, the cell or tissue is in an animal subject or a human patient as described herein. Non-limiting examples include a human patient treated with chemotherapy and/or radiation, or other therapy or condition which is detrimental to cognitive function; or a human patient diagnosed as having epilepsy, a condition associated with epilepsy, or seizures associated with epilepsy.

Administration of a PDE agent, optionally in combination with one or more other neurogenic agents, may be before, after, or concurrent with, another agent, condition, or therapy. In some embodiments, the overall combination may be of a PDE agent, optionally in combination with one or more other neurogenic agents.

Uses of a PDE Agent

Embodiments of a first aspect of the disclosure include a method of modulating neurogenesis by contacting one or more neural cells with a PDE agent, optionally in combination with one or more other neurogenic agents. The amount of a PDE agent, or a combination thereof with one or more other neurogenic agents, may be selected to be effective to produce an improvement in a treated subject, or detectable neurogenesis in vitro. In some embodiments, the amount is one that also minimizes clinical side effects seen with administration of the inhibitor to a subject.

Without being bound by theory, and offered to improve the understanding of the disclosure, phosphodiesterase inhibition is believed to promote neurogenesis by targeting second messenger systems downstream of neurotransmitters and other signaling molecules. Cyclic adenosine monophosphate (cAMP) and cyclic guanosine monophosphate (cGMP) are both examples of such second messengers, and inhibition of PDEs may prolong cAMP and cGMP signals and may increase signaling through neurogenic signal transduction pathways Cognitive Function In other embodiments, and if compared to a reduced level of cognitive function, a method of the invention may be for enhancing or improving the reduced cognitive function in a subject or patient. The method may comprise administering a PDE agent, optionally in combination with one or more other neurogenic agents, to a subject or patient to enhance or improve a decline or decrease of cognitive function due to a therapy and/or condition that reduces cognitive function. Other methods of the disclosure include treatment to affect or maintain the cognitive function of a subject or patient. In some embodiments, the maintenance or stabilization of cognitive function may be at a level, or thereabouts, present in a subject or patient in the absence of a therapy and/or condition that reduces cognitive function. In alternative embodiments, the maintenance or stabilization may be at a level, or thereabouts, present in a subject or patient as a result of a therapy and/or condition that reduces cognitive function.

In further embodiments, and if compared to a reduced level of cognitive function due to a therapy and/or condition that reduces cognitive function, a method of the invention may be for enhancing or improving the reduced cognitive function in a subject or patient. The method may comprise administering a PDE agent, or a combination thereof with one or more other neurogenic agents, to a subject or patient to enhance or improve a decline or decrease of cognitive function due to the therapy or condition. The administering may be in combination with the therapy or condition.

These methods optionally include assessing or measuring cognitive function of the subject or patient before, during, and/or after administration of the treatment to detect or determine the effect thereof on cognitive function. So in one embodiment, a methods may comprise i) treating a subject or patient that has been previously assessed for cognitive function and ii) reassessing cognitive function in the subject or patient during or after the course of treatment. The assessment may measure cognitive function for comparison to a control or standard value (or range) in subjects or patients in the absence of a PDE agent, or a combination thereof with one or more other neurogenic agents. This may be used to assess the efficacy of the PDE agent, alone or in a combination, in alleviating the reduction in cognitive function.

Mood Disorders

In other embodiments, a disclosed method may be used to moderate or alleviate a mood disorder in a subject or patient as described herein. Thus the disclosure includes a method of treating a mood disorder in such a subject or patient. Non-limiting examples of the method include those comprising administering a PDE agent, or a combination thereof with one or more other neurogenic agents, to a subject or patient that is under treatment with a therapy and/or condition that results in a mood disorder. The administration may be with any combination and/or amount that is effective to produce an improvement in the mood disorder.

Representative and non-limiting mood disorders are described herein. Non-limiting examples of mood disorders include depression, anxiety, hypomania, panic attacks, excessive elation, seasonal mood (or affective) disorder, schizophrenia and other psychoses, lissencephaly syndrome, anxiety syndromes, anxiety disorders, phobias, stress and related syndromes, aggression, non-senile dementia, post-pain depression, and combinations thereof.

Identification of Subjects and Patients

The disclosure includes methods comprising identification of an individual suffering from one or more disease, disorders, or conditions, or a symptom thereof, and administering to the subject or patient a PDE agent, optionally in combination with one or more other neurogenic agents, as described herein. The identification of a subject or patient as having one or more diseases, disorders or conditions, or a symptom thereof, may be made by a skilled practitioner using any appropriate means known in the field. The disclosure also includes identification or diagnosis of a subject or patient as having one or more diseases, disorders or conditions, or a symptom thereof, which is suitably or beneficially treated or addressed by increasing neurogenesis in the subject or patient.

The subsequent administration of a PDE agent, alone or in combination as described herein may be based on, or as directed by, the identification or diagnosis of a subject or patient as in need of one or more effects provided by a PDE agent or a combination. Non-limiting examples of an effect include neurogenic activity and/or potentiation of neurogenesis.

In some embodiments, identification of a patient in need of neurogenesis modulation comprises identifying a patient who has or will be exposed to a factor or condition known to inhibit neurogenesis, including but not limited to, stress, aging, sleep deprivation, hormonal changes (e.g., those associated with puberty, pregnancy, or aging (e.g., menopause), lack of exercise, lack of environmental stimuli (e.g., social isolation), diabetes and drugs of abuse (e.g., alcohol, especially chronic use; opiates and opioids; psychostimulants). In some cases, the patient has been identified as non-responsive to treatment with primary medications for the condition(s) targeted for treatment (e.g., non-responsive to antidepressants for the treatment of depression), and a PDE agent, optionally in combination with one or more other neurogenic agents, is administered in a method for enhancing the responsiveness of the patient to a co-existing or pre-existing treatment regimen.

In other embodiments, the method or treatment comprises administering a combination of a primary medication or therapy for the condition(s) targeted for treatment and a PDE agent, optionally in combination with one or more other neurogenic agents. For example, in the treatment of depression or related neuropsychiatric disorders, a combination may be administered in conjunction with, or in addition to, electroconvulsive shock treatment, a monoamine oxidase modulator, and/or a selective reuptake modulators of serotonin and/or norepinephrine.

In additional embodiments, the patient in need of neurogenesis modulation suffers from premenstrual syndrome, post-partum depression, or pregnancy-related fatigue and/or depression, and the treatment comprises administering a therapeutically effective amount of a PDE agent, optionally in combination with one or more other neurogenic agents. Without being bound by any particular theory, and offered to improve understanding of the invention, it is believed that levels of steroid hormones, such as estrogen, are increased during the menstrual cycle during and following pregnancy, and that such hormones can exert a modulatory effect on neurogenesis.

In some embodiments, the patient is a user of a recreational drug including but not limited to alcohol, amphetamines, PCP, cocaine, and opiates. Without being bound by any particular theory, and offered to improve understanding of the invention, it is believed that some drugs of abuse have a modulatory effect on neurogenesis, which is associated with depression, anxiety and other mood disorders, as well as deficits in cognition, learning, and memory. Moreover, mood disorders are causative/risk factors for substance abuse, and substance abuse is a common behavioral symptom (e.g., self medicating) of mood disorders. Thus, substance abuse and mood disorders may reinforce each other, rendering patients suffering from both conditions non-responsive to treatment. Thus, in some embodiments, a PDE agent, optionally in combination with one or more other neurogenic agents, to treat patients suffering from substance abuse and/or mood disorders. In additional embodiments, the PDE agent, optionally in combination with one or more other neurogenic agents, can used in combination with one or more additional agents selected from an antidepressant, an antipsychotic, a mood stabilizer, or any other agent known to treat one or more symptoms exhibited by the patient. In some embodiments, a PDE agent exerts a synergistic effect with the one or more additional agents in the treatment of substance abuse and/or mood disorders in patients suffering from both conditions.

In further embodiments, the patient is on a co-existing and/or pre-existing treatment regimen involving administration of one or more prescription medications having a modulatory effect on neurogenesis. For example, in some embodiments, the patient suffers from chronic pain and is prescribed one or more opiate/opioid medications; and/or suffers from ADD, ADHD, or a related disorder, and is prescribed a psychostimulant, such as ritalin, dexedrine, adderall, or a similar medication which inhibits neurogenesis. Without being bound by any particular theory, and offered to improve understanding of the invention, it is believed that such medications can exert a modulatory effect on neurogenesis, leading to depression, anxiety and other mood disorders, as well as deficits in cognition, learning, and memory. Thus, in some preferred embodiments, a PDE agent, optionally in combination with one or more other neurogenic agents, is administered to a patient who is currently or has recently been prescribed a medication that exerts a modulatory effect on neurogenesis, in order to treat depression, anxiety, and/or other mood disorders, and/or to improve cognition.

In additional embodiments, the patient suffers from chronic fatigue syndrome; a sleep disorder; lack of exercise (e.g., elderly, infirm, or physically handicapped patients); and/or lack of environmental stimuli (e.g., social isolation); and the treatment comprises administering a therapeutically effective amount of a PDE agent, optionally in combination with one or more other neurogenic agents.

In more embodiments, the patient is an individual having, or who is likely to develop, a disorder relating to neural degeneration, neural damage and/or neural demyelination.

In further embodiments, a subject or patient includes human beings and animals in assays for behavior linked to neurogenesis. Exemplary human and animal assays are known to the skilled person in the field.

In yet additional embodiments, identifying a patient in need of neurogenesis modulation comprises selecting a population or sub-population of patients, or an individual patient, that is more amenable to treatment and/or less susceptible to side effects than other patients having the same disease or condition. In some embodiments, identifying a patient amenable to treatment with a PDE agent, optionally in combination with one or more other neurogenic agents, comprises identifying a patient who has been exposed to a factor known to enhance neurogenesis, including but not limited to, exercise, hormones or other endogenous factors, and drugs taken as part of a pre-existing treatment regimen. In some embodiments, a sub-population of patients is identified as being more amenable to neurogenesis modulation with a PDE agent, optionally in combination with one or more other neurogenic agents, by taking a cell or tissue sample from prospective patients, isolating and culturing neural cells from the sample, and determining the effect of the combination on the degree or nature of neurogenesis of the cells, thereby allowing selection of patients for which the therapeutic agent has a substantial effect on neurogenesis. Advantageously, the selection of a patient or population of patients in need of or amenable to treatment with a PDE agent, optionally in combination with one or more other neurogenic agents, of the disclosure allows more effective treatment of the disease or condition targeted for treatment than known methods using the same or similar compounds.

In some embodiments, the patient has suffered a CNS insult, such as a CNS lesion, a seizure (e.g., electroconvulsive seizure treatment; epileptic seizures), radiation, chemotherapy and/or stroke or other ischemic injury. Without being bound by any particular theory, and offered to improve understanding of the invention, it is believed that some CNS insults/injuries leads to increased proliferation of neural stem cells, but that the resulting neural cells form aberrant connections which can lead to impaired CNS function and/or diseases, such as temporal lobe epilepsy. In other embodiments, a PDE agent, optionally in combination with one or more other neurogenic agents, is administered to a patient who has suffered, or is at risk of suffering, a CNS insult or injury to stimulate neurogenesis. Advantageously, stimulation of the differentiation of neural stem cells with a PDE agent, optionally in combination with one or more other neurogenic agents, activates signaling pathways necessary for progenitor cells to effectively migrate and incorporate into existing neural networks or to block inappropriate proliferation.

Opiate or Opioid Based Analgesic

Additionally, the disclosed methods provide for the application of a PDE agent, optionally in combination with one or more other neurogenic agents, to treat a subject or patient for a condition due to the anti-neurogenic effects of an opiate or opioid based analgesic. In some embodiments, the administration of an opiate or opioid based analgesic, such as an opiate like morphine or other opioid receptor agonist, to a subject or patient results in a decrease in, or inhibition of, neurogenesis. The administration of a PDE agent, optionally in combination with one or more other neurogenic agents, with an opiate or opioid based analgesic would reduce the anti-neurogenic effect. One non-limiting example is administration of such a combination with an opioid receptor agonist after surgery (such as for the treating post-operative pain).

So the disclosed embodiments include a method of treating post operative pain in a subject or patient by combining administration of an opiate or opioid based analgesic with a PDE agent, optionally in combination with one or more other neurogenic agents. The analgesic may have been administered before, simultaneously with, or after the combination. In some cases, the analgesic or opioid receptor agonist is morphine or another opiate.

Other disclosed embodiments include a method to treat or prevent decreases in, or inhibition of, neurogenesis in other cases involving use of an opioid receptor agonist. The methods comprise the administration of a PDE agent, optionally in combination with one or more other neurogenic agents, as described herein. Non-limiting examples include cases involving an opioid receptor agonist, which decreases or inhibits neurogenesis, and drug addiction, drug rehabilitation, and/or prevention of relapse into addiction. In some embodiments, the opioid receptor agonist is morphine, opium or another opiate.

In further embodiments, the disclosure includes methods to treat a cell, tissue, or subject which is exhibiting decreased neurogenesis or increased neurodegeneration. In some cases, the cell, tissue, or subject is, or has been, subjected to, or contacted with, an agent that decreases or inhibits neurogenesis. One non-limiting example is a human subject that has been administered morphine or other agent which decreases or inhibits neurogenesis. Non-limiting examples of other agents include opiates and opioid receptor agonists, such as mu receptor subtype agonists, that inhibit or decrease neurogenesis.

Thus in additional embodiments, the methods may be used to treat subjects having, or diagnosed with, depression or other withdrawal symptoms from morphine or other agents which decrease or inhibit neurogenesis. This is distinct from the treatment of subjects having, or diagnosed with, depression independent of an opiate, such as that of a psychiatric nature, as disclosed herein. In further embodiments, the methods may be used to treat a subject with one or more chemical addictions or dependencies, such as with morphine or other opiates, where the addiction or dependency is ameliorated or alleviated by an increase in neurogenesis.

Transplantation

In other embodiments, methods described herein involve modulating neurogenesis in vitro or ex vivo with a PDE agent, optionally in combination with one or more other neurogenic agents, such that a composition containing neural stem cells, neural progenitor cells, and/or differentiated neural cells can subsequently be administered to an individual to treat a disease or condition. In some embodiments, the method of treatment comprises the steps of contacting a neural stem cell or progenitor cell with a PDE agent, optionally in combination with one or more other neurogenic agents, to modulate neurogenesis, and transplanting the cells into a patient in need of treatment. Methods for transplanting stem and progenitor cells are known in the art, and are described, e.g., in U.S. Pat. Nos. 5,928,947; 5,817,773; and 5,800,539, and PCT Publication Nos. WO 01/176507 and WO 01/170243, all of which are incorporated herein by reference in their entirety. In some embodiments, methods described herein allow treatment of diseases or conditions by directly replenishing, replacing, and/or supplementing damaged or dysfunctional neurons. In further embodiments, methods described herein enhance the growth and/or survival of existing neural cells, and/or slow or reverse the loss of such cells in a neurodegenerative or other condition.

In alternative embodiments, the method of treatment comprises identifying, generating, and/or propagating neural cells in vitro or ex vivo in contact with a PDE agent, optionally in combination with one or more other neurogenic agents, and transplanting the cells into a subject. In another embodiment, the method of treatment comprises the steps of contacting a neural stem cell of progenitor cell with a PDE agent, optionally in combination with one or more other neurogenic agents, to stimulate neurogenesis or neurodifferentiation, and transplanting the cells into a patient in need of treatment. Also disclosed are methods for preparing a population of neural stem cells suitable for transplantation, comprising culturing a population of neural stem cells (NSCs) in vitro, and contacting the cultured neural stem cells with a PDE agent, optionally in combination with one or more other neurogenic agents, as described herein. The disclosure further includes methods of treating the diseases, disorders, and conditions described herein by transplanting such treated cells into a subject or patient.

Neurogenesis with Angiogenesis

In additional embodiments, the disclosure includes a method of stimulating or increasing neurogenesis in a subject or patient with stimulation of angiogenesis in the subject or patient. The co-stimulation may be used to provide the differentiating and/or proliferating cells with increased access to the circulatory system. The neurogenesis is produced by modulation of PDE activity, such as with a PDE agent, optionally in combination with one or more other neurogenic agents, as described herein. An increase in angiogenesis may be mediated by a means known to the skilled person, including administration of a angiogenic factor or treatment with an angiogenic therapy. Non-limiting examples of angiogenic factors or conditions include vascular endothelial growth factor (VEGF), angiopoietin-1 or -2, erythropoietin, exercise, or a combination thereof.

So in some embodiments, the disclosure includes a method comprising administering i) a PDE agent, optionally in combination with one or more other neurogenic agents, and ii) one or more angiogenic factors to a subject or patient. In other embodiments, the disclosure includes a method comprising administering i) a PDE agent, optionally in combination with one or more other neurogenic agents, to a subject or patient with ii) treating said subject or patient with one or more angiogenic conditions. The subject or patient may be any as described herein.

The co-treatment of a subject or patient includes simultaneous treatment or sequential treatment as non-limiting examples. In cases of sequential treatment, the administration of a PDE agent, optionally with one or more other neurogenic agents, may be before or after the administration of an angiogenic factor or condition. Of course in the case of a combination of a PDE agent and one or more other neurogenic agents, the PDE agent may be administered separately from the one or more other agents, such that the one or more other agents administered before or after administration of an angiogenic factor or condition.

Additional Diseases and Conditions

As described herein, the disclosed embodiments include methods of treating diseases, disorders, and conditions of the central and/or peripheral nervous systems (CNS and PNS, respectively) by administering a PDE agent, optionally in combination with one or more other neurogenic agents. As used herein, "treating" includes prevention, amelioration, alleviation, and/or elimination of the disease, disorder, or condition being treated or one or more symptoms of the disease, disorder, or condition being treated, as well as improvement in the overall well being of a patient, as measured by objective and/or subjective criteria. In some embodiments, treating is used for reversing, attenuating, minimizing, suppressing, or halting undesirable or deleterious effects of, or effects from the progression of, a disease, disorder, or condition of the central and/or peripheral nervous systems. In other embodiments, the method of treating may be advantageously used in cases where additional neurogenesis would replace, replenish, or increase the numbers of cells lost due to injury or disease as non-limiting examples.

The amount of a PDE agent, optionally in combination with one or more other neurogenic agents may be any that results in a measurable relief of a disease condition like those described herein. As a non-limiting example, an improvement in the Hamilton depression scale (HAM-D) score for depression may be used to determine (such as quantitatively) or detect (such as qualitatively) a measurable level of improvement in the depression of a subject.

Non-limiting examples of symptoms that may be treated with the methods described herein include abnormal behavior, abnormal movement, hyperactivity, hallucinations, acute delusions, combativeness, hostility, negativism, withdrawal, seclusion, memory defects, sensory defects, cognitive defects, and tension. Non-limiting examples of abnormal behavior include irritability, poor impulse control, distractibility, and aggressiveness. Outcomes from treatment with the disclosed methods include improvements in cognitive function or capability in comparison to the absence of treatment.

Additional examples of diseases and conditions treatable by the methods described herein include, but are not limited to, neurodegenerative disorders and neural disease, such as dementias (e.g., senile dementia, memory disturbances/memory loss, dementias caused by neurodegenerative disorders (e.g., Alzheimer's, Parkinson's disease, Parkinson's disorders, Huntington's disease (Huntington's Chorea), Lou Gehrig's disease, multiple sclerosis, Pick's disease, Parkinsonism dementia syndrome), progressive subcortical gliosis, progressive supranuclear palsy, thalmic degeneration syndrome, hereditary aphasia, amyotrophic lateral sclerosis, Shy-Drager syndrome, and Lewy body disease; vascular conditions (e.g., infarcts, hemorrhage, cardiac disorders); mixed vascular and Alzheimer's; bacterial meningitis; Creutzfeld-Jacob Disease; and Cushing's disease.

The disclosed embodiments also provide for the treatment of a nervous system disorder related to neural damage, cellular degeneration, a psychiatric condition, cellular (neurological) trauma and/or injury (e.g., subdural hematoma or traumatic brain injury), toxic chemicals (e.g., heavy metals, alcohol, some medications), CNS hypoxia, or other neurologically related conditions. In practice, the disclosed compositions and methods may be applied to a subject or patient afflicted with, or diagnosed with, one or more central or peripheral nervous system disorders in any combination. Diagnosis may be performed by a skilled person in the applicable fields using known and routine methodologies which identify and/or distinguish these nervous system disorders from other conditions.

Non-limiting examples of nervous system disorders related to cellular degeneration include neurodegenerative disorders, neural stem cell disorders, neural progenitor cell disorders, degenerative diseases of the retina, and ischemic disorders. In some embodiments, an ischemic disorder comprises an insufficiency, or lack, of oxygen or angiogenesis, and non-limiting example include spinal ischemia, ischemic stroke, cerebral infarction, multi-infarct dementia. While these conditions may be present individually in a subject or patient, the disclosed methods also provide for the treatment of a subject or patient afflicted with, or diagnosed with, more than one of these conditions in any combination.

Non-limiting embodiments of nervous system disorders related to a psychiatric condition include neuropsychiatric disorders and affective disorders. As used herein, an affective disorder refers to a disorder of mood such as, but not limited to, depression, post-traumatic stress disorder (PTSD), hypomania, panic attacks, excessive elation, bipolar depression, bipolar disorder (manic-depression), and seasonal mood (or affective) disorder. Other non-limiting embodiments include schizophrenia and other psychoses, lissencephaly syndrome, anxiety syndromes, anxiety disorders, phobias, stress and related syndromes (e.g., panic disorder, phobias, adjustment disorders, migraines), cognitive function disorders, aggression, drug and alcohol abuse, drug addiction, and drug-induced neurological damage, obsessive compulsive behavior syndromes, borderline personality disorder, non-senile dementia, post-pain depression, post-partum depression, and cerebral palsy.

Examples of nervous system disorders related to cellular or tissue trauma and/or injury include, but are not limited to, neurological traumas and injuries, surgery related trauma and/or injury, retinal injury and trauma, injury related to epilepsy, cord injury, spinal cord injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxin, and spinal cord injury related to environmental toxin.

Non-limiting examples of nervous system disorders related to other neurologically related conditions include learning disorders, memory disorders, age-associated memory impairment (AAMI) or age-related memory loss, autism, learning or attention deficit disorders (ADD or attention deficit hyperactivity disorder, ADHD), narcolepsy, sleep disorders and sleep deprivation (e.g., insomnia, chronic fatigue syndrome), cognitive disorders, epilepsy, injury related to epilepsy, and temporal lobe epilepsy.

Other non-limiting examples of diseases and conditions treatable by the methods described herein include, but are not limited to, hormonal changes (e.g., depression and other mood disorders associated with puberty, pregnancy, or aging (e.g., menopause)); and lack of exercise (e.g., depression or other mental disorders in elderly, paralyzed, or physically handicapped patients); infections (e.g., HIV); genetic abnormalities (down syndrome); metabolic abnormalities (e.g., vitamin B12 or folate deficiency); hydrocephalus; memory loss separate from dementia, including mild cognitive impairment (MCI), age-related cognitive decline, and memory loss resulting from the use of general anesthetics, chemotherapy, radiation treatment, post-surgical trauma, or therapeutic intervention; and diseases of the of the peripheral nervous system (PNS), including but not limited to, PNS neuropathies (e.g., vascular neuropathies, diabetic neuropathies, amyloid neuropathies, and the like), neuralgias, neoplasms, myelin-related diseases, etc.

Other conditions that can be beneficially treated by increasing neurogenesis are known in the art (see e.g., U.S. Publication Nos. 20020106731, 2005/0009742 and 2005/0009847, 20050032702, 2005/0031538, 2005/0004046, 2004/0254152, 2004/0229291, and 2004/0185429, herein incorporated by reference in their entirety).

PDE Agents

A PDE agent of the disclosure is a ligand which modulates activity of one or more PDE isozymes. In some cases, the ligand may bind or interact with a PDE as an inhibitor. In other cases, the agent may modulate activity indirectly as described herein. In some embodiments, the agent is an inhibitor of one or more isozymes. In additional embodiments, the agent is a blocker or inhibitor of PDE activity.

A PDE agent useful in a method described herein includes an agent that modulates PDE activity at the enzyme level (e.g., by binding directly to PDE), at the transcriptional and/or translational level (e.g., by preventing PDE gene expression), and/or by other modes (e.g., by binding to a substrate or co-factor of PDE, or by modulating the activity of an agent that directly or indirectly modulates PDE activity). For example, in some embodiments, a PDE agent is a compound that modulates the activity of an endogenous PDE inhibitor. The PDE agent can be any, including, but not limited to, a chemical compound, a protein or polypeptide, a peptidomimetic, or an antisense molecule or ribozyme. A number of structurally diverse molecules with PDE inhibitory activity are known in the art. Structures, synthetic processes, safety profiles, biological activity data, methods for determining biological activity, pharmaceutical preparations, and methods of administration for a PDE agent useful in a method described herein are described in the instant text and in the cited references, all of which are herein incorporated by reference in their entirety.

A PDE ligand for use in embodiments of the disclosure includes a non-selective inhibitor, such as ibudilast or MN-166, or dipyridamole (persantine); a PDE1 inhibitor, such as vinpocetine; a PDE3 inhibitor, such as enoximone, milrinone, pimobendan, flosequinan, levosimendan, vesnarinone, olprinone, aminone, inamnirone, anagrelide, cilostazol, or imazodan; a PDE4 inhibitor, such as cilomilast, roflumilast, rolipram, MEM 1414, MEM 1971, NIK 616, GK 07294A, 256066, GW 842470, ONO 6126, PLX369, HT-0712, IPL 455903, IC 485, or NVP-ABE171; or a PDE5 inhibitor, such as revatio, cialis (tadalafil), levitra (vardenafil), DA-8159, dapoxetine, avanafil (TA-1790), SCH-466132, or ABT-670.

In some embodiments, a combination of a PDE ligand and another agent is used in the disclosed compositions, formulations, and methods. One non-limiting example is with a combination of a PDE inhibitor, such as ibudilast, that is not limited to a particular PDE subtype with an ACE inhibitor, an angiotensin receptor antagonist, an HMG-CoA reductase inhibitor, or a vitamin. Non-limiting examples of an ACE inhibitor for use in such a combination include captopril, enalapril, randolapril, or perindopril, while non-limiting examples of an angiotensin receptor antagonist include candesartan or telmisartan. A non-limiting example of an HMG-CoA reductase inhibitor that may be used in such a combination is atorvastatin, while a non-limiting example of a vitamin is folic acid.

In additional embodiments, a combination of the disclosure contains a PDE3 inhibitor, such as enoximone, or a PDE4 inhibitor, such as rolipram and a second agent. Non-limiting examples of the second agent in the combination include an ACE inhibitor, an SSRI, or an agonist of a 5HT1a receptor. Non-limiting examples of an ACE inhibitor include captopril and the other inhibitors described herein, while non-limiting examples of a 5HT1a receptor agonist include busipirone and the other agonists described herein.

In yet additional embodiments, the disclosure includes use of a PDE ligand, alone or in combination with another agent, wherein the ligand affects the activity of more than one PDE isozyme. Stated differently, the ligand may be one which is non-selective in its PDE modulating effect(s). Non-limiting examples of such a ligand include ibudilast and dipyridamole. In some cases, the non-selective ligand is one which exhibits PDE modulating activity, such as inhibitory activity, at PDE5 and one or more other PDE isozymes. In other cases, the non-selective ligand exhibits PDE modulating activity at PDE11 and one or more other PDE isozymes. Non-selective ligands that modulate or inhibit two of more PDE isozymes selected from PDE5, PDE6, PDE8, PDE10, and PDE11, or from PDE1a, PDE2, PDE3, PDE4, PDE5, and PDE11, are included within the scope of the disclosure.

In other embodiments, the PDE inhibitor inhibits a cAMP-specific PDE. Examples of cAMP specific PDE inhibitors useful in the methods described herein include pyrrolidinones, such as the compounds disclosed in U.S. Pat. No. 5,665,754, US20040152754 and US20040023945; quinazolineones, such as the compounds disclosed in U.S. Pat. Nos. 6,747,035, 6,828,315, WO 97/49702 and WO 97/42174; xanthine derivatives; phenylpyridines, such as the compounds disclosed in U.S. Pat. Nos. 6,410,547, 6,090,817, and WO 97/22585; diazepine derivatives, such as the compounds disclosed in WO 97/36905; oxime derivatives, such as the compounds disclosed in U.S. Pat. No. 5,693,659 and WO 96/00215; naphthyridines, such as the compounds described in U.S. Pat. Nos. 5,817,670, 6,740,662, 6,136,821, 6,331,548, 6,297,248, 6,541,480, 6,642,250, 6,900,205, Trifilieff et al., Pharmacology, 301(1): 241-248 (2002) and Hersperger et al., J Med. Chem., 43(4):675-82 (2000); benzofurans, such as the compounds disclosed in U.S. Pat. Nos. 5,902,824, 6,211,203, 6,514,996, 6,716,987, 6,376,535, 6,080,782, 6,054,475, EP 819688, EP685479, and Perrier et al., Bioorg. Med. Chem. Lett. 9:323-326 (1999); phenanthridines, such as those disclosed in U.S. Pat. Nos. 6,191,138, 6,121,279, and 6,127,378; benzoxazoles, such as those disclosed in U.S. Pat. Nos. 6,166,041 and 6,376,485; purine derivatives, such as the compounds disclosed in U.S. Pat. Nos. 6,228,859; benzamides, such as the compounds described in U.S. Pat. Nos. 5,981,527, 5,712,298, WO95/01338, WO 97/48697 and Ashton et al., J. Med Chem 37: 1696-1703 (1994); substituted phenyl compounds, such as the compounds disclosed in U.S. Pat. Nos. 6,297,264, 5,866,593, 655,859,034, 6,245,774, 6,197,792, 6,080,790, 6,077,854, 5,962,483, 5,674,880, 5,786,354, 5,739,144, 5,776,958, 5,798,373, 5,891,896, 5,849,770, 5,550,137, 5,340,827, 5,780,478, 5,780,477, 5,633,257, and WO 95/35283; and substituted biphenyl compounds, such as those disclosed in 5,877,190; quinilinones, such as the compounds described in U.S. Pat. No. 6,800,625 and WO 98/14432.

Additional examples of cAMP-specific PDE inhibitors useful in methods provided herein include compounds disclosed in U.S. Pat. Nos. 6,818,651, 6,737,436, 6,613,778, 6,617,357, 6,146,876, 6,838,559, 6,884,800, 6,716,987, 6,514,996, 6,376,535, 6,740,655, 6,559,168, 6,069,151, 6,365,585, 6,313,116, 6,245,774, 6,011,037, 6,127,363, 6,303,789, 6,316,472, 6,348,602, 6,331,543, 6,333,354, 5,491,147, 5,608,070, 5,622,977, 5,580,888, 6,680,336, 6,569,890, 6,569,885, 6,500,856, 6,486,186, 6,458,787, 6,455,562, 6,444,671, 6,423,710, 6,376,489, 6,372,777, 6,362,213, 6,313,156, 6,294,561, 6,258,843, 6,258,833, 6,121,279, 6,043,263, RE38,624, 6,297,257, 6,251,923, 6,613,794, 6,407,108, 6,107,295, 6,103,718, 6,479,494, 6,602,890, 6,545,158, 6,545,025, 6,498,160, 6,743,802, 6,787,554, 6,828,333, 6,869,945, 6,894,041, 6,924,292, 6,949,573, 6,953,810, 6,156,753, 5,972,927, 5,962,492, 5,814,651, 5,723,460, 5,716,967, 5,686,434, 5,502,072, 5,116,837, 5,091,431; 4,670,434; 4,490,371; 5,710,160, 5,710,170, 6,384,236, 3,941,785, US20050119225, US20050026913, US20050059686, US20040138279, US20050222138, US20040214843, US20040106631, US 20030045557, US 20020198198, US20030162802, US20030092908, US 20030104974, US20030100571, 20030092721, US20050148604, WO 99/65880, WO 00/26201, WO 98/06704, WO 00/59890, WO9907704, WO9422852, WO 98/20007, WO 02/096423, WO 98/18796, WO 98/02440, WO 02/096463, WO 97/44337, WO 97/44036, WO 97/44322, EP 0763534, Aoki et al., J Pharmacol Exp Ther., 295(1):255-60 (2000), Del Piaz et al., Eur. J. Med. Chem., 35; 463-480 (2000), and Barnette et al., Pharmacol. Rev. Commun. 8: 65-73 (1997).

In some embodiments, the cAMP-specific PDE inhibitor is Cilomilast (SB-207499); Filaminast; Tibenelast (LY-186655); Ibudilast; Piclamilast (RP 73401); Doxofylline; Cipamfylline (HEP-688); atizoram (CP-80633); theophylline; isobutylmethylxanthine; Mesopram (ZK-117137); Zardaverine; vinpocetine; Rolipram (ZK-62711); Arofylline (LAS-31025); roflumilast (BY-217); Pumafentrin (BY-343); Denbufylline; EHNA; milrinone; Siguazodan; Zaprinast; Tolafentrine; Isbufylline; IBMX; 1C-485; dyphylline; verolylline; bamifylline; pentoxyfilline; enprofilline; lirimilast (BAY 19-8004); filaminast (WAY-PDA-641); benafentrine; trequinsin; nitroquazone; cilostamide; vesnarinone; piroximone; enoximone; aminone; olprinone; imazodan and 5-methyl-imazodan; indolidan; anagrelide; carbazeran; ampizone; emoradan; motapizone; phthalazinol; lixazinone (RS82856); quazinone; bemorandan (RWJ 22867); adibendan (BM 14,478); Pimobendan (MCI-154); Saterinone (BDF 8634); Tetomilast (OPC-6535); benzafentrine; sulmazole (ARL 115); Revizinone; 349-U-85; AH-21-132; ATZ-1993; AWD-12-343; AWD-12-281; AWD-12-232; BRL 50481; CC-7085; CDC-801; CDC-998; CDP-840; CH-422; CH-673; CH-928; CH-3697; CH-3442; CH-2874; CH-4139; Chiroscience 245412; CI-930; CI-1018; CI-1044; CI-1118; CP-353164; CP-77059; CP-146523; CP-293321; CP-220629; CT-2450; CT-2820; CT-3883; CT-5210; D-4418; D-22888; E-4021; EMD 54622; EMD-53998; EMD-57033; GF-248; GW-3600; IC-485; ICI-63197; ICI 153,110; IPL-4088; KF-19514; KW-4490; L-787258; L-826141; L-791943; LY181512; NCS-613; NM-702; NSP-153; NSP-306; NSP-307; Org-30029; Org-20241; Org-9731; ORG 9935; PD-168787; PD-190749; PD-190036; PDB-093; PLX650; PLX369; PLX371; PLX788; PLX939; Ro-20-1724; RPR-132294; RPR-117658A; RPR-114597; RPR-122818; RPR-132703; RS-17597; RS-25344; RS-14203; SCA 40; Sch-351591; SDZ-ISQ-844; SDZ-MKS-492; SKF 94120; SKF-95654; SKF-107806; SKF 96231; T-440; T-2585; WAY-126120; WAY-122331; WAY-127093B; WIN-63291; WIN-62582; V-11294A; VMX 554; VMX 565; XT-044; XT-611; Y-590; YM-58897; YM-976; ZK-62711; methyl 3-[6-(2H-3,4,5,6-tetrahydropyran-2-yloxy)-2-(3-thienylcarbonyl)benzo[b]furan-3-yl]propanoate; 4-[4-methoxy-3-(5-phenylpentyloxy)phenyl]-2-methylbenzoic acid; methyl 3-{2-[(4-chlorophenyl)carbonyl]-6-hydroxybenzo[b]furan-3-yl}propanoate; (R*,R*)-(±)-methyl 3-acetyl-4-[3-(cyclopentyloxy)-4-methoxyphenyl]-3-methyl-1-pyrrolidinecarboxylat; or 4-(3-bromophenyl)-1-ethyl-7-methylhydropyridino[2,3-b]pyridin-2-one.

Examples of PDE3 inhibitors include dihydroquinolinone compounds such as cilostamide, cilostazol, vesnarinone, and OPC 3911; imidazolones such as piroximone and enoximone; bipyridines such as milrinone, aminone and olprinone; imidazolines such as imazodan and 5-methyl-imazodan; pyridazinones such as indolidan, and LY181512; ibudilast, isomazole, motapizone, phthalazinol, trequinsin, lixazinone (RS82856), Y-590, SKF 94120, quazinone, ICI 153,110, bemorandan (RWJ 22867), siguazodan (SK&F 94836), adibendan (BM 14,478), Pimobendan (UD-CG 115, MCI-154), Saterinone (BDF 8634), NSP-153, zardaverine, quinazolines, benzafentrine, sulmazole (ARL 115), ORG 9935, CI-930, SKF-95654, SDZ-MKS-492, 349-U-85, EMD-53998, EMD-57033, NSP-306, NSP-307, Revizinone, NM-702, WIN-62582, ATZ-1993, WIN-63291, ZK-62711, PLX650; PLX369; PLX788; PLX939; anagrelide, carbazeran, ampizone, emoradan, and compounds disclosed in U.S. Pat. No. 6,156,753.

Examples of PDE4 inhibitors include pyrrolidinones, such as the compounds disclosed in U.S. Pat. No. 5,665,754, US20040152754 and US20040023945; quinazolineones, such as the compounds disclosed in U.S. Pat. Nos. 6,747,035, 6,828,315, WO 97/49702 and WO 97/42174; xanthine derivatives; phenylpyridines, such as the compounds disclosed in U.S. Pat. Nos. 6,410,547, 6,090,817, and WO 97/22585; diazepine derivatives, such as the compounds disclosed in WO 97/36905; oxime derivatives, such as the compounds disclosed in U.S. Pat. No. 5,693,659 and WO 96/00215; naphthyridines, such as the compounds described in U.S. Pat. Nos. 5,817,670, 6,740,662, 6,136,821, 6,331,548, 6,297,248, 6,541,480, 6,642,250, 6,900,205, Trifilieff et al., Pharmacology, 301(1): 241-248 (2002) and Hersperger et al., J Med. Chem., 43(4):675-82 (2000); benzofurans, such as the compounds disclosed in U.S. Pat. Nos. 5,902,824, 6,211,203, 6,514,996, 6,716,987, 6,376,535, 6,080,782, 6,054,475, EP 819688, EP685479, and Perrier et al., Bioorg. Med. Chem. Lett. 9:323-326 (1999); phenanthridines, such as those disclosed in U.S. Pat. Nos. 6,191,138, 6,121,279, and 6,127,378; benzoxazoles, such as those disclosed in 6,166,041 and 6,376,485; purine derivatives, such as the compounds disclosed in U.S. Pat. No. 6,228,859; benzamides, such as the compounds described in U.S. Pat. Nos. 5,981,527, 5,712,298, WO95/01338, WO 97/48697 and Ashton et al., J. Med Chem 37: 1696-1703 (1994); substituted phenyl compounds, such as the compounds disclosed in U.S. Pat. Nos. 6,297,264, 5,866,593, 655,859,034, 6,245,774, 6,197,792, 6,080,790, 6,077,854, 5,962,483, 5,674,880, 5,786,354, 5,739,144, 5,776,958, 5,798,373, 5,891,896, 5,849,770, 5,550,137, 5,340,827, 5,780,478, 5,780,477, 5,633,257, and WO 95/35283; and substituted biphenyl compounds, such as those disclosed in U.S. Pat. No. 5,877,190; quinilinones, such as the compounds described in U.S. Pat. No. 6,800,625 and WO 98/14432.

Additional examples of PDE4 inhibitors useful in methods provided herein include compounds disclosed in U.S. Pat. Nos. 6,716,987, 6,514,996, 6,376,535, 6,740,655, 6,559,168, 6,069,151, 6,365,585, 6,313,116, 6,245,774, 6,011,037, 6,127,363, 6,303,789, 6,316,472, 6,348,602, 6,331,543, 6,333,354, 5,491,147, 5,608,070, 5,622,977, 5,580,888, 6,680,336, 6,569,890, 6,569,885, 6,500,856, 6,486,186, 6,458,787, 6,455,562, 6,444,671, 6,423,710, 6,376,489, 6,372,777, 6,362,213, 6,313,156, 6,294,561, 6,258,843, 6,258,833, 6,121,279, 6,043,263, RE38,624, 6,297,257, 6,251,923, 6,613,794, 6,407,108, 6,107,295, 6,103,718, 6,479,494, 6,602,890, 6,545,158, 6,545,025, 6,498,160, 6,743,802, 6,787,554, 6,828,333, 6,869,945, 6,894,041, 6,924,292, 6,949,573, 6,953,810, 5,972,927, 5,962,492, 5,814,651, 5,723,460, 5,716,967, 5,686,434, 5,502,072, 5,116,837, 5,091,431; 4,670,434; 4,490,371; 5,710,160, 5,710,170, 6,384,236, 3,941,785, US20050119225, US20050026913, WO 99/65880, WO 00/26201, WO 98/06704, WO 00/59890, WO9907704, WO9422852, WO 98/20007, WO 02/096423, WO 98/18796, WO 98/02440, WO 02/096463, WO 97/44337, WO 97/44036, WO 97/44322, EP 0763534, Aoki et al., J Pharmacol Exp Ther., 295(1):255-60 (2000), Del Piaz et al., Eur. J. Med. Chem., 35; 463-480 (2000), and Barnette et al., Pharmacol. Rev. Commun. 8: 65-73 (1997).

In some embodiments, the PDE4 inhibitor is Cilomilast (SB-207499); Filaminast; Tibenelast (LY-186655); Ibudilast; Piclamilast (RP 73401); Doxofylline; Cipamfylline (HEP-688); atizoram (CP-80633); theophylline; isobutylmethylxanthine; Mesopram (ZK-117137); Zardaverine; vinpocetine; Rolipram (ZK-62711); Arofylline (LAS-31025); roflumilast (BY-217); Pumafentrin (BY-343); Denbufylline; EHNA; milrinone; Siguazodan; Zaprinast; Tolafentrine; Isbufylline; IBMX; 1C-485; dyphylline; verolylline; bamifylline; pentoxyfilline; enprofilline; lirimilast (BAY 19-8004); filaminast (WAY-PDA-641); benafentrine; trequinsin; nitroquazone; Tetomilast (OPC-6535); AH-21-132; AWD-12-343; AWD-12-281; AWD-12-232; CC-7085; CDC-801; CDC-998; CDP-840; CH-422; CH-673; CH-928; CH-3697; CH-3442; CH-2874; CH-4139; Chiroscience 245412; CI-1018; CI-1044; CI-1118; CP-353164; CP-77059; CP-146523; CP-293321; CP-220629; CT-2450; CT-2820; CT-3883; CT-5210; D-4418; D-22888; E-4021; EMD 54622; GF-248; GW-3600; IC-485; ICI-63197; IPL-4088; KF-19514; KW-4490; L-787258; L-826141; L-791943; NCS-613; Org-30029; Org-20241; Org-9731; PD-168787; PD-190749; PD-190036; PDB-093; PLX650; PLX369; PLX371; PLX788; PLX939; Ro-20-1724; RPR-132294; RPR-117658A; RPR-114597; RPR-122818; RPR-132703; RS-17597; RS-25344; RS-14203; SCA 40; Sch-351591; SDZ-ISQ-844; SKF-107806; SKF 96231; T-440; T-2585; WAY-126120; WAY-122331; WAY-127093B; V-11294A; VMX 554; VMX 565; XT-044; XT-611; YM-58897; YM-976; methyl 3-[6-(2H-3,4,5,6-tetrahydropyran-2-yloxy)-2-(3-thienylcarbonyl)benzo[b]furan-3-yl]propanoate; 4-[4-methoxy-3-(5-phenylpentyloxy)phenyl]-2-methylbenzoic acid; methyl 3-{2-[(4-chlorophenyl)carbonyl]-6-hydroxybenzo[b]furan-3-yl}propanoate; (R*,R*)-(±)-methyl 3-acetyl-4-[3-(cyclopentyloxy)-4-methoxyphenyl]-3-methyl-1-pyrrolidinecarboxylat; or 4-(3-bromophenyl)-1-ethyl-7-methylhydropyridino[2,3-b]pyridin-2-one.

Examples of PDE7 inhibitors useful in methods described herein include BRL 50481; PLX369; PLX788; and compounds described in U.S. Pat. Nos. 6,818,651; 6,737,436, 6,613,778, 6,617,357; 6,146,876, 6,838,559, 6,884,800, US20050059686; US20040138279; US20050222138; US20040214843; US20040106631; US 20030045557; US 20020198198; US20030162802, US20030092908, US 20030104974; US20030100571; 20030092721; and US20050148604.

Examples of inhibitors of PDE8 include dipyridamole.

In some embodiments, the PDE inhibitor inhibits a cGMP-specific PDE. Examples of cGMP specific PDE inhibitors useful in the methods described herein include pyrimidine and pyrimidinone derivatives, such as the compounds described in U.S. Pat. Nos. 6,677,335, 6,458,951, 6,251,904, 6,787,548, 5,294,612, 5,250,534, 6,469,012, WO 94/28902, WO96/16657, EP0702555, and Eddahibi, Br. J. Pharmacol., 125(4): 681-688 (1988); griseolic acid derivatives, such as the compounds disclosed in U.S. Pat. No. 4,460,765; 1-arylnaphthalene lignans, such as those described in Ukita, J. Med. Chem. 42(7): 1293-1305 (1999); quinazoline derivatives, such as 4-[[3',4'-(methylenedioxy)benzyl]amino]-6-methoxyquinazoline) and compounds described in 3,932,407, 4,146,718, and RE31,617; pyrroloquinolones and pyrrolopyridinones, such as those described in U.S. Pat. Nos. 6,686,349, 6,635,638, 6,818,646, US20050113402; carboline derivatives, such the compounds described in U.S. Pat. Nos. 6,492,358, 6,462,047, 6,821,975, 6,306,870, 6,117,881, 6,043,252, 3,819,631, US20030166641, WO 97/43287, Daugan et al., J Med. Chem., 46(21):4533-42 (2003), and Daugan et al., J Med. Chem., 9; 46(21):4525-32 (2003); imidazo derivatives, such as the compounds disclosed in U.S. Pat. Nos. 6,130,333, 6,566,360, 6,362,178, 6,582,351, US20050070541, and US20040067945; and compounds described in U.S. Pat. Nos. 6,825,197, 5,719,283, 6,943,166, 5,981,527, 6,576,644, 5,859,009, 6,943,253, 6,864,253, 5,869,516, 5,488,055, 6,140,329, 5,859,006, 6,143,777, WO 96/16644, WO 01/19802, WO 96/26940, Dunn, Org. Proc. Res. Dev., 9: 88-97 (2005), and Bi et al., Bioorg Med Chem. Lett., 11(18): 2461-4 (2001).

Examples of PDE5 inhibitors useful in methods described herein include pyrimidine and pyrimidinone derivatives, such as the compounds described in U.S. Pat. Nos. 6,677,335, 6,458,951, 6,251,904, 6,787,548, 5,294,612, 5,250,534, 6,469,012, WO 94/28902, WO96/16657, EP0702555, and Eddahibi, Br. J. Pharmacol., 125(4): 681-688 (1988); griseolic acid derivatives, such as the compounds disclosed in U.S. Pat. No. 4,460,765; 1-arylnaphthalene lignans, such as those described in Ukita, J. Med. Chem. 42(7): 1293-1305 (1999); quinazoline derivatives, such as 4-[[3',4'-(methylenedioxy)benzyl]amino]-6-methoxyquinazoline) and compounds described in U.S. Pat. Nos. 3,932,407, 4,146,718, and RE31,617; pyrroloquinolones and pyrrolopyridinones, such as those described in U.S. Pat. Nos. 6,686,349, 6,635,638, 6,818,646, US20050113402; carboline derivatives, such the compounds described in U.S. Pat. Nos. 6,492,358, 6,462,047, 6,821,975, 6,306,870, 6,117,881, 6,043,252, 3,819,631, US20030166641, WO 97/43287, Daugan et al., J Med. Chem., 46(21):4533-42 (2003), and Daugan et al., J Med. Chem., 9; 46(21):4525-32 (2003); imidazo derivatives, such as the compounds disclosed in U.S. Pat. Nos. 6,130,333, 6,566,360, 6,362,178, 6,582,351, US20050070541, and US20040067945; and compounds described in U.S. Pat. Nos. 6,825,197, 6,943,166, 5,981,527, 6,576,644, 5,859,009, 6,943,253, 6,864,253, 5,869,516, 5,488,055, 6,140,329, 5,859,006, 6,143,777, WO 96/16644, WO 01/19802, WO 96/26940, Dunn, Org. Proc. Res. Dev., 9: 88-97 (2005), and Bi et al., Bioorg Med Chem. Lett., 11(18):2461-4 (2001).

In some embodiments, the PDE5 inhibitor is zaprinast; MY-5445; dipyridamole; vinpocetine; FR229934; 1-methyl-3-isobutyl-8-(methylamino)xanthine; furazlocillin; Sch-51866; E4021; GF-196960; IC-351; T-1032; sildenafil; tadalafil; vardenafil; DMPPO; RX-RA-69; KT-734; SKF-96231; ER-21355; BF/GP-385; NM-702; PLX650; PLX134; PLX369; PLX788; or vesnarinone.

In some embodiments, the PDE5 inhibitor is sildenafil or a related compound disclosed in U.S. Pat. Nos. 5,346,901, 5,250,534, or 6,469,012; tadalafil or a related compound disclosed in U.S. Pat. Nos. 5,859,006, 6,140,329, 6,821,975, or 6,943,166; or vardenafil or a related compound disclosed in U.S. Pat. No. 6,362,178.

Examples of PDE6 inhibitors useful in methods described herein include dipyridamole and zaprinast.

Examples of PDE9 inhibitors useful in methods described herein include SCH-51866; IBMX; and BAY 73-6691.

In some embodiments, the PDE inhibitor inhibits dual-specificity PDE. Examples of dual-specificity PDE inhibitors useful in the methods described herein include the cAMP-specific and cGMP-specific PDE inhibitors described herein; MMPX; KS-505a; W-7; Phenothiazines; Bay 60-7550 and related compounds described in Boess et al., Neuropharmacology, 47(7):1081-92 (2004); UK-235,187 and related compounds described in EP 579496; and compounds described in U.S. Pat. Nos. 6,930,114, 4,861,891, US20020132754 US20040138249, US20040249148, US20040106631, WO 951997, and Maw et al., Bioorg Med Chem. Lett. 2003 Apr. 17; 13(8):1425-8.

Examples of PDE1 inhibitors include IBMX; vinpocetine; MMPX; KS-505a; SCH-51866; W-7; PLX650; PLX371; PLX788; Phenothiazines; and compounds described in 4,861,891.

Examples of PDE2 inhibitors include EHNA; PLX650; PLX369; PLX788; PLX 939; Bay 60-7550 and related compounds described in Boess et al., Neuropharmacology, 47(7): 1081-92 (2004); and compounds described in US20020132754.

Examples of PDE1 inhibitors include sildenafil; SCH-51866; papaverine; Zaprinast; Dipyridamole; E4021; Vinpocetine; EHNA; Milrinone; Rolipram; PLX107; and compounds described in 6,930,114, US20040138249, US20040249148.

Examples of PDE1 inhibitors include IC-351 and related compounds described in WO 9519978; E4021 and related compounds described in WO 9307124; UK-235,187 and related compounds described in EP 579496; PLX788; Zaprinast; Dipyridamole; and compounds described in US20040106631 and Maw et al., Bioorg Med Chem. Lett. 2003 Apr. 17; 13(8):1425-8.

In some embodiments, the PDE inhibitor is a compound described in U.S. Pat. Nos. 5,091,431, 5,081,242, 5,066,653, 5,010,086, 4,971,972, 4,963,561, 4,943,573, 4,906,628, 4,861,891, 4,775,674, 4,766,118, 4,761,416, 4,739,056, 4,721,784, 4,701,459, 4,670,434, 4,663,320, 4,642,345, 4,593,029, 4,564,619, 4,490,371, 4,489,078, 4,404,380, 4,370,328, 4,366,156, 4,298,734, 4,289,772, RE30,511, 4,188,391, 4,123,534, 4,107,309, 4,107,307, 4,096,257, 4,093,617, 4,051,236, or 4,036,840.

A PDE agent as described herein includes pharmaceutically acceptable salts, derivatives, prodrugs, metabolites, stereoisomer, or other variant of the agent. For example, in some embodiments, the PDE inhibitor is roflumilast N-oxide, which is the primary metabolite of roflumilast in humans and has been shown to have enhanced efficacy in vivo. In some embodiments, a PDE inhibitor is chemically modified to reduce side effects, toxicity, solubility, and/or other characteristics. For example, in some embodiments, the PDE inhibitor is benzylated in order to reduce emetogenic effects, as described, e.g., in U.S. Pat. No. 6,555,572, herein incorporated by reference. Methods for preparing and administering salts, derivatives, prodrugs, and metabolites of various compounds are well known in the art.

Compounds described herein that contain a chiral center include all possible stereoisomers of the compound, including compositions comprising the racemic mixture of the two enantiomers, as well as compositions comprising each enantiomer individually, substantially free of the other enantiomer. Thus, for example, contemplated herein is a composition comprising the S enantiomer substantially free of the R enantiomer, or the R enantiomer substantially free of the S enantiomer. If the named compound comprises more than one chiral center, the scope of the present disclosure also includes compositions comprising mixtures of varying proportions between the diastereomers, as well as compositions comprising one or more diastereomers substantially free of one or more of the other diastereomers. By "substantially free" it is meant that the composition comprises less than 25%, 15%, 10%, 8%, 5%, 3%, or less than 1% of the minor enantiomer or diastereomer(s). Methods for synthesizing, isolating, preparing, and administering various stereoisomers are known in the art.

In some embodiments, compositions comprising one or more stereoisomers substantially free from one or more other stereoisomers provide enhanced affinity, potency, selectivity and/or therapeutic efficacy relative to compositions comprising a greater proportion of the minor stereoisomer(s). For example, in some embodiments, a PDE agent is the (−)-enantiomer of rolipram, which has a higher pharmacological potency than the (+)-enantiomer, due e.g., to a higher affinity for PDEs (e.g., PDE4) and/or stereospecific metabolism, with the (+)-enantiomer exhibiting a faster clearance rate than the (−)-enantiomer. In some embodiments, a PDE agent is a variant of a known PDE inhibitor that has enhanced affinity, potency, selectivity and/or therapeutic efficacy.

In some embodiments, a PDE agent used in a method described herein have similar activity against several PDE isozymes. Examples of non-selective inhibitors include, e.g., theophylline, theobromine, dipyridamole, IBMX, pentoxifylline, ibudilast, and papaverine.

In other embodiments, a PDE agent may exhibit "isozyme-selective" activity. For example, in various embodiments, a PDE agent is active against one or more PDE families and substantially inactive against one or more other PDE families. In some embodiments, a PDE agent exhibits isozyme-selective activity against one or more PDE families that are active in the CNS, including but not limited to, PDE1, PDE2, PDE3, PDE4 (e.g., PDE4A, PDE4B, PDE4D), PDE5, PDE7, PDE8, (e.g., PDE8B), PDE9, PDE10 and/or PDE11. In further embodiments, a PDE agent exhibits isozyme-selectivity within a PDE family. For example, the PDE4 inhibitor cilomilast is approximately 10-fold more selective for PDE4D, than for PDE4A, PDE4B, and PDE4C.

In additional embodiments, PDE inhibitors exhibit isozyme-selective activity against one or more PDEs residing in a neurogenic region of the brain, such as the dentate gyrus, the subventricular zone, and/or the olfactory bulb. For example, PDE inhibitors are active against PDE1A, PDE1B, PDE1C, PDE2A, and/or PDE5A, which are expressed in the subventricular zone, hippocampus and olfactory bulb, as well as throughout the brain. Other isozymes expressed at high levels in the brain include, but are not limited to, PDE4A, PDE4B, PDE4D, PDE9A, and PDE10A.

In some embodiments, PDE inhibitors have "target selective" activity under certain conditions, wherein the PDE inhibitor is substantially inactive against non-PDE molecular targets, such as (i) CNS receptors, including but not limited to, glutamate receptors, GABA receptors, opioid receptors (e.g., mu, delta, and kappa opioid receptors), muscarinic receptors (e.g., m1-m5 receptors), histaminergic receptors, phencyclidine receptors, dopamine receptors, alpha and beta-adrenoceptors, sigma receptors (type-1 and type-2), and 5HT-1 and 5-HT-2 receptors; (ii) kinases, including but not limited to, Mitogen-activated protein kinase, PKA, PKB, PKC, CK-2; c-Met, JAK, SYK, KDR, FLT-3, c-Kit, Aurora kinase, CDK kinases (e.g., CDK4/cyclin D, CDK2/cyclin E, CDK2/cyclin A, CDK1/cyclin B), and TAK-1; (iii) ion channels (e.g., calcium, chloride, potassium, and the like) and/or (iv) enzymes, including but not limited to, adenyl or guanyl cyclases, HDACs, and the like. In other embodiments, a PDE agent used in the methods described herein is substantially inactive with respect to other receptors, such as muscarinic receptors, nicotinic receptors, dopamine receptors, and opioid receptors as non-limiting examples.

In some embodiments, a PDE inhibitor exhibits both isozyme and target selectivity. In further embodiments, isozyme and/or target selectivity is achieved by administering a PDE inhibitor at a dosage and in a manner that produces a concentration of the PDE inhibitor in the target organ or tissue that is therapeutically effective against one or more PDE isozymes, while being sub-therapeutic at other PDE isozymes and/or targets. Advantageously, the isozyme and/or target selectivity of a PDE inhibitor results in enhanced efficacy, fewer side effects, lower effective dosages, less frequent dosing, and other desirable attributes relative to non-selective modulators.

In some embodiments, the PDE inhibitor exhibits dual-selectivity, being substantially more active against two PDE isozymes relative to other PDE isozymes. For example, in some embodiments, the PDE inhibitor is a dual PDE4/PDE7 inhibitor, such as the compounds described in US20030104974; a dual PDE3/PDE4 inhibitor, such as zardaverine, tolafentrine, benafentrine, trequinsine, Org-30029, L-686398, SDZ-ISQ-844, Org-20241, EMD-54622, or a compound described in U.S. Pat. Nos. 5,521,187, or 6,306,869; or a dual PDE1/PDE4 inhibitor, such as KF19514 (5-phenyl-3-(3-pyridyl)methyl-3H-imidazo[4,5-c][1,8]naphthyridin-4 (5H)-one)

In some embodiments, the PDE inhibitor used in a combination or method disclosed herein is caffeine or other ingested compound such as a vitamin like folic acid. In some embodiments, the caffeine or folic acid is administered in a formulation comprising a PDE agent. In other embodiments, the caffeine or folic acid is administered simultaneously with a PDE agent. In alternative embodiments, the caffeine is administered in a formulation, dosage, or concentration lower or higher than that of a caffeinated beverage such as coffee, tea, or soft drinks. Similarly, folic acid may be administered in a formulation, dosage, or concentration lower or higher than that of a nutritional supplement containing folic acid. In further embodiments, the caffeine or folic acid is administered by a non-oral means, including, but not limited to, parenteral (e.g., intravenous, intradermal, subcutaneous, inhalation), transdermal (topical), transmucosal, rectal, or intranasal (including, but not limited to, inhalation of aerosol suspensions for delivery of compositions to the nasal mucosa, trachea and bronchioli) administration. The disclosure includes embodiments with the explicit exclusion of caffeine, folic acid, or another one or more of the described agents for use in combination with a PDE agent.

In further alternative embodiments, the caffeine is in an isolated form, such as that which is separated from one or more molecules or macromolecules normally found with caffeine before use in a combination or method as disclosed herein. In other embodiments, the caffeine is completely or partially purified from one or more molecules or macromolecules normally found with the caffeine. Exemplary cases of molecules or macromolecules found with caffeine include a plant or plant part, an animal or animal part, and a food or beverage product.

In some embodiments, a PDE agent is a novel PDE inhibitor identified using structure-activity relationships and teachings in the art and described, e.g., in Keller et al., Chem Pharm Bull (Tokyo). 2001 August; 49(8):1009-17; Jin et al., J Biol Chem 267: 18929-18939 (1992), Pillai et al., Proc Natl Acad Sci USA 90: 11970-11974 (1993), Atienza et al., J. Biol. Chem., 274: 4839-4847 (1997), Xu et al., Science (Wash DC) 288: 1822-1825 (2000), Boyle et al., Bioorg Med Chem. Lett., 15(9):2365-9 (2005); Lee et al., FEBS Lett., 530(1-3): 53-8 (2002); Maw et al., Bioorg Med Chem. Lett. 2003 Apr. 17; 13(8):1425-8; and Richter et al., Cell Signal., 13(3):159-67 (2001), each of which are herein incorporated by reference in their entirety.

In other embodiments, a PDE agent is a molecule or composition that inhibits the expression of a target PDE, such as an antisense nucleotide (e.g., siRNA) that specifically hybridizes with the cellular mRNA and/or genomic DNA corresponding to the gene(s) of the target PDE so as to inhibit their transcription and/or translation, or a ribozyme that specifically cleaves the mRNA of a target PDE. Antisense nucleotides and ribozymes can be delivered directly to cells, or indirectly via an expression vector which produces the nucleotide when transcribed in the cell. Methods for designing and administering antisense oligonucleotides and ribozymes are known in the art, and are described, e.g., in Mautino et al., Hum Gene Ther 13:1027-37 (2002) and Pachori et al., Hypertension 39:969-75 (2002), herein incorporated by reference. Examples of antisense compositions against PDEs include, e.g., the anti-PDE4 compositions disclosed in US20030045490 and WO 00/40714, and the anti-PDE1 and anti-PDE4 compositions disclosed in U.S. Pat. No. 5,885,834, all of which are herein incorporated by reference. In some embodiments, neurogenesis modulation is achieved by administering a combination of at least one PDE inhibitor, and at least one PDE transcriptional/translational inhibitor.

As described herein, a PDE agent, optionally in combination with one or more other neurogenic agents, is administered to an animal or human subject to result in neurogenesis. A combination may thus be used to treat a disease, disorder, or condition of the disclosure.

Methods for assessing the nature and/or degree of neurogenesis in vivo and in vitro, for detecting changes in the nature and/or degree of neurogenesis, for identifying neurogenesis modulating agents, for isolating and culturing neural stem cells, and for preparing neural stem cells for transplantation or other purposes are disclosed, for example, in U.S. Provisional Application No. 60/697,905, and U.S. Publication Nos. 2005/0009742 and 2005/0009847, 20050032702, 2005/0031538, 2005/0004046, 2004/0254152, 2004/0229291, and 2004/0185429, all of which are herein incorporated by reference in their entirety.

Selection of a PDE agent, or additional agent of a combination, may be readily determined by evaluating their potency in relation to neurogenesis and their target selectivity with routine methods as described herein and as known to the skilled person. The agent(s) may then be evaluated for their toxicity (if any), pharmacokinetics (such as absorption, metabolism, distribution and degradation/elimination) by use of with recognized standard pharmaceutical techniques. Embodiments of the disclosure include use of agent(s) that are potent and selective, and have either an acceptable level of toxicity or no significant toxic effect, at the therapeutic dose. Additional selections may be made based on bioavailability of the agent following oral administration.

Formulations and Doses

In some embodiments of the disclosure, a PDE agent, optionally in combination with one or more other neurogenic agents, is in the form of a composition that includes at least one pharmaceutically acceptable excipient. As used herein, the term "pharmaceutically acceptable excipient" includes any excipient known in the field as suitable for pharmaceutical application. Suitable pharmaceutical excipients and formulations are known in the art and are described, for example, in Remington's Pharmaceutical Sciences (19th ed.) (Genarro, ed. (1995) Mack Publishing Co., Easton, Pa.). Preferably, pharmaceutical carriers are chosen based upon the intended mode of administration of a PDE agent, optionally in combination with one or more other neurogenic agents. The pharmaceutically acceptable carrier may include, for example, disintegrants, binders, lubricants, glidants, emollients, humectants, thickeners, silicones, flavoring agents, and water.

A PDE agent, optionally in combination with one or more other neurogenic agents, may be incorporated with excipients and administered in the form of ingestible tablets, buccal tablets, troches, capsules, elixirs, suspensions, syrups, wafers, or any other form known in the pharmaceutical arts. The pharmaceutical compositions may also be formulated in a sustained release form. Sustained release compositions, enteric coatings, and the like are known in the art. Alternatively, the compositions may be a quick release formulation.

The amount of a combination of a PDE agent, or a combination thereof with one or more other neurogenic agents, may be an amount that also potentiates or sensitizes, such as by activating or inducing cells to differentiate, a population of neural cells for neurogenesis. The degree of potentiation or sensitization for neurogenesis may be determined with use of the combination in any appropriate neurogenesis assay, including, but not limited to, a neuronal differentiation assay described herein. In some embodiments, the amount of a combination of a PDE agent, optionally in combination with one or more other neurogenic agents, is based on the highest amount of one agent in a combination, which amount produces no detectable neuroproliferation in vitro but yet produces neurogenesis, or a measurable shift in efficacy in promoting neurogenesis in vitro, when used in the combination.

As disclosed herein, an effective amount of a PDE agent, optionally in combination with one or more other neurogenic agents, in the described methods is an amount sufficient, when used as described herein, to stimulate or increase neurogenesis in the subject targeted for treatment when compared to the absence of the combination. An effective amount of a PDE agent alone or in combination may vary based on a number of factors, including but not limited to, the activity of the active compounds, the physiological characteristics of the subject, the nature of the condition to be treated, and the route and/or method of administration. General dosage ranges of certain compounds are provided herein and in the cited references based on animal models of CNS diseases and conditions. Various conversion factors, formulas, and methods for determining human dose equivalents of animal dosages are known in the art, and are described, e.g., in Freireich et al., Cancer Chemother Repts 50(4): 219 (1966), Monro et al., Toxicology Pathology, 23: 187-98 (1995), Boxenbaum and Dilea, J. Clin.Pharmacol. 35: 957-966 (1995), and Voisin et al., Reg. Toxicol. Pharmacol., 12(2): 107-116 (1990), which are herein incorporated by reference.

The disclosed methods typically involve the administration of a PDE agent, optionally in combination with one or more other neurogenic agents, in a dosage range of from about 0.001 ng/kg/day to about 200 mg/kg/day. Other non-limiting dosages include from about 0.001 to about 0.01 ng/kg/day, about 0.01 to about 0.1 ng/kg/day, about 0.1 to about 1 ng/kg/day, about 1 to about 10 ng/kg/day, about 10 to about 100 ng/kg/day, about 100 ng/kg/day to about 1 µg/kg/day, about 1 to about 2 µg/kg/day, about 2 µg/kg/day to about 0.02 mg/kg/day, about 0.02 to about 0.2 mg/kg/day, about 0.2 to about 2 mg/kg/day, about 2 to about 20 mg/kg/day, or about 20 to about 200 mg/kg/day. However, as understood by those skilled in the art, the exact dosage of a PDE agent, optionally in combination with one or more other neurogenic agents, used to treat a particular condition will vary in practice due to a wide variety of factors. Accordingly, dosage guidelines provided herein are not limiting as the range of actual dosages, but rather provide guidance to skilled practitioners in selecting dosages useful in the empirical determination of dosages for individual patients. Advantageously, methods described herein allow treatment of one or more conditions with reductions in side effects, dosage levels, dosage frequency, treatment duration, safety, tolerability, and/or other factors. So where suitable dosages for a PDE agent to modulate a PDE activity are known to a skilled person, the disclosure includes the use of about 75%, about 50%, about 33%, about 25%, about 20%, about 15%, about 10%, about 5%, about 2.5%, about 1%, about 0.5%, about 0.25%, about 0.2%, about 0.1%, about 0.05%, about 0.025%, about 0.02%, about 0.01%, or less than the known dosage.

In some embodiments, an effective, neurogenesis modulating amount is an amount that achieves a concentration within the target tissue, using the particular mode of administration, at or above the $IC_{50}$ for activity of a PDE agent. In some embodiments, the PDE agent is administered in a manner and dosage that gives a peak concentration of about 1, 1.5, 2, 2.5, 5, 10, 20 or more times the $IC_{50}$ concentration. $IC_{50}$ values and bioavailability data for various PDE agent are known in the art, and are described, e.g., in the references cited herein.

In further embodiments, an effective, neurogenesis modulating amount is a dose that lies within a range of circulating concentrations that includes the $ED_{50}$ (the pharmacologically effective dose in 50% of subjects) with little or no toxicity.

In some embodiments, an effective, neurogenesis modulating amount is an amount that achieves a peak concentration within the target tissue, using the particular mode of administration, at or above the $IC_{50}$ or $EC_{50}$ concentration for the modulation of neurogenesis. In various embodiments, a PDE agent is administered in a manner and dosage that gives a peak concentration of about 1, 1.5, 2, 2.5, 5, 10, 20 or more times the $IC_{50}$ or $EC_{50}$ concentration for the modulation of neurogenesis. In some embodiments, the $IC_{50}$ or $EC_{50}$ concentration for the modulation of neurogenesis is substantially lower than the $IC_{50}$ concentration for activity of a PDE agent, allowing treatment of conditions for which it is beneficial to modulate neurogenesis with lower dosage levels, dosage frequencies, and/or treatment durations relative to known therapies. $IC_{50}$ and $EC_{50}$ values for the modulation of neurogenesis can be determined using methods described in U.S. Provisional Application No. 60/697,905 to Barlow et al., filed Jul. 8, 2005, incorporated by reference, or by other methods known in the art.

In some embodiments $IC_{50}$ or $EC_{50}$ concentration for the modulation of neurogenesis is substantially lower than the $IC_{50}$ or $EC_{50}$ concentration for activity of a PDE agent at non-PDE targets, such as other kinases, receptors, or signaling molecules. $IC_{50}$ and $EC_{50}$ values for PDE agents at various kinases and other molecules are known in the art, and can be readily determined using established methods.

In other embodiments, the amount of a PDE agent used in vivo may be about 50%, about 45%, about 40%, about 35%, about 30%, about 25%, about 20%, about 18%, about 16%, about 14%, about 12%, about 10%, about 8%, about 6%, about 4%, about 2%, or about 1% or less than the maximum tolerated dose for a subject, including where one or more other neurogenic agents is used in combination with the PDE agent. This is readily determined for each PDE agent that has been in clinical use or testing, such as in humans.

Alternatively, the amount of a PDE agent, optionally in combination with one or more other neurogenic agents, may be an amount selected to be effective to produce an improvement in a treated subject based on detectable neurogenesis in vitro as described above. In some embodiments, such as in the case of a known PDE agent, the amount is one that minimizes clinical side effects seen with administration of the agent to a subject. The amount of an agent used in vivo may be about 50%, about 45%, about 40%, about 35%, about 30%, about 25%, about 20%, about 18%, about 16%, about 14%, about 12%, about 10%, about 8%, about 6%, about 4%, about 2%, or about 1% or less of the maximum tolerated dose in terms of acceptable side effects for a subject. This is readily determined for each PDE agent or other agent(s) of a combination disclosed herein as well as those that have been in clinical use or testing, such as in humans.

In other embodiments, the amount of an additional neurogenic sensitizing agent in a combination with a PDE agent of the disclosure is the highest amount which produces no detectable neurogenesis in vitro, including in animal (or non-human) models for behavior linked to neurogenesis, but yet produces neurogenesis, or a measurable shift in efficacy in promoting neurogenesis in the in vitro assay, when used in combination with a PDE agent. Embodiments include amounts which produce about 1%, about 2%, about 4%, about 6%, about 8%, about 10%, about 12%, about 14%, about 16%, about 18%, about 20%, about 25%, about 30%, about 35%, or about 40% or more of the neurogenesis seen with the amount that produces the highest level of neurogenesis in an in vitro assay.

As described herein, the amount of a PDE agent, optionally in combination with one or more other neurogenic agents, may be any that is effective to produce neurogenesis, optionally with reduced or minimized amounts of astrogenesis. In some embodiments, the amount may be the lowest needed to produce a desired, or minimum, level of detectable neurogenesis or beneficial effect. Of course the administered PDE agent, alone or in a combination disclosed herein, may be in the form of a pharmaceutical composition.

In some embodiments, an effective, neurogenesis modulating amount of a combination of a PDE agent, optionally in combination with one or more other neurogenic agents, is an amount of a PDE agent (or of each agent in a combination) that achieves a concentration within the target tissue, using the particular mode of administration, at or above the $IC_{50}$ or $EC_{50}$ for activity of target molecule or physiological process. In some cases, a PDE agent, optionally in combination with one or more other neurogenic agents, is administered in a manner and dosage that gives a peak concentration of about 1, about 1.5, about 2, about 2.5, about 5, about 10, about 20 or more times the $IC_{50}$ or $EC_{50}$ concentration of the PDE agent (or each agent in the combination). $IC_{50}$ and $EC_{50}$ values and bioavailability data for a PDE agent and other agent(s) described herein are known in the art, and are described, e.g., in the references cited herein or can be readily determined using established methods. In addition, methods for determining the concentration of a free compound in plasma and extracellular fluids in the CNS, as well pharmacokinetic properties, are known in the art, and are described, e.g., in de Lange et al., AAPS Journal, 7(3): 532-543 (2005). In some embodiments, a PDE agent, optionally in combination with one or more other neurogenic agents, described herein is administered, as a combination or separate agents used together, at a frequency of at least about once daily, or about twice daily, or about three or more times daily, and for a duration of at least about 3 days, about 5 days, about 7 days, about 10 days, about 14 days, or about 21 days, or about 4 weeks, or about 2 months, or about 4 months, or about 6 months, or about 8 months, or about 10 months, or about 1 year, or about 2 years, or about 4 years, or about 6 years or longer.

In other embodiments, an effective, neurogenesis modulating amount is a dose that produces a concentration of a PDE agent (or each agent in a combination) in an organ, tissue, cell, and/or other region of interest that includes the $ED_{50}$ (the pharmacologically effective dose in 50% of subjects) with little or no toxicity. $IC_{50}$ and $EC_{50}$ values for the modulation of neurogenesis can be determined using methods described in U.S. Provisional Application No. 60/697,905 to Barlow et al., filed Jul. 8, 2005, incorporated by reference, or by other methods known in the art. In some embodiments, the $IC_{50}$ or $EC_{50}$ concentration for the modulation of neurogenesis is substantially lower than the $IC_{50}$ or $EC_{50}$ concentration for activity of a PDE agent and/or other agent(s) at non-targeted molecules and/or physiological processes.

In some methods described herein, the application of a PDE agent in combination with one or more other neurogenic agents may allow effective treatment with substantially fewer and/or less severe side effects compared to existing treatments. In some embodiments, combination therapy with a PDE agent and one or more additional neurogenic agents allows the combination to be administered at dosages that would be sub-therapeutic when administered individually or when compared to other treatments. In other embodiments, each agent in a combination of agents may be present in an amount that results in fewer and/or less severe side effects than that which occurs with a larger amount. Thus the combined effect of the neurogenic agents will provide a desired neurogenic activity while exhibiting fewer and/or less severe side effects overall. Non-limiting examples of side effects which may be reduced, in number and/or severity, include, but are not limited to, sweating, diarrhea, flushing, hypotension, bradycardia, bronchoconstriction, urinary bladder contraction, nausea, vomiting, parkinsonism, and increased mortality risk. In further embodiments, methods described herein allow treatment of certain conditions for which treatment with the same or similar compounds is ineffective using known methods due, for example, to dose-limiting side effects, toxicity, and/or other factors.

In some embodiments, the disclosure includes a combination, of a PDE agent and a second agent, where one or both of the agents is used to treat hypertension, such as in a case where one or both agents has hypotensive effects. The disclosure includes a composition or formulation of such a combination in doses that reduces such hypotensive effects. Non-limiting examples of such doses include amounts that are lower than those used to treat hypertension, or lower than those which are sufficient to treat hypertension, in an animal subject or human patient. In some cases, the dose of one or both agents may be from about one-thirtieth to about one-half of an amount used to treat hypertension or an amount sufficient to treat hypertension. In other cases, the dose of one or both agents may be less than the about one-thirtieth amount.

In other embodiments, the dose of one or both agents is an amount which produces an acceptable level of hypotension in a normotensive subject or patient. The amount may be one which is insufficient to produce a detectable or measurable reduction in hypertension in a hypertensive subject or patient.

Routes of Administration

As described, the methods of the disclosure comprise contacting a cell with a PDE agent, optionally in combination with one or more other neurogenic agents, or administering such an agent or combination to a subject, to result in neurogenesis. Some embodiments comprise the use of one PDE agent, such as ibudilast or MN-166, or dipyridamole (persantine); a PDE1 inhibitor, such as vinpocetine; a PDE3 inhibitor, such as enoximone, milrinone, pimobendan, flosequinan, levosimendan, vesnarinone, olprinone, aminone, inamrinone, anagrelide, cilostazol, or imazodan; a PDE4 inhibitor, such as cilomilast, roflumilast, rolipram, MEM 1414, MEM 1971, NIK 616, GK 07294A, 256066, GW 842470, ONO 6126, PLX369, HT-0712, IPL 455903, IC 485, or NVP-ABE171; or a PDE5 inhibitor, such as revatio, cialis (tadalafil), levitra (vardenafil), DA-8159, dapoxetine, avanafil (TA-1790), SCH-466132, or ABT-670 in combination with one or more other neurogenic agents. In other embodiments, a combination of two or more of the above agents, is used in combination with one or more other neurogenic agents.

In some embodiments, methods of treatment disclosed herein comprise the step of administering to a mammal a PDE agent, optionally in combination with one or more other neurogenic agents, for a time and at a concentration sufficient to treat the condition targeted for treatment. The disclosed methods can be applied to individuals having, or who are likely to develop, disorders relating to neural degeneration, neural damage and/or neural demyelination.

Depending on the desired clinical result, the disclosed agents or pharmaceutical compositions are administered by any means suitable for achieving a desired effect. Various delivery methods are known in the art and can be used to deliver an agent to a subject or to NSCs or progenitor cells within a tissue of interest. The delivery method will depend on factors such as the tissue of interest, the nature of the compound (e.g., its stability and ability to cross the blood-brain barrier), and the duration of the experiment or treatment, among other factors. For example, an osmotic minipump can be implanted into a neurogenic region, such as the lateral ventricle. Alternatively, compounds can be administered by direct injection into the cerebrospinal fluid of the brain or spinal column, or into the eye. Compounds can also be administered into the periphery (such as by intravenous or subcutaneous injection, or oral delivery), and subsequently cross the blood-brain barrier.

In some embodiments, the disclosed agents or pharmaceutical compositions are administered in a manner that allows them to contact the subventricular zone (SVZ) of the lateral ventricles and/or the dentate gyrus of the hippocampus. The delivery or targeting of a PDE agent, optionally in combination with one or more other neurogenic agents, to a neurogenic region, such as the dentate gyrus or the subventricular zone, may enhances efficacy and reduces side effects compared to known methods involving administration with the same or similar compounds. Examples of routes of administration include parenteral, e.g., intravenous, intradermal, subcutaneous, oral (e.g., inhalation), transdermal (topical), transmucosal, and rectal administration. Intranasal administration generally includes, but is not limited to, inhalation of aerosol suspensions for delivery of compositions to the nasal mucosa, trachea and bronchioli.

In other embodiments, a combination of a PDE agent, optionally in combination with one or more other neurogenic agents, is administered so as to either pass through or by-pass the blood-brain barrier. Methods for allowing factors to pass through the blood-brain barrier are known in the art, and include minimizing the size of the factor, providing hydrophobic factors which facilitate passage, and conjugation to a carrier molecule that has substantial permeability across the blood brain barrier. In some instances, an agent or combination of agents can be administered by a surgical procedure implanting a catheter coupled to a pump device. The pump device can also be implanted or be extracorporally positioned. Administration of a PDE agent, optionally in combination with one or more other neurogenic agents, can be in intermittent pulses or as a continuous infusion. Devices for injection to discrete areas of the brain are known in the art. In certain embodiments, the combination is administered locally to the ventricle of the brain, substantia nigra, striatum, locus ceruleous, nucleus basalis Meynert, pedunculopontine nucleus, cerebral cortex, and/or spinal cord by, e.g., injection. Methods, compositions, and devices for delivering therapeutics, including therapeutics for the treatment of diseases and conditions of the CNS and PNS, are known in the art.

In some embodiments, a PDE agent and/or other agent(s) in a combination is modified to facilitate crossing of the gut epithelium. For example, in some embodiments, a PDE agent or other agent(s) is a prodrug that is actively transported across the intestinal epithelium and metabolized into the active agent in systemic circulation and/or in the CNS.

In other embodiments, a PDE agent and/or other agent(s) of a combination is conjugated to a targeting domain to form a chimeric therapeutic, where the targeting domain facilitates passage of the blood-brain barrier (as described above) and/or binds one or more molecular targets in the CNS. In some embodiments, the targeting domain binds a target that is differentially expressed or displayed on, or in close proximity to, tissues, organs, and/or cells of interest. In some cases, the target is preferentially distributed in a neurogenic region of the brain, such as the dentate gyrus and/or the SVZ. For example, in some embodiments, a PDE agent and/or other agent(s) of a combination is conjugated or complexed with the fatty acid docosahexaenoic acid (DHA), which is readily transported across the blood brain barrier and imported into cells of the CNS.

Representative Conditions

The disclosure includes methods for treating depression and other neurological diseases and conditions. In some embodiments, a method may comprise use of a combination of a PDE agent and one or more agents reported as antidepressant agents. Thus a method may comprise treatment with a PDE agent and one or more reported anti-depressant agents as known to the skilled person. Non-limiting examples of such agents include an SSRI (selective serotonin reuptake inhibitor), such as fluoxetine (Prozac®; described, e.g., in U.S. Pat. Nos. 4,314,081 and 4,194,009), citalopram (Celexa; described, e.g., in U.S. Pat. No. 4,136,193), escitalopram (Lexapro; described, e.g., in U.S. Pat. No. 4,136,193), fluvoxamine (described, e.g., in U.S. Pat. No. 4,085,225) or fluvoxamine maleate (CAS RN: 61718-82-9) and Luvox®, paroxetine (Paxil®; described, e.g., in U.S. Pat. Nos. 3,912, 743 and 4,007,196), or sertraline (Zoloft®; described, e.g., in U.S. Pat. No. 4,536,518), or alaproclate; the compound nefazodone (Serozone®; described, e.g., in U.S. Pat. No. 4,338, 317). As would be recognized by a skilled person, the effects of these agents is reflected by the effects of serotonin. Additional non-limiting examples of such agents include a selective norepinephrine reuptake inhibitor (SNRI) such as reboxetine (Edronax®), atomoxetine (Strattera®), milnacipran (described, e.g., in U.S. Pat. No. 4,478,836), sibutramine or its primary amine metabolite (BTS 54505), amoxapine, or maprotiline; a selective serotonin & norepinephrine reuptake inhibitor (SSNRI) such as venlafaxine (Effexor; described, e.g., in U.S. Pat. No. 4,761,501), and its reported metabolite desvenlafaxine, or duloxetine (Cymbalta; described, e.g., in U.S. Pat. No. 4,956,388); a serotonin, noradrenaline, and a dopamine "triple uptake inhibitor", such as DOV 102,677 (see Popik et al. "Pharmacological Profile of the "Triple" Monoamine Neurotransmitter Uptake Inhibitor, DOV 102,677." *Cell Mol. Neurobiol.* 2006 Apr. 25; Epub ahead of print), DOV 216,303 (see Beer et al. "DOV 216,303, a "triple" reuptake inhibitor: safety, tolerability, and pharmacokinetic profile." *J Clin Pharmacol.* 2004 44(12):1360-7), DOV 21,947 ((+)-1-(3,4-dichlorophenyl)-3-azabicyclo-(3.1.0)hexane hydrochloride), see Skolnick et al. "Antidepressant-like actions of DOV 21,947: a "triple" reuptake inhibitor." *Eur J. Pharmacol.* 2003 461(2-3):99-104), NS-2330 or tesofensine (CAS RN 402856-42-2), or NS 2359 (CAS RN 843660-54-8);

and agents like dehydroepiandrosterone (DHEA), and DHEA sulfate (DHEAS), CP-122, 721 (CAS RN 145742-28-5).

Additional non-limiting examples of such agents include a tricyclic compound such as clomipramine, dosulepin or dothiepin, lofepramine (described, e.g., in U.S. Pat. No. 4,172,074), trimipramine, protriptyline, amitriptyline, desipramine (described, e.g., in U.S. Pat. No. 3,454,554), doxepin, imipramine, or nortriptyline; a psychostimulant such as dextroamphetamine and methylphenidate; an MAO inhibitor such as selegiline (Emsam®); an ampakine such as CX516 (or Ampalex, CAS RN: 154235-83-3), CX546 (or 1-(1,4-benzodioxan-6-ylcarbonyl)piperidine), and CX614 (CAS RN 191744-13-5) from Cortex Pharmaceuticals; a V1b antagonist such as SSR149415 ((2S,4R)-1-[5-Chloro-1-[(2, 4-dimethoxyphenyl)sulfonyl]-3-(2-methoxy-phenyl)-2-oxo-2,3-dihydro-1H-indol-3-yl]-4-hydroxy-N,N-dimethyl-2-pyrrolidine carboxamide),

[1-(beta-mercapto-beta,beta-cyclopentamethylenepropionic acid), 2-O-ethyltyrosine, 4-valine] arginine vasopressin $(d(CH2)_5[Tyr(Et2)]VAVP$ (WK 1-1), 9-desglycine[1-(beta-mercapto-beta,beta-cyclopentamethylenepropionic acid), 2-O-ethyltyrosine, 4-valine] arginine vasopressin desGly9d(CH2)5 [Tyr(Et2)]-VAVP (WK 3-6), or 9-desglycine[1-(beta-mercapto-beta,beta-cyclopentamethylenepropionic acid),2-D-(O-ethyl)tyrosine, 4-valine] arginine vasopressin des Gly9d(CH2)5[D-Tyr(Et2)]VAVP (AO 3-21); a corticotropin-releasing factor (CRF) R antagonist such as CP-154,526 (structure disclosed in Schulz et al. "CP-154,526: a potent and selective nonpeptide antagonist of corticotropin releasing factor receptors." *Proc Natl Acad Sci USA.* 1996 93(19):10477-82), NBI 30775 (also known as R121919 or 2,5-dimethyl-3-(6-dimethyl-4-methylpyridin-3-yl)-7-dipropylaminopyrazolo[1,5-a]pyrimidine), astressin (CAS RN 170809-51-5), or a photoactivatable analog thereof as described in Bonk et al. "Novel high-affinity photoactivatable antagonists of corticotropin-releasing factor (CRF)" *Eur. J. Biochem.* 267:3017-3024 (2000), or AAG561 (from Novartis); a melanin concentrating hormone (MCH) antagonist such as 3,5-dimethoxy-N-(1-(naphthalen-2-ylmethyl)piperidin-4-yl)benzamide or (R)-3,5-dimethoxy-N-(1-(naphthalen-2-ylmethyl)-pyrrolidin-3-yl)benzamide (see Kim et al. "Identification of substituted 4-aminopiperidines and 3-aminopyrrolidines as potent MCH-R1 antagonists for the treatment of obesity." *Bioorg Med Chem. Lett.* 2006 Jul. 29; [Epub ahead of print] for both), or any MCH antagonist disclosed in U.S. Pat. No. 7,045,636 or published U.S. Patent Application US2005/0171098.

Further non-limiting examples of such agents include a tetracyclic compound such as mirtazapine (described, e.g., in U.S. Pat. No. 4,062,848; see CAS RN 61337-67-5; also known as Remeron, or CAS RN 85650-52-8), mianserin (described, e.g., in U.S. Pat. No. 3,534,041), or setiptiline.

Further non-limiting examples of such agents include agomelatine (CAS RN 138112-76-2), pindolol (CAS RN 13523-86-9), antalarmin (CAS RN 157284-96-3), mifepristone (CAS RN 84371-65-3), nemifitide (CAS RN 173240-15-8) or nemifitide ditriflutate (CAS RN 204992-09-6), YKP-10A or R228060 (CAS RN 561069-23-6), trazodone (CAS RN 19794-93-5), bupropion (CAS RN 34841-39-9 or 34911-55-2) or bupropion hydrochloride (or Wellbutrin, CAS RN 31677-93-7) and its reported metabolite radafaxine (CAS RN 192374-14-4), NS2359 (CAS RN 843660-54-8), Org 34517 (CAS RN 189035-07-2), Org 34850 (CAS RN 162607-84-3), vilazodone (CAS RN 163521-12-8), CP-122,721 (CAS RN 145742-28-5), gepirone (CAS RN 83928-76-1), SR58611 (see Mizuno et al. "The stimulation of beta(3)-adrenoceptor causes phosphorylation of extracellular signal-regulated kinases 1 and 2 through a G(s)-but not G(i)-dependent pathway in 3T3-L1 adipocytes."*Eur J. Pharmacol.* 2000 404(1-2):63-8), saredutant or SR 48968 (CAS RN 142001-63-6), PRX-00023 (N-{3-[4-(4-cyclohexylmethanesulfonylaminobutyl)piperazin-1-yl]phenyl}acetamide, see Becker et al. "An integrated in silico 3D model-driven discovery of a novel, potent, and selective amidosulfonamide 5-HT1A agonist (PRX-00023) for the treatment of anxiety and depression." *J Med. Chem.* 2006 49(11):3116-35), Vestipitant (or GW597599, CAS RN 334476-46-9), OPC-14523 or VPI-013 (see Bermack et al. "Effects of the potential antidepressant OPC-14523 [1-[3-[4-(3-chlorophenyl)-1-piperazinyl] propyl]-5-methoxy-3,4-dihydro-2-quinolinone monomethanesulfonate] a combined sigma and 5-HT1A ligand: modulation of neuronal activity in the dorsal raphe nucleus." *J Pharmacol Exp Ther.* 2004 310(2):578-83), Casopitant or GW679769 (CAS RN 852393-14-7), Elzasonan or CP-448,187 (CAS RN 361343-19-3), GW823296 (see published U.S. Patent Application US2005/0119248), Delucemine or NPS 1506 (CAS RN 186495-49-8), or Ocinaplon (CAS RN 96604-21-6).

Yet additional non-limiting examples of such agents include CX717 from Cortex Pharmaceuticals, TGBA01AD (a serotonin reuptake inhibitor, 5-HT2 agonist, 5-HT1A agonist, and 5-HT1D agonist) from Fabre-Kramer Pharmaceuticals, Inc., ORG 4420 (an NaSSA (noradrenergic/specific serotonergic antidepressant) from Organon, CP-316,311 (a CRF1 antagonist) from Pfizer, BMS-562086 (a CRF1 antagonist) from Bristol-Myers Squibb, GW876008 (a CRF1 antagonist) from Neurocrine/GlaxoSmithKline, ONO-2333Ms (a CRF1 antagonist) from Ono Pharmaceutical Co., Ltd., JNJ-19567470 or TS-041 (a CRF1 antagonist) from Janssen (Johnson & Johnson) and Taisho, SSR 125543 or SSR 126374 (a CRF1 antagonist) from Sanofi-Aventis, Lu AA21004 and Lu AA24530 (both from H. Lundbeck A/S), SEP-225289 from Sepracor Inc., ND7001 (a PDE2 inhibitor) from Neuro3d, SSR 411298 or SSR 101010 (a fatty acid amide hydrolase, or FAAH, inhibitor) from Sanofi-Aventis, 163090 (a mixed serotonin receptor inhibitor) from GlaxoSmithKline, SSR 241586 (an NK2 and NK3 receptor antagonist) from Sanofi-Aventis, SAR 102279 (an NK2 receptor antagonist) from Sanofi-Aventis, YKP581 from SK Pharmaceuticals (Johnson & Johnson), R1576 (a GPCR modulator) from Roche, or ND1251 (a PDE4 inhibitor) from Neuro3d.

In other embodiments, a method may comprise use of a combination of a PDE agent and one or more agents reported as anti-psychotic agents. Non-limiting examples of a reported anti-psychotic agent as a member of a combination include olanzapine, quetiapine (Seroquel), clozapine (CAS RN 5786-21-0) or its metabolite ACP-104 (N-desmethylclozapine or norclozapine, CAS RN 6104-71-8), reserpine, aripiprazole, risperidone, ziprasidone, sertindole, trazodone, paliperidone (CAS RN 144598-75-4), mifepristone (CAS RN 84371-65-3), bifeprunox or DU-127090 (CAS RN 350992-10-8), asenapine or ORG 5222 (CAS RN 65576-45-6), iloperidone (CAS RN 133454-47-4), ocaperidone (CAS RN 129029-23-8), SLV 308 (CAS RN 269718-83-4), licarbazepine or GP 47779 (CAS RN 29331-92-8), Org 34517 (CAS RN 189035-07-2), ORG 34850 (CAS RN 162607-84-3), Org 24448 (CAS RN 211735-76-1), lurasidone (CAS RN 367514-87-2), blonanserin or lonasen (CAS RN 132810-10-7), Talnetant or SB-223412 (CAS RN 174636-32-9), secretin (CAS RN 1393-25-5) or human secretin (CAS RN 108153-74-8) which are endogenous pancreatic hormones, ABT 089 (CAS RN 161417-03-4), SSR 504734 (see compound 13 in Hashimoto "Glycine Transporter Inhibitors as Therapeutic Agents for Schizophrenia." *Recent Patents on CNS Drug Discovery*, 2006 1:43-53), MEM 3454 (see Mazurov et al. "Selective alpha7 nicotinic acetylcholine receptor ligands." *Curr Med. Chem.* 2006 13(13):1567-84), a phosphodiesterase 10A (PDE10A) inhibitor such as papaverine (CAS RN 58-74-2) or papaverine hydrochloride (CAS RN 61-25-6), paliperidone (CAS RN 144598-75-4), trifluoperazine (CAS RN 117-89-5), or trifluoperazine hydrochloride (CAS RN 440-17-5).

Additional non-limiting examples of such agents include trifluoperazine, fluphenazine, chlorpromazine, perphenazine, thioridazine, haloperidol, loxapine, mesoridazine, molindone, pimoxide, or thiothixene, SSR 146977 (see Emonds-Alt et al. "Biochemical and pharmacological activities of SSR 146977, a new potent nonpeptide tachykinin NK3 receptor antagonist." *Can J Physiol Pharmacol.* 2002 80(5):482-8), SSR181507 ((3-exo)-8-benzoyl-N—[[(2 s)7-chloro-2,3-dihydro-1,4-benzodioxin-1-yl]methyl]-8-azabicyclo[3.2.1]octane-3-methanamine monohydrochloride), or SLV313 (1-(2, 3-dihydro-benzo[1,4]dioxin-5-yl)-4-[5-(4-fluorophenyl)-pyridin-3-ylmethyl]-piperazine).

Further non-limiting examples of such agents include Lu-35-138 (a D4/5-HT antagonist) from Lundbeck, AVE 1625 (a CB1 antagonist) from Sanofi-Aventis, SLV 310,313 (a 5-HT2A antagonist) from Solvay, SSR 181507 (a D2/5-HT2 antagonist) from Sanofi-Aventis, GW07034 (a 5-HT6 antagonist) or GW773812 (a D2,5-HT antagonist) from GlaxoSmithKline, YKP 1538 from SK Pharmaceuticals, SSR 125047 (a sigma receptor antagonist) from Sanofi-Aventis, MEM1003 (a L-type calcium channel modulator) from Memory Pharmaceuticals, JNJ-17305600 (a GLYT1 inhibitor) from Johnson & Johnson, XY 2401 (a glycine site specific NMDA modulator) from Xytis, PNU 170413 from Pfizer, RGH-188 (a D2, D3 antagonist) from Forrest, SSR 180711 (an alpha7 nicotinic acetylcholine receptor partial agonist) or SSR 103800 (a GLYT1 (Type 1 glycine transporter) inhibitor) or SSR 241586 (a NK3 antagonist) from Sanofi-Aventis.

In other disclosed embodiments, a reported anti-psychotic agent may be one used in treating schizophrenia. Non-limiting examples of a reported anti-schizophrenia agent as a member of a combination with a PDE agent include molindone hydrochloride (MOBAN®) and TC-1827 (see Bohme et al. "In vitro and in vivo characterization of TC-1827, a novel brain α4β2 nicotinic receptor agonist with pro-cognitive activity." *Drug Development Research* 2004 62(1):26-40).

In some embodiments, a method may comprise use of a combination of a PDE agent and one or more agents reported for treating weight gain, metabolic syndrome, or obesity, and/or to induce weight loss or prevent weight gain. Non-limiting examples of the reported agent include various diet pills that are commercially or clinically available. In some embodiments, the reported agent is orlistat (CAS RN 96829-58-2), sibutramine (CAS RN 106650-56-0) or sibutramine hydrochloride (CAS RN 84485-00-7), phetermine (CAS RN 122-09-8) or phetermine hydrochloride (CAS RN 1197-21-3), diethylpropion or amfepramone (CAS RN 90-84-6) or diethylpropion hydrochloride, benzphetamine (CAS RN 156-08-1) or benzphetamine hydrochloride, phendimetrazine (CAS RN 634-03-7 or 21784-30-5) or phendimetrazine hydrochloride (CAS RN 17140-98-6) or phendimetrazine tartrate, rimonabant (CAS RN 168273-06-1), bupropion hydrochloride (CAS RN: 31677-93-7), topiramate (CAS RN 97240-79-4), zonisamide (CAS RN 68291-97-4), or APD-356 (CAS RN 846589-98-8).

In other non-limiting embodiments, the agent may be fenfluramine or Pondimin (CAS RN 458-24-2), dexfenfluramine or Redux (CAS RN 3239-44-9), or levofenfluramine (CAS RN 37577-24-5); or a combination thereof or a combination with phentermine. Non-limiting examples include a combination of fenfluramine and phentermine (or "fen-phen") and of dexfenfluramine and phentermine (or "dexfen-phen").

The combination therapy may be of one of the above with a PDE agent as described herein to improve the condition of the subject or patient. Non-limiting examples of combination therapy include the use of lower dosages of the above additional agents, or combinations thereof, which reduce side effects of the agent or combination when used alone. For example, an anti-depressant agent like fluoxetine or paroxetine or sertraline may be administered at a reduced or limited dose, optionally also reduced in frequency of administration, in combination with a PDE agent.

Similarly, a combination of fenfluramine and phentermine, or phentermine and dexfenfluramine, may be administered at a reduced or limited dose, optionally also reduced in frequency of administration, in combination with a PDE agent. The reduced dose or frequency may be that which reduces or eliminates the side effects of the combination.

In light of the positive recitation (above and below) of combinations with alternative agents to treat conditions disclosed herein, the disclosure includes embodiments with the explicit exclusion of one or more of the alternative agents or one or more types of alternative agents. As would be recognized by the skilled person, a description of the whole of a plurality of alternative agents (or classes of agents) necessarily includes and describes subsets of the possible alternatives, such as the part remaining with the exclusion of one or more of the alternatives or exclusion of one or more classes.

Representative Combinations

As indicated herein, the disclosure includes combination therapy, where a PDE agent in combination with one or more other neurogenic agents is used to produce neurogenesis. When administered as a combination, the therapeutic compounds can be formulated as separate compositions that are administered at the same time or sequentially at different times, or the therapeutic compounds can be given as a single composition. The methods of the disclosure are not limited in the sequence of administration.

Instead, the disclosure includes methods wherein treatment with a PDE agent and another neurogenic agent occurs over a period of more than about 48 hours, more than about 72 hours, more than about 96 hours, more than about 120 hours, more than about 144 hours, more than about 7 days, more than about 9 days, more than about 11 days, more than about 14 days, more than about 21 days, more than about 28 days, more than about 35 days, more than about 42 days, more than about 49 days, more than about 56 days, more than about 63 days, more than about 70 days, more than about 77 days, more than about 12 weeks, more than about 16 weeks, more than about 20 weeks, or more than about 24 weeks or more. In some embodiments, treatment by administering a PDE agent, occurs at least about 12 hours, such as at least about 24, or at least about 36 hours, before administration of another neurogenic agent. Following administration of a PDE agent, further administrations may be of only the other neurogenic agent in some embodiments of the disclosure. In other embodiments, further administrations may be of only the PDE agent.

In some cases, combination therapy with a PDE agent and one or more additional agents results in a enhanced efficacy, safety, therapeutic index, and/or tolerability, and/or reduced side effects (frequency, severity, or other aspects), dosage levels, dosage frequency, and/or treatment duration. Examples of compounds useful in combinations described herein are provided above and below. Structures, synthetic processes, safety profiles, biological activity data, methods for determining biological activity, pharmaceutical preparations, and methods of administration relating to the compounds are known in the art and/or provided in the cited references, all of which are herein incorporated by reference in their entirety. Dosages of compounds administered in combination with a PDE agent can be, e.g., a dosage within the range of pharmacological dosages established in humans, or a dosage that is a fraction of the established human dosage, e.g., 70%, 50%, 30%, 10%, or less than the established human dosage.

In some embodiments, the neurogenic agent combined with a PDE agent may be a reported opioid or non-opioid (acts independently of an opioid receptor) agent. In some embodiments, the neurogenic agent is one reported as antagonizing one or more opioid receptors or as an inverse agonist of at least one opioid receptor. A opioid receptor antagonist or inverse agonist may be specific or selective (or alternatively non-specific or non-selective) for opioid receptor subtypes. So an antagonist may be non-specific or non-selective such that it antagonizes more than one of the three known opioid receptor subtypes, identified as $OP_1$, $OP_2$, and $OP_3$ (also know as delta, or δ, kappa, or κ, and mu, or μ, respectively). Thus an opioid that antagonizes any two, or all three, of these subtypes, or an inverse agonist that is specific or selective for any two or all three of these subtypes, may be used as the neurogenic agent in the practice. Alternatively, an antagonist or inverse agonist may be specific or selective for one of the three subtypes, such as the kappa subtype as a non-limiting example.

Non-limiting examples of reported opioid antagonists include naltrindol, naloxone, naloxene, naltrexone, JDTic (Registry Number 785835-79-2; also known as 3-isoquinolinecarboxamide, 1,2,3,4-tetrahydro-7-hydroxy-N-[(1S)-1-[[(3R,4R)-4-(3-hydroxyphenyl)-3,4-dimethyl-1-piperidinyl] methyl]-2-methylpropyl]-dihydrochloride, (3R)-(9CI)), norbinaltorphimine, and buprenorphine. In some embodiments, a reported selective kappa opioid receptor antagonist compound, as described in US 20020132828, U.S. Pat. No. 6,559, 159, and/or WO 2002/053533, may be used. All three of these documents are herein incorporated by reference in their entireties as if fully set forth. Further non-limiting examples of such reported antagonists is a compound disclosed in U.S. Pat. No. 6,900,228 (herein incorporated by reference in its entirety), arodyn (Ac[Phe(1,2,3),Arg(4),d-Ala(8)]Dyn A-(1-11)NH(2), as described in Bennett, et al. (2002) *J. Med. Chem.* 45:5617-5619), and an active analog of arodyn as described in Bennett e al. (2005) J Pept Res. 65(3):322-32, alvimopan.

In some embodiments, the neurogenic agent used in the methods described herein has "selective" activity (such as in the case of an antagonist or inverse agonist) under certain conditions against one or more opioid receptor subtypes with respect to the degree and/or nature of activity against one or more other opioid receptor subtypes. For example, in some embodiments, the neurogenic agent has an antagonist effect against one or more subtypes, and a much weaker effect or substantially no effect against other subtypes. As another example, an additional neurogenic agent used in the methods described herein may act as an agonist at one or more opioid receptor subtypes and as antagonist at one or more other opioid receptor subtypes. In some embodiments, a neurogenic agent has activity against kappa opioid receptors, while having substantially lesser activity against one or both of the delta and mu receptor subtypes. In other embodiments, a neurogenic agent has activity against two opioid receptor subtypes, such as the kappa and delta subtypes. As non-limiting examples, the agents naloxone and naltrexone have nonselective antagonist activities against more than one opioid receptor subtypes. In certain embodiments, selective activity of one or more opioid antagonists results in enhanced efficacy, fewer side effects, lower effective dosages, less frequent dosing, or other desirable attributes.

An opioid receptor antagonist is an agent able to inhibit one or more characteristic responses of an opioid receptor or receptor subtype. As a non-limiting example, an antagonist may competitively or non-competitively bind to an opioid receptor, an agonist or partial agonist (or other ligand) of a receptor, and/or a downstream signaling molecule to inhibit a receptor's function.

An inverse agonist able to block or inhibit a constitutive activity of an opioid receptor may also be used. An inverse agonist may competitively or non-competitively bind to an opioid receptor and/or a downstream signaling molecule to inhibit a receptor's function. Non-limiting examples of inverse agonists for use in the disclosed methods include ICI-174864 (N,N-diallyl-Tyr-Aib-Aib-Phe-Leu), RTI-5989-1, RTI-5989-23, and RTI-5989-25 (see Zaki et al. *J. Pharmacol. Exp. Therap.* 298(3): 1015-1020, 2001).

Additional embodiments of the disclosure include a combination of a PDE agent with an additional agent such as acetylcholine or a reported modulator of an androgen receptor. Non-limiting examples include the androgen receptor agonists ehydroepiandrosterone (DHEA) and DHEA sulfate (DHEAS).

Alternatively, the neurogenic agent in combination with a PDE agent may be an enzymatic inhibitor, such as a reported inhibitor of HMG CoA reductase. Non-limiting examples of such inhibitors include atorvastatin (CAS RN 134523-00-5), cerivastatin (CAS RN 145599-86-6), crilvastatin (CAS RN 120551-59-9), fluvastatin (CAS RN 93957-54-1) and fluvastatin sodium (CAS RN 93957-55-2), simvastatin (CAS RN 79902-63-9), lovastatin (CAS RN 75330-75-5), pravastatin (CAS RN 81093-37-0) or pravastatin sodium, rosuvastatin (CAS RN 287714-41-4), and simvastatin (CAS RN 79902-63-9). Formulations containing one or more of such inhibitors may also be used in a combination. Non-limiting examples include formulations comprising lovastatin such as Advicor (an extended-release, niacin containing formulation) or Altocor (an extended release formulation); and formulations comprising simvastatin such as Vytorin (combination of simvastatin and ezetimibe).

In other non-limiting embodiments, the neurogenic agent in combination with a PDE agent may be a reported Rho kinase inhibitor. Non-limiting examples of such an inhibitor include fasudil (CAS RN 103745-39-7); fasudil hydrochloride (CAS RN 105628-07-7); the metabolite of fasudil, which is hydroxyfasudil (see Shimokawa et al. "Rho-kinase-mediated pathway induces enhanced myosin light chain phosphorylations in a swine model of coronary artery spasm." *Cardiovasc Res.* 1999 43:1029-1039), Y 27632 (CAS RN 138381-45-0); a fasudil analog thereof such as (S)-Hexahydro-1-(4-ethenylisoquinoline-5-sulfonyl)-2-methyl-1H-1,4-diazepine, (S)-hexahydro-4-glycyl-2-methyl-1-(4-methylisoquinoline-5-sulfonyl)-1H-1,4-diazepine, or (S)-(+)-2-methyl-1-[(4-methyl-5-isoquinoline)sulfonyl]-homopiperazine (also known as H-1152P; see Sasaki et al. "The novel and specific Rho-kinase inhibitor (S)-(+)-2-methyl-1-[(4-methyl-5-isoquinoline)sulfonyl]-homopiperazine as a probing molecule for Rho-kinase-involved pathway." *Pharmacol Ther.* 2002 93(2-3):225-32); or a substituted isoquinolinesulfonamide compound as disclosed in U.S. Pat. No. 6,906,061.

Furthermore, the neurogenic agent in combination with a PDE agent may be a reported GSK-3 inhibitor or modulator. In some non-limiting embodiments, the reported GSK3-beta modulator is a paullone, such as alsterpaullone, kenpaullone (9-bromo-7,12-dihydroindolo[3,2-d][1]benzazepin-6(5H)-one), gwennpaullone (see Knockaert et al. "Intracellular Targets of Paullones. Identification following affinity purification on immobilized inhibitor." *J Biol. Chem.* 2002 277(28): 25493-501), azakenpaullone (see Kunick et al. "1-Azakenpaullone is a selective inhibitor of glycogen synthase kinase-3 beta." *Bioorg Med Chem. Lett.* 2004 14(2): 413-6), or the compounds described in U.S. Publication No. 20030181439; International Publication No. WO 01/60374; Leost et al., *Eur. J. Biochem.* 267:5983-5994 (2000); Kunick et al., J Med. Chem.; 47(1): 22-36 (2004); or Shultz et al., J. Med. Chem. 42:2909-2919 (1999); an anticonvulsant, such as lithium or a derivative thereof (e.g., a compound described in U.S. Pat. Nos. 1,873,732; 3,814,812; and 4,301,176); valproic acid or a derivative thereof (e.g., valproate, or a compound described in Werstuck et al., Bioorg Med Chem. Lett., 14(22): 5465-7 (2004)); lamotrigine; SL 76002 (Progabide), Gabapentin; tiagabine; or vigabatrin; a maleimide or a related compound, such as Ro 31-8220, SB-216763, SB-410111, SB-495052, or SB-415286, or a compound described, e.g., in U.S. Pat. No. 6,719,520; U.S. Publication No. 20040010031; International Publication Nos. WO-2004072062; WO-03082859; WO-03104222; WO-03103663, WO-03095452, WO-2005000836; WO 0021927; WO-03076398; WO-00021927; WO-00038675; or WO-03076442; or Coghlan et al., Chemistry & Biology 7: 793 (2000); a pyridine or pyrimidine derivative, or a related compound (such as 5-iodotubercidin, GI 179186X, GW 784752x and GW 784775X, and compounds described, e.g., in U.S. Pat. Nos. 6,489,344; 6,417,185; and 6,153,618; U.S. Publication Nos. 20050171094; and 20030130289; European Patent Nos. EP-01454908, EP-01454910, EP-01295884, EP-01295885; and EP-01460076; EP-01454900; International Publication Nos. WO 01/70683; WO 01/70729; WO 01/70728; WO 01/70727; WO 01/70726; WO 01/70725; WO-00218385; WO-00218386; WO-03072579; WO-03072580; WO-03027115; WO-03027116; WO-2004078760; WO-2005037800, WO-2004026881, WO-03076437, WO-03029223; WO-2004098607; WO-2005026155; WO-2005026159; WO-2005025567; WO-03070730; WO-03070729; WO-2005019218; WO-2005019219; WO-2004013140; WO-2004080977; WO-2004026229, WO-2004022561; WO-03080616; WO-03080609; WO-03051847; WO-2004009602; WO-2004009596; WO-2004009597; WO-03045949; WO-03068773; WO-03080617; WO 99/65897; WO 00/18758; WO0307073; WO-00220495; WO-2004043953, WO-2004056368, WO-2005012298, WO-2005012262, WO-2005042525, WO-2005005438, WO-2004009562, WO-03037877; WO-03037869; WO-03037891; WO-05012307; WO-05012304 and WO 98/16528; and in Massillon et al., Biochem J 299:123-8 (1994)); a pyrazine derivative, such as Aloisine A (7-n-Butyl-6-(4-hydroxyphenyl)[5H]pyrrolo[2,3-b]pyrazine) or a compound described in International Publication Nos. WO-00144206; WO0144246; or WO-2005035532; a thiadiazole or thiazole, such as TDZD-8 (Benzyl-2-methyl-1,2,4-thiadiazolidine-3,5-dione); OTDZT (4-Dibenzyl-5-oxothiadiazolidine-3-thione); or a related compound described, e.g., in U.S. Pat. No. 6,645, 990 or 6,762,179; U.S. Publication No. 20010039275; International Publication Nos. WO 01/56567, WO-03011843, WO-03004478, or WO-03089419; or Mettey, Y., et al., J. Med. Chem. 46, 222 (2003); TWS119 or a related compound, such as a compound described in Ding et al., Proc Natl Acad Sci U S A., 100(13): 7632-7 (2003); an indole derivative, such as a compound described in International Publication Nos. WO-03053330, WO-03053444, WO-03055877, WO-03055492, WO-03082853, or WO-2005027823; a pyrazine or pyrazole derivative, such as a compound described in U.S. Pat. Nos. 6,727,251, 6,696,452, 6,664,247, 6,660,73, 6,656,939, 6,653,301, 6,653,300, 6,638,926, 6,613,776, or 6,610,677; or International Publication Nos. WO-2005002552, WO-2005002576, or WO-2005012256; a compound described in U.S. Pat. Nos. 6,719,520; 6,498,176;

6,800,632; or 6,872,737; U.S. Publication Nos. 20050137201; 20050176713; 20050044125; 20040010031; 20030105075; 20030008866; 20010044436; 20040138273; or 20040214928; International Publication Nos. WO 99/21859; WO-00210158; WO-05051919; WO-00232896; WO-2004046117; WO-2004106343; WO-00210141; WO-00218346; WO 00/21927; WO 01/81345; WO 01/74771; WO 05/028475; WO 01/09106; WO 00/21927; WO 01/41768; WO 00/17184; WO 04/037791; WO-04065370; WO 01/37819; WO 01/42224; WO 01/85685; WO 04/072063; WO-2004085439; WO-2005000303; WO-2005000304; or WO 99/47522; or Naerum, L., et al., Bioorg. Med. Chem. Lett. 12, 1525 (2002); CP-79049, GI 179186X, GW 784752X, GW 784775X, AZD-1080, AR-014418, SN-8914, SN-3728, OTDZT, Aloisine A, TWS119, CHIR98023, CHIR99021, CHIR98014, CHIR98023, 5-iodotubercidin, Ro 31-8220, SB-216763, SB-410111, SB-495052, SB-415286, alsterpaullone, kenpaullone, gwennpaullone, LY294002, wortmannin, sildenafil, CT98014, CT-99025, flavoperidol, or L803-mts.

In yet further embodiments, the neurogenic agent used in combination with a PDE agent may be a reported glutamate modulator or metabotropic glutamate (mGlu) receptor modulator. In some embodiments, the reported mGlu receptor modulator is a Group II modulator, having activity against one or more Group II receptors ($mGlu_2$ and/or $mGlu_3$). Embodiments include those where the Group II modulator is a Group II agonist. Non-limiting examples of Group II agonists include: (i) (1S,3R)-1-aminocyclopentane-1,3-dicarboxylic acid (ACPD), a broad spectrum mGlu agonist having substantial activity at Group I and II receptors; (ii) (−)-2-thia-4-aminobicyclo-hexane-4,6-dicarboxylate (LY389795), which is described in Monn et al., J. Med. Chem., 42(6):1027-40 (1999); (iii) compounds described in US App. No. 20040102521 and Pellicciari et al., J. Med. Chem., 39, 2259-2269 (1996); and (iv) the Group II-specific modulators described below.

Non-limiting examples of reported Group II antagonists include: (i) phenylglycine analogues, such as (RS)-alpha-methyl-4-sulphonophenylglycine (MSPG), (RS)-alpha-methyl-4-phosphonophenylglycine (MPPG), and (RS)-alpha-methyl-4-tetrazolylphenylglycine (MTPG), described in Jane et al., Neuropharmacolog 34: 851-856 (1995); (ii) LY366457, which is described in O'Neill et al., Neuropharmacol., 45(5): 565-74 (2003); (iii) compounds described in US App Nos. 20050049243, 20050119345 and 20030157647; and (iv) the Group II-specific modulators described below.

In some non-limiting embodiments, the reported Group II modulator is a Group II-selective modulator, capable of modulating $mGlu_2$ and/or $mGlu_3$ under conditions where it is substantially inactive at other mGlu subtypes (of Groups I and III). Examples of Group II-selective modulators include compounds described in Monn, et al., J. Med. Chem., 40, 528-537 (1997); Schoepp, et al., Neuropharmacol., 36, 1-11 (1997) (e.g., 1S,2S,5R,6S-2-aminobicyclohexane-2,6-dicarboxylate); and Schoepp, Neurochem. Int., 24, 439 (1994).

Non-limiting examples of reported Group II-selective agonists include (i) (+)-2-aminobicyclohexane-2,6-dicarboxylic acid (LY354740), which is described in Johnson et al., Drug Metab. Disposition, 30(1): 27-33 (2002) and Bond et al., NeuroReport 8: 1463-1466 (1997), and is systemically active after oral administration (e.g., Grillon et al., Psychopharmacol. (Berl), 168: 446-454 (2003)); (ii) (−)-2-Oxa-4-aminobicyclohexane-4,6-dicarboxylic acid (LY379268), which is described in Monn et al., J. Med. Chem. 42: 1027-1040 (1999) and U.S. Pat. No. 5,688,826. LY379268 is readily permeable across the blood-brain barrier, and has $EC_{50}$ values in the low nanomolar range (e.g., below about 10 nM, or below about 5 nM) against human $mGlu_2$ and $mGlu_3$ receptors in vitro; (iii) (2R,4R)-4-aminopyrrolidine-2,4-dicarboxylate ((2R,4R)-APDC), which is described in Monn et al., J. Med. Chem. 39: 2990 (1996) and Schoepp et al., Neuropharmacology, 38: 1431 (1999); (iv) (1S,3S)-1-aminocyclopentane-1,3-dicarboxylic acid ((1S,3S)-ACPD), described in Schoepp, Neurochem. Int., 24: 439 (1994); (v) (2R,4R)-4-aminopyrrolidine-2,4-dicarboxylic acid ((2R,4R)-APDC), described in Howson and Jane, British Journal of Pharmacology, 139, 147-155 (2003); (vi) (2S,1'S,2'S)-2-(carboxycyclopropyl)-glycine (L-CCG-I), described in Brabet et al., Neuropharmacology 37: 1043-1051 (1998); (vii) (2S,2'R,3'R)-2-(2',3'-dicarboxycyclopropyl)glycine (DCG-IV), described in Hayashi et al., Nature, 366, 687-690 (1993); (viii) 1S,2S,5R, 6S-2-aminobicyclohexane-2,6-dicarboxylate, described in Monn, et al., J. Med. Chem., 40, 528 (1997) and Schoepp, et al., Neuropharmacol., 36, 1 (1997); and (vii) compounds described in US App. No. 20040002478; U.S. Pat. Nos. 6,204,292, 6,333,428, 5,750,566 and 6,498,180; and Bond et al., Neuroreport 8: 1463-1466 (1997).

Non-limiting examples of reported Group II-selective antagonists useful in methods provided herein include the competitive antagonist (2S)-2-amino-2-(1S,2S-2-carboxycyclopropyl)-3-(xanth-9-yl)propanoic acid (LY341495), which is described, e.g., in Kingston et al., Neuropharmacology 37: 1-12 (1998) and Monn et al., J Med Chem 42: 1027-1040 (1999). LY341495 is readily permeably across the blood-brain barrier, and has $IC_{50}$ values in the low nanomolar range (e.g., below about 10 nM, or below about 5 nM) against cloned human $mGlu_2$ and $mGlu_3$ receptors. LY341495 has a high degree of selectivity for Group II receptors relative to Group I and Group III receptors at low concentrations (e.g., nanomolar range), whereas at higher concentrations (e.g., above 1 μM), LY341495 also has antagonist activity against $mGlu_7$ and $mGlu_8$, in addition to $mGlu_{2/3}$. LY341495 is substantially inactive against KA, AMPA, and NMDA iGlu receptors.

Additional non-limiting examples of reported Group II-selective antagonists include the following compounds, indicated by chemical name and/or described in the cited references: (i) α-methyl-L-(carboxycyclopropyl) glycine (CCG); (ii) (2S,3 S,4S)-2-methyl-2-(carboxycyclopropyl) glycine (MCCG); (iii) (1R,2R,3R,5R,6R)-2-amino-3-(3,4-dichlorobenzyloxy)-6 fluorobicyclohexane-2,6-dicarboxylic acid (MGS0039), which is described in Nakazato et al., J. Med. Chem., 47(18):4570-87 (2004); (iv) an n-hexyl, n-heptyl, n-octyl, 5-methylbutyl, or 6-methylpentyl ester prodrug of MGS0039; (v) MGS0210 (3-(3,4-dichlorobenzyloxy)-2-amino-6-fluorobicyclohexane-2,6-dicarboxylic acid n-heptyl ester); (vi) (RS)-1-amino-5-phosphonoindan-1-carboxylic acid (APICA), which is described in Ma et al., Bioorg. Med. Chem. Lett., 7: 1195 (1997); (vii) (2S)-ethylglutamic acid (EGLU), which is described in Thomas et al., Br. J. Pharmacol. 117: 70P (1996); (viii) (2S,1'S,2'S,3'R)-2-(2'-carboxy-3'-phenylcyclopropyl)glycine (PCCG-IV); and (ix) compounds described in U.S. Pat. No. 6,107,342 and US App No. 20040006114. APICA has an $IC_{50}$ value of approximately 30 μM against $mGluR_2$ and $mGluR_3$, with no appreciable activity against Group I or Group III receptors at sub-mM concentrations.

In some non-limiting embodiments, a reported Group II-selective modulator is a subtype-selective modulator, capable of modulating the activity of $mGlu_2$ under conditions in which it is substantially inactive at $mGlu_3$ ($mGlu_2$-selective), or vice versa ($mGlu_3$-selective). Non-limiting examples of subtype-selective modulators include compounds described in U.S. Pat. No. 6,376,532 (mGlu$_2$-selective agonists) and US App No. 20040002478 (mGlu$_3$-selective agonists). Additional non-limiting examples of subtype-selective modulators include allosteric mGlu receptor modulators (mGlu$_2$ and mGlu$_3$) and NAAG-related compounds (mGlu$_3$), such as those described below.

In other non-limiting embodiments, a reported Group II modulator is a compound with activity at Group I and/or Group III receptors, in addition to Group II receptors, while having selectivity with respect to one or more mGlu receptor subtypes. Non-limiting examples of such compounds include: (i) (2S,3S,4S)-2-(carboxyeyclopropyl)glycine (L-CCG-1) (Group I/Group II agonist), which is described in Nicoletti et al., *Trends Neurosci.* 19: 267-271 (1996), Nakagawa, et al., *Eur. J. Pharmacol.*, 184, 205 (1990), Hayashi, et al., *Br. J. Pharmacol.*, 107, 539 (1992), and Schoepp et al., *J. Neurochem.*, 63., page 769-772 (1994); (ii) (S)-4-carboxy-3-hydroxyphenylglycine (4C$_3$HPG) (Group II agonist/Group I competitive antagonist); (iii) gamma-carboxy-L-glutamic acid (GLA) (Group II antagonist/Group III partial agonist/antagonist); (iv) (2S,2'R,3'R)-2-(2,3-dicarboxycyclopropyl)glycine (DCG-IV) (Group II agonist/Group III antagonist), which is described in Ohfune et al., *Bioorg. Med. Chem. Lett.*, 3: 15 (1993); (v) (RS)-a-methyl-4-carboxyphenylglycine (MCPG) (Group I/Group II competitive antagonist), which is described in Eaton et al., *Eur. J. Pharmacol.*, 244: 195 (1993), Collingridge and Watkins, *TiPS,* 15: 333 (1994), and Joly et al., *J. Neurosci.*, 15: 3970 (1995); and (vi) the Group II/III modulators described in U.S. Pat. Nos. 5,916,920, 5,688,826, 5,945,417, 5,958,960, 6,143,783, 6,268,507, 6,284,785.

In some non-limiting embodiments, the reported mGlu receptor modulator comprises (S)-MCPG (the active isomer of the Group I/Group II competitive antagonist (RS)-MCPG) substantially free from (R)-MCPG. (S)-MCPG is described, e.g., in Sekiyama et al., *Br. J. Pharmacol.*, 117: 1493 (1996) and Collingridge and Watkins, *TiPS,* 15: 333 (1994).

Additional non-limiting examples of reported mGlu modulators useful in methods disclosed herein include compounds described in U.S. Pat. Nos. 6,956,049, 6,825,211, 5,473,077, 5,912,248, 6,054,448, and 5,500,420; US App Nos. 20040077599, 20040147482, 20040102521, 20030199533 and 20050234048; and Intl Pub/App Nos. WO 97/19049, WO 98/00391, and EP0870760.

In some non-limiting embodiments, the reported mGlu receptor modulator is a prodrug, metabolite, or other derivative of N-Acetylaspartylglutamate (NAAG), a peptide neurotransmitter in the mammalian CNS that is a highly selective agonist for mGluR$_3$ receptors, as described in Wroblewska et al., *J. Neurochem.,* 69(1): 174-181 (1997). In other embodiments, the mGlu modulator is a compound that modulates the levels of endogenous NAAG, such as an inhibitor of the enzyme N-acetylated-alpha-linked-acidic dipeptidase (NAALADase), which catalyzes the hydrolysis of NAAG to N-acetyl-aspartate and glutamate. Examples of NAALADase inhibitors include 2-PMPA (2-(phosphonomethyl)pentanedioic acid), which is described in Slusher et al., *Nat. Med.,* 5(12): 1396-402 (1999); and compounds described in *J. Med. Chem.* 39: 619 (1996), US Pub. No. 20040002478, and U.S. Pat. Nos. 6,313,159, 6,479,470, and 6,528,499. In some embodiments, the mGlu modulator is the mGlu$_3$-selective antagonist, beta-NAAG.

Additional non-limiting examples of reported glutamate modulators include memantine (CAS RN 19982-08-2), memantine hydrochloride (CAS RN 41100-52-1), and riluzole (CAS RN 1744-22-5).

In some non-limiting embodiments, a reported Group II modulator is administered in combination with one or more additional compounds reported as active against a Group I and/or a Group III mGlu receptor. For example, in some cases, methods comprise modulating the activity of at least one Group I receptor and at least one Group II mGlu receptor (e.g., with a compound described herein). Examples of compounds useful in modulating the activity of Group I receptors include Group I-selective agonists, such as (i) trans-azetidine-2,4,-dicarboxylic acid (tADA), which is described in Kozikowski et al., *J. Med. Chem.,* 36: 2706 (1993) and Manahan-Vaughan et al., *Neuroscience,* 72: 999 (1996); (ii) (RS)-3,5-Dihydroxyphenylglycine (DHPG), which is described in Ito et al., *NeuroReport* 3: 1013 (1992); or a composition comprising (S)-DHPG substantially free of (R)-DHPG, as described, e.g., in Baker et al., *Bioorg. Med. Chem. Lett.* 5: 223 (1995); (iii) (RS)-3-Hydroxyphenylglycine, which is described in Birse et al., *Neuroscience* 52: 481 (1993); or a composition comprising (S)-3-Hydroxyphenylglycine substantially free of (R)-3-Hydroxyphenylglycine, as described, e.g., in Hayashi et al., *J. Neurosci.,* 14: 3370 (1994); (iv) and (S)-Homoquisqualate, which is described in Porter et al., *Br. J. Pharmacol.,* 106: 509 (1992).

Additional non-limiting examples of reported Group I modulators include (i) Group I agonists, such as (RS)-3,5-dihydroxyphenylglycine, described in Brabet et al., *Neuropharmacolo,* 34, 895-903, 1995; and compounds described in U.S. Pat. Nos. 6,399,641 and 6,589,978, and US Pub No. 20030212066; (ii) Group I antagonists, such as (S)-4-Carboxy-3-hydroxyphenylglycine; 7-(Hydroxyimino)cyclopropa-β-chromen-1α-carboxylate ethyl ester; (RS)-1-Aminoindan-1,5-dicarboxylic acid (AIDA); 2-Methyl-6 (phenylethynyl)pyridine (MPEP); 2-Methyl-6-(2-phenylethenyl)pyridine (SIB-1893); 6-Methyl-2-(phenylazo)-3-pyridinol (SIB-1757); (Sα-Amino-4-carboxy-2-methylbenzeneacetic acid; and compounds described in U.S. Pat. Nos. 6,586,422, 5,783,575, 5,843,988, 5,536,721, 6,429,207, 5,696,148, and 6,218,385, and US Pub Nos. 20030109504, 20030013715, 20050154027, 20050004130, 20050209273, 20050197361, and 20040082592; (iii) mGlu$_5$-selective agonists, such as (RS)-2-Chloro-5-hydroxyphenylglycine (CHPG); and (iv) mGlu$_5$-selective antagonists, such as 2-methyl-6-(phenylethynyl)-pyridine (MPEP); and compounds described in U.S. Pat. No. 6,660,753; and US Pub Nos. 20030195139, 20040229917, 20050153986, 20050085514, 20050065340, 20050026963, 20050020585, and 20040259917.

Non-limiting examples of compounds reported to modulate Group III receptors include (i) the Group 111-selective agonists (L)-2-amino-4-phosphonobutyric acid (L-AP4), described in Knopfel et al., *J. Med. Chem.,* 38, 1417-1426 (1995); and (S)-2-Amino-2-methyl-4-phosphonobutanoic acid; (ii) the Group III-selective antagonists (RS)-α-Cyclopropyl-4-phosphonophenylglycine; (RS)-α-Methylserine-O-phosphate (MSOP); and compounds described in US App. No. 20030109504; and (iii) (1S,3R,4S)-1-aminocyclopentane-1,2,4-tricarboxylic acid (ACPT-I).

In additional embodiments, the neurogenic agent used in combination with a PDE agent may be a reported AMPA modulator. Non-limiting examples include CX-516 or ampalex (CAS RN 154235-83-3), Org-24448 (CAS RN 211735-76-1), LY451395 (2-propanesulfonamide, N-[(2R)-2-[4'-[2-[methylsulfonyl)amino]ethyl][1,1'-biphenyl]-4-yl] propyl]-), LY-450108 (see Jhee et al. "Multiple-dose plasma pharmacokinetic and safety study of LY450108 and LY451395 (AMPA receptor potentiators) and their concentration in cerebrospinal fluid in healthy human subjects." *J*

Clin Pharmacol. 2006 46(4):424-32), and CX717. Additional examples of reported antagonists include irampanel (CAS RN 206260-33-5) and E-2007.

Further non-limiting examples of reported AMPA receptor antagonists for use in combinations include YM90K (CAS RN 154164-30-4), YM872 or Zonampanel (CAS RN 210245-80-0), NBQX (or 2,3-Dioxo-6-nitro-7-sulfamoyl-benzo[f]quinoxaline; CAS RN 118876-58-7), PNQX (1,4,7,8,9,10-hexahydro-9-methyl-6-nitropyrido[3,4-f]quinoxaline-2,3-dione), and ZK200775 ([1,2,3,4-tetrahydro-7-morpholinyl-2,3-dioxo-6-(fluoromethyl) quinoxalin-1-yl] methylphosphonate).

In additional embodiments, a neurogenic agent used in combination with a PDE agent may be a reported muscarinic agent. Non-limiting examples of a reported muscarinic agent include a muscarinic agonist such as milameline (CI-979), or a structurally or functionally related compound disclosed in U.S. Pat. Nos. 4,786,648, 5,362,860, 5,424,301, 5,650,174, 4,710,508, 5,314,901, 5,356,914, or 5,356,912; or xanomeline, or a structurally or functionally related compound disclosed in U.S. Pat. Nos. 5,041,455, 5,043,345, or 5,260,314.

Other non-limiting examples include a muscarinic agent such as alvameline (LU 25-109), or a functionally or structurally compound disclosed in U.S. Pat. Nos. 6,297,262, 4,866,077, RE36,374, 4,925,858, PCT Publication No. WO 97/17074, or in Moltzen et al., *J Med. Chem.* 1994 Nov. 25; 37(24):4085-99; 2,8-dimethyl-3-methylene-1-oxa-8-azaspiro[4,5]decane (YM-796) or YM-954, or a functionally or structurally related compound disclosed in U.S. Pat. Nos. 4,940,795, RE34,653, 4,996,210, 5,041,549, 5,403,931, or 5,412,096, or in Wanibuchi et al., *Eur. J. Pharmacol.*, 187, 479-486 (1990); cevimeline (AF 102B), or a functionally or structurally compound disclosed in U.S. Pat. Nos. 4,855,290, 5,340,821, 5,580,880 (American Home Products), or 4,981,858 (optical isomers of AF102B); sabcomeline (SB 202026), or a functionally or structurally related compound described in U.S. Pat. Nos. 5,278,170, RE35,593, 6,468,560, 5,773,619, 5,808,075, 5,545,740, 5,534,522, or 6,596,869, U.S. Patent Publication Nos. 2002/0127271, 2003/0129246, 2002/0150618, 2001/0018074, 2003/0157169, or 2001/0003588, Bromidge et al., *J Med. Chem.* 19; 40(26):4265-80 (1997), or Harries et al., *British J. Pharm.*, 124, 409-415 (1998); talsaclidine (WAL 2014 FU), or a functionally or structurally compound disclosed in U.S. Pat. Nos. 5,451,587, 5,286,864, 5,508,405, 5,451,587, 5,286,864, 5,508,405, or 5,137,895, or in *Pharmacol. Toxicol.*, 78, 59-68 (1996); or a 1-methyl-1,2,5,6-tetrahydropyridyl-1,2,5-thiadiazole derivative, such as tetra(ethyleneglycol)(4-methoxy-1,2,5-thiadiazol-3-yl)[3-(1-methyl-1,2,5,6-tetrahydropyrid-3-yl)-1,2,5-thiadiazol-4-yl]ether, or a compound that is functionally or structurally related to a 1-methyl-1,2,5,6-tetrahydropyridyl-1, 2,5-thiadiazole derivative as provided by Cao et al. ("Synthesis and biological characterization of 1-methyl-1,2,5,6-tetrahydropyridyl-1,2,5-thiadiazole derivatives as muscarinic agonists for the treatment of neurological disorders." *J. Med. Chem.* 46(20):4273-4286, 2003).

Yet additional non-limiting examples include besipiridine, SR-46559, L-689,660, S-9977-2, AF-102, thiopilocarpine, or an analog of clozapine, such as a pharmaceutically acceptable salt, ester, amide, or prodrug form thereof, or a diaryl[a,d] cycloheptene, such as an amino substituted form thereof, or N-desmethylclozapine, which has been reported to be a metabolite of clozapine, or an analog or related compound disclosed in US 2005/0192268 or WO 05/63254.

In other embodiments, the muscarinic agent is an $m_1$ receptor agonist selected from 55-LH-3B, 55-LH-25A, 55-LH-30B, 55-LH-4-1A, 40-LH-67, 55-LH-15A, 55-LH-16B, 55-LH-16V, 55-LH-11C, 55-LH-31A, 55-LH-46, 55-LH-47, 55-LH-4-3A, or a compound that is functionally or structurally related to one or more of these agonists disclosed in US 2005/0130961 or WO 04/087158.

In additional embodiments, the muscarinic agent is a benzimidazolidinone derivative, or a functionally or structurally compound disclosed in U.S. Pat. No. 6,951,849, US 2003/0100545, WO 04/089942, or WO 03/028650; a spiroazacyclic compound, or a functionally or structurally related compound like 1-oxa-3,8-diaza-spiro[4,5]decan-2-one or a compound disclosed in U.S. Pat. No. 6,911,452 or WO 03/057698; or a tetrahydroquinoline analog, or a functionally or structurally compound disclosed in US 2003/0176418, US 2005/0209226, or WO 03/057672.

In yet additional embodiments, the neurogenic agent in combination with a PDE agent is a reported HDAC inhibitor. The term "HDAC" refers to any one of a family of enzymes that remove acetyl groups from the epsilon-amino groups of lysine residues at the N-terminus of a histone. An HDAC inhibitor refers to compounds capable of inhibiting, reducing, or otherwise modulating the deacetylation of histones mediated by a histone deacetylase. Non-limiting examples of a reported HDAC inhibitor include a short-chain fatty acid, such as butyric acid, phenylbutyrate (PB), 4-phenylbutyrate (4-PBA), pivaloyloxymethyl butyrate (Pivanex, AN-9), isovalerate, valerate, valproate, valproic acid, propionate, butyramide, isobutyramide, phenylacetate, 3-bromopropionate, or tributyrin; a compound bearing a hydroxyamic acid group, such as suberoylanlide hydroxamic acid (SAHA), trichostatin A (TSA), trichostatin C (TSC), salicylhydroxamic acid, oxamflatin, suberic bishydroxamic acid (SBHA), m-carboxy-cinnamic acid bishydroxamic acid (CBHA), pyroxamide (CAS RN 382180-17-8), diethyl bis-(pentamethylene-N, N-dimethylcarboxamide) malonate (EMBA), azelaic bishydroxamic acid (ABHA), azelaic-1-hydroxamate-9-anilide (AAHA), 6-(3-Chlorophenylureido) carpoic hydroxamic acid, or A-161906; a cyclic tetrapeptide, such as Depsipeptide (FK228), FR225497, trapoxin A, apicidin, chlamydocin, or HC-toxin; a benzamide, such as MS-275; depudecin, a sulfonamide anilide (e.g., diallyl sulfide), BL1521, curcumin (diferuloylmethane), CI-994 (N-acetyldinaline), spiruchostatin A, Scriptaid, carbamazepine (CBZ), or a related compound; a compound comprising a cyclic tetrapeptide group and a hydroxamic acid group (examples of such compounds are described in U.S. Pat. Nos. 6,833,384 and 6,552,065); a compound comprising a benzamide group and a hydroxamic acid group (examples of such compounds are described in Ryu et al., Cancer Lett. 2005 Jul. 9 (epub), Plumb et al., Mol Cancer Ther., 2(8):721-8 (2003), Ragno et al., J Med. Chem., 47(6):1351-9 (2004), Mai et al., J Med. Chem., 47(5):1098-109 (2004), Mai et al., J Med. Chem., 46(4):512-24 (2003), Mai et al., J Med. Chem., 45(9): 1778-84 (2002), Massa et al., J Med. Chem., 44(13):2069-72 (2001), Mai et al., J Med. Chem., 48(9):3344-53 (2005), and Mai et al., J Med. Chem., 46(23):4826-9 (2003)); a compound described in U.S. Pat. Nos. 6,897,220, 6,888,027, 5,369,108, 6,541,661, 6,720,445, 6,562,995, 6,777,217, or 6,387,673, or U.S. Patent Publication Nos. 20050171347, 20050165016, 20050159470, 20050143385, 20050137234, 20050137232, 20050119250, 20050113373, 20050107445, 20050107384, 20050096468, 20050085515, 20050032831, 20050014839, 20040266769, 20040254220, 20040229889, 20040198830, 20040142953, 20040106599, 20040092598, 20040077726, 20040077698, 20040053960, 20030187027, 20020177594, 20020161045, 20020119996, 20020115826, 20020103192, or 20020065282; FK228, AN-9, MS-275, CI-994, SAHA, G2M-777, PXD-101, LBH-589, MGCD-0103, MK0683, sodium phenylbutyrate, CRA-024781, and derivatives, salts, metabolites, prodrugs, and stereoisomers thereof; and a molecule that inhibits the transcription and/or translation of one or more HDACs.

Additional non-limiting examples include a reported HDac inhibitor selected from ONO-2506 or arundic acid (CAS RN 185517-21-9); MGCDO103 (see Gelmon et al. "Phase I trials of the oral histone deacetylase (HDAC) inhibitor MGCDO103 given either daily or 3× weekly for 14 days every 3 weeks in patients (pts) with advanced solid tumors." *Journal of Clinical Oncology*, 2005 ASCO Annual Meeting Proceedings. 23(16S, June 1 Supplement), 2005: 3147 and Kalita et al. "Pharmacodynamic effect of MGCD0103, an oral isotype-selective histone deacetylase (HDAC) inhibitor, on HDAC enzyme inhibition and histone acetylation induction in Phase I clinical trials in patients (pts) with advanced solid tumors or non-Hodgkin's lymphoma (NHL)" *Journal of Clinical Oncology*, 2005 ASCO Annual Meeting Proceedings. 23(16S, Part I of II, June 1 Supplement), 2005: 9631), a reported thiophenyl derivative of benzamide HDac inhibitor as presented at the 97th American Association for Cancer Research (AACR) Annual Meeting in Washington, D.C. in a poster titled "Enhanced Isotype-Selectivity and Antiproliferative Activity of Thiophenyl Derivatives of BenzamideHDAC Inhibitors In Human Cancer Cells," (abstract #4725), and a reported HDac inhibitor as described in U.S. Pat. No. 6,541,661; SAHA or Vorinostat (CAS RN 149647-78-9); PXD101 or PXD 101 or PX 105684 (CAS RN 414864-00-9), CI-994 or Tacedinaline (CAS RN 112522-64-2), MS-275 (CAS RN 209783-80-2), or an inhibitor reported in WO2005/108367.

In other embodiments, the neurogenic agent in combination with a PDE agent is a reported GABA modulator which modulates GABA receptor activity at the receptor level (e.g., by binding directly to GABA receptors), at the transcriptional and/or translational level (e.g., by preventing GABA receptor gene expression), and/or by other modes (e.g., by binding to a ligand or effector of a GABA receptor, or by modulating the activity of an agent that directly or indirectly modulates GABA receptor activity). Non-limiting examples of GABA-A receptor modulators useful in methods described herein include triazolophthalazine derivatives, such as those disclosed in WO 99/25353, and WO/98/04560; tricyclic pyrazolo-pyridazinone analogues, such as those disclosed in WO 99/00391; fenamates, such as those disclosed in U.S. Pat. No. 5,637,617; triazolo-pyridazine derivatives, such as those disclosed in WO 99/37649, WO 99/37648, and WO 99/37644; pyrazolo-pyridine derivatives, such as those disclosed in WO 99/48892; nicotinic derivatives, such as those disclosed in WO 99/43661 and U.S. Pat. No. 5,723,462; muscimol, thiomuscimol, and compounds disclosed in U.S. Pat. No. 3,242,190; baclofen and compounds disclosed in U.S. Pat. No. 3,471,548; phaclofen; quisqualamine; ZAPA; zaleplon; THIP; imidazole-4-acetic acid (IMA); (+)-bicuculline; gabalinoleamide; isoguvicaine; 3-aminopropane sulphonic acid; piperidine-4-sulphonic acid; 4,5,6,7-tetrahydro-[5,4-c]-pyridin-3-ol; SR 95531; RU5315; CGP 55845; CGP 35348; FG 8094; SCH 50911; NG2-73; NGD-96-3; pricrotoxin and other bicyclophosphates disclosed in Bowery et al., Br. J. Pharmacol., 57; 435 (1976).

Additional non-limiting examples of GABA-A modulators include compounds described in U.S. Pat. Nos. 6,503,925; 6,218,547; 6,399,604; 6,646,124; 6,515,140; 6,451,809; 6,448,259; 6,448,246; 6,423,711; 6,414,147; 6,399,604; 6,380,209; 6,353,109; 6,297,256; 6,297,252; 6,268,496; 6,211,365; 6,166,203; 6,177,569; 6,194,427; 6,156,898; 6,143,760; 6,127,395; 6,103,903; 6,103,731; 6,723,735; 6,479,506; 6,476,030; 6,337,331; 6,730,676; 6,730,681; 6,828,322; 6,872,720; 6,699,859; 6,696,444; 6,617,326; 6,608,062; 6,579,875; 6,541,484; 6,500,828; 6,355,798; 6,333,336; 6,319,924; 6,303,605; 6,303,597; 6,291,460; 6,255,305; 6,133,255; 6,872,731; 6,900,215; 6,642,229; 6,593,325; 6,914,060; 6,914,063; 6,914,065; 6,936,608; 6,534,505; 6,426,343; 6,313,125; 6,310,203; 6,200,975; 6,071,909; 5,922,724; 6,096,887; 6,080,873; 6,013,799; 5,936,095; 5,925,770; 5,910,590; 5,908,932; 5,849,927; 5,840,888; 5,817,813; 5,804,686; 5,792,766; 5,750,702; 5,744,603; 5,744,602; 5,723,462; 5,696,260; 5,693,801; 5,677,309; 5,668,283; 5,637,725; 5,637,724; 5,625,063; 5,610,299; 5,608,079; 5,606,059; 5,604,235; 5,585,490; 5,510,480; 5,484,944; 5,473,073; 5,463,054; 5,451,585; 5,426,186; 5,367,077; 5,328,912 5,326,868; 5,312,822; 5,306,819; 5,286,860; 5,266,698; 5,243,049; 5,216,159; 5,212,310; 5,185,446; 5,185,446; 5,182,290; 5,130,430; 5,095,015; 20050014939; 20040171633; 20050165048; 20050165023; 20040259818; and 20040192692.

In some embodiments, the GABA-A modulator is a subunit-selective modulator. Non-limiting examples of GABA-A modulator having specificity for the alpha1 subunit include alpidem and zolpidem. Non-limiting examples of GABA-A modulator having specificity for the alpha2 and/or alpha3 subunits include compounds described in U.S. Pat. Nos. 6,730,681; 6,828,322; 6,872,720; 6,699,859; 6,696,444; 6,617,326; 6,608,062; 6,579,875; 6,541,484; 6,500,828; 6,355,798; 6,333,336; 6,319,924; 6,303,605; 6,303,597; 6,291,460; 6,255,305; 6,133,255; 6,900,215; 6,642,229; 6,593,325; and 6,914,063. Non-limiting examples of GABA-A modulator having specificity for the alpha2, alpha3 and/or alpha5 subunits include compounds described in U.S. Pat. Nos. 6,730,676 and 6,936,608. Non-limiting examples of GABA-A modulators having specificity for the alpha5 subunit include compounds described in U.S. Pat. Nos. 6,534,505; 6,426,343; 6,313,125; 6,310,203; 6,200,975 and 6,399,604. Additional non-limiting subunit selective GABA-A modulators include CL218,872 and related compounds disclosed in Squires et al., *Pharmacol. Biochem. Behav.*, 10: 825 (1979); and beta-carboline-3-carboxylic acid esters described in Nielsen et al., *Nature*, 286: 606 (1980).

In some embodiments, the GABA-A receptor modulator is a reported allosteric modulator. In various embodiments, allosteric modulators modulate one or more aspects of the activity of GABA at the target GABA receptor, such as potency, maximal effect, affinity, and/or responsiveness to other GABA modulators. In some embodiments, allosteric modulators potentiate the effect of GABA (e.g., positive allosteric modulators), and/or reduce the effect of GABA (e.g., inverse agonists). Non-limiting examples of benzodiazepine GABA-A modulators include aiprazolam, bentazepam, bretazenil, bromazepam, brotizolam, cannazepam, chlordiazepoxide, clobazam, clonazepam, cinolazepam, clotiazepam, cloxazolam, clozapin, delorazepam, diazepam, dibenzepin, dipotassium chlorazepat, divaplon, estazolam, ethylloflazepat, etizolam, fludiazepam, flumazenil, flunitrazepam, flurazepaml 1HCl, flutoprazepam, halazeparn, haloxazolam, imidazenil, ketazolam, lorazepam, loprazolam, lonmetazepam, medazepam, metaclazepam, mexozolam, midazolam-HCl, nabanezil, nimetazepam, nitrazepam, nordazepam, oxazepam-tazepam, oxazolam, pinazepam, prazepam, quazepam, sarmazenil, suriclone, temazepam, tetrazepam, tofisopam, triazolam, zaleplon, zolezepam, zolpidem, zopiclone, and zopielon.

Additional non-limiting examples of benzodiazepine GABA-A modulators include Ro15-4513, CL218872, CGS 8216, CGS 9895, PK 9084, U-93631, beta-CCM, beta-CCB, beta-CCP, Ro 19-8022, CGS 20625, NNC 14-0590, Ru 33-203, 5-amino-1-bromouracil, GYKI-52322, FG 8205, Ro 19-4603, ZG-63, RWJ46771, SX-3228, and L-655,078; NNC 14-0578, NNC 14-8198, and additional compounds described in Wong et al., *Eur J Pharmacol* 209: 319-325 (1995); Y-23684 and additional compounds in Yasumatsu et al., *Br J Pharmacol* 111: 1170-1178 (1994); and compounds described in U.S. Pat. No. 4,513,135.

Non-limiting examples of barbiturate or barbituric acid derivative GABA-A modulators include phenobarbital, pentobarbital, pentobarbitone, primidone, barbexaclon, dipropyl barbituric acid, eunarcon, hexobarbital, mephobarbital, methohexital, Na-methohexital, 2,4,6(1H,3H,5)-pyrimidintrion, secbutabarbital and/or thiopental.

Non-limiting examples of neurosteroid GABA-A modulators include alphaxalone, allotetrahydrodeoxycorticosterone, tetrahydrodeoxycorticosterone, estrogen, progesterone 3-beta-hydroxyandrost-5-en-17-on-3-sulfate, dehydroepianrosterone, eltanolone, ethinylestradiol, 5-pregnen-3-beta-ol-20 on-sulfate, 5a-pregnan-3α-ol-20-one (5PG), allopregnanolone, pregnanolone, and steroid derivatives and metabolites described in U.S. Pat. Nos. 5,939,545, 5,925,630, 6,277,838, 6,143,736, RE35,517, 5,925,630, 5,591,733, 5,232,917, 20050176976, WO 96116076, WO 98/05337, WO 95/21617, WO 94/27608, WO 93/18053, WO 93/05786, WO 93/03732, WO 91116897, EP01038880, and Han et al., *J. Med. Chem.*, 36, 3956-3967 (1993), Anderson et al., *J. Med. Chem.*, 40, 1668-1681 (1997), Hogenkamp et al., *J. Med. Chem.*, 40, 61-72 (1997), Upasani et al., *J. Med. Chem.*, 40, 73-84 (1997), Majewska et al., *Science* 232:1004-1007 (1986), Harrison et al., *J. Pharmacol. Exp. Ther.* 241:346-353 (1987), Gee et al., *Eur. J. Pharmacol.*, 136:419-423 (1987) and Birtran et al., *Brain Res.*, 561, 157-161 (1991).

Non-limiting examples of beta-carboline GABA-A modulators include abecamil, 3,4-dihydro-beta-carboline, gedocamil, 1-methyl-1-vinyl-2,3,4-trihydro-beta-carboline-3-carboxylic acid, 6-methoxy-1,2,3,4-tetrahydro-beta-carboline, N-BOC-L-1,2,3,4-tetrahydro-b-eta-carboline-3-carboxylic acid, tryptoline, pinoline, methoxyharmalan, tetrahydro-beta-carboline (THBC), 1-methyl-THBC, 6-methoxy-THBC, 6-hydroxy-THBC, 6-methoxyharmalan, norharman, 3,4-dihydro-beta-carboline, and compounds described in Nielsen et al., *Nature*, 286: 606 (1980).

In some embodiments, the GABA modulator modulates GABA-B receptor activity. Non-limiting examples of reported GABA-B receptor modulators useful in methods described herein include CGP36742; CGP-64213; CGP 56999A; CGP 54433A; CGP 36742; SCH 50911; CGP 7930; CGP 13501; baclofen and compounds disclosed in U.S. Pat. No. 3,471,548; saclofen; phaclofen; 2-hydroxysaclofen; SKF 97541; CGP 35348 and related compounds described in Olpe, et al., *Eur. J. Pharmacol.*, 187, 27 (1990); phosphinic acid derivatives described in Hills, et al., *Br. J. Pharmacol.*, 102, pp. 5-6 (1991); and compounds described in 4,656,298, 5,929,236, EP0463969, EP 0356128, Kaupmann et al., *Nature* 368: 239 (1997), Karla et al., *J Med. Chem.*, 42(11): 2053-9 (1992), Ansar et al., *Therapie*, 54(5):651-8 (1999), and Castelli et al., *Eur J. Pharmacol.*, 446(1-3): 1-5 (2002).

In some embodiments, the GABA modulator modulates GABA-C receptor activity. Non-limiting examples of reported GABA-C receptor modulators useful in methods described herein include cis-aminocrotonic acid (CACA); 1,2,5,6-tetrahydropyridine-4-yl methyl phosphinic acid (TP-MPA) and related compounds such as P4MPA, PPA and SEPI; 2-methyl-TACA; (+/−)-TAMP; muscimol and compounds disclosed in U.S. Pat. No. 3,242,190; ZAPA; THIP and related analogues, such as aza-THIP; pricotroxin; imidazole-4-acetic acid (IMA); and CGP36742.

In some embodiments, the GABA modulator modulates the activity of glutamic acid decarboxylase (GAD).

In some embodiments, the GABA modulator modulates GABA transaminase (GTA). Non-limiting examples of GTA modulators include the GABA analogue vigabatrin and compounds disclosed in U.S. Pat. No. 3,960,927.

In some embodiments, the GABA modulator modulates the reuptake and/or transport of GABA from extracellular regions. In other embodiments, the GABA modulator modulates the activity of the GABA transporters, GAT-1, GAT-2, GAT-3 and/or BGT-1. Non-limiting examples of GABA reuptake and/or transport modulators include nipecotic acid and related derivatives, such as CI-966; SKF 89976A; TACA; stiripentol; tiagabine and GAT-1 inhibitors disclosed in U.S. Pat. No. 5,010,090; (R)-1-(4,4-diphenyl-3-butenyl)-3-piperidinecarboxylic acid and related compounds disclosed in U.S. Pat. No. 4,383,999; (R)-1-[4,4-bis(3-methyl-2-thienyl)-3-butenyl]-3-piperidinecarboxylic acid and related compounds disclosed in Anderson et al., *J. Med. Chem.* 36, (1993) 1716-1725; guvacine and related compounds disclosed in Krogsgaard-Larsen, *Molecular & Cellular Biochemistry* 31, 105-121 (1980); GAT-4 inhibitors disclosed in U.S. Pat. No. 6,071,932; and compounds disclosed in U.S. Pat. No. 6,906, 177 and Ali, F. E., et al. *J. Med. Chem.* 1985, 28, 653-660. Methods for detecting GABA reuptake inhibitors are known in the art, and are described, e.g., in U.S. Pat. Nos. 6,906,177; 6,225,115; 4,383,999; Ali, F. E., et al. *J. Med. Chem.* 1985, 28, 653-660.

In some embodiments, the GABA modulator is the benzodiazepine Clonazepam, which is described, e.g., in U.S. Pat. Nos. 3,121,076 and 3,116,203; the benzodiazepine Diazepam, which is described, e.g., in U.S. Pat. Nos. 3,371,085; 3,109,843; and 3,136,815; the short-acting diazepam derivative Midazolam, which is a described, e.g., in U.S. Pat. No. 4,280,957; the imidazodiazepine Flumazenil, which is described, e.g., in U.S. Pat. No. 4,316,839; the benzodiazepine Lorazepam is described, e.g., in U.S. Pat. No. 3,296, 249; the benzodiazepine L-655708, which is described, e.g., in Quirk et al. *Neuropharmacology* 1996, 35, 1331; Sur et al. *Mol. Pharmacol.* 1998, 54, 928; and Sur et al. *Brain Res.* 1999, 822, 265; the benzodiazepine Gabitril; Zopiclone, which binds the benzodiazepine site on GABA-A receptors, and is disclosed, e.g., in U.S. Pat. No. 3,862,149 and U.S. Pat. No. 4,220,646; the GABA-A potentiator Indiplon as described, e.g., in Foster et al., *J Pharmacol Exp Ther.*, 311 (2):547-59 (2004), U.S. Pat. Nos. 4,521,422 and 4,900,836; Zolpidem, described, e.g., in U.S. Pat. No. 4,794,185 and EP50563; Zaleplon, described, e.g., in U.S. Pat. No. 4,626, 538; Abecarnil, described, e.g., in Stephens et al., *J Pharmacol Exp Ther.*, 253(1):334-43 (1990); the GABA-A agonist Isoguvacine, which is described, e.g., in Chebib et al., *Clin. Exp. Pharmacol. Physiol.* 1999, 26, 937-940; Leinekugel et al. *J. Physiol.* 1995, 487, 319-29; and White et al., *J. Neurochem.* 1983, 40(6), 1701-8; the GABA-A agonist Gaboxadol (THIP), which is described, e.g., in U.S. Pat. No. 4,278,676 and Krogsgaard-Larsen, *Acta. Chem. Scand.* 1977, 31, 584; the GABA-A agonist Muscimol, which is described, e.g., in U.S. Pat. Nos. 3,242,190 and 3,397,209; the inverse GABA-A agonist beta-CCP, which is described, e.g., in Nielsen et al., *J. Neurochem.*, 36(1):276-85 (1981); the GABA-A potentiator Riluzole, which is described, e.g., in U.S. Pat. No. 4,370,338 and EP 50,551; the GABA-B agonist and GABA-C antagonist SKF 97541, which is described, e.g., in Froestl et al., *J. Med. Chem.* 38 3297 (1995); Hoskison et al., *Neurosci. Lett.* 2004, 365(1), 48-53 and Hue et al., *J. Insect Physiol.* 1997, 43(12), 1125-1131; the GABA-B agonist Baclofen, which is described, e.g., in U.S. Pat. No. 3,471,548; the GABA-C agonist cis-4-aminocrotonic acid (CACA), which is described, e.g., in Ulloor et al. *J. Neurophysiol.* 2004, 91(4), 1822-31; the GABA-A antagonist Phaclofen, which is described, e.g., in Kerr et al. *Brain Res.* 1987, 405, 150; Karlsson et al. *Eur. J. Pharmacol.* 1988, 148, 485; and Hasuo, Gallagher *Neurosci. Lett.* 1988, 86, 77; the GABA-A antagonist SR 95531, which is described, e.g., in Stell et al. *J. Neurosci.* 2002, 22(10), RC223; Wermuth et al., *J. Med. Chem.* 30 239 (1987); and Luddens and Korpi, *J. Neurosci.* 15: 6957 (1995); the GABA-A antagonist Bicuculline, which is a described, e.g., in Groenewoud, *J. Chem. Soc.* 1936, 199; Olsen et al., *Brain Res.* 102: 283 (1976) and Haworth et al. *Nature* 1950, 165, 529; the selective GABA-B antagonist CGP 35348, which is described, e.g., in Olpe et al. *Eur. J. Pharmacol.* 1990, 187, 27; Hao et al. *Neurosci. Lett.* 1994, 182, 299; and Froestl et al. *Pharmacol. Rev. Comm.* 1996, 8, 127; the selective GABA-B antagonist CGP 46381, which is described, e.g., in Lingenhoehl, *Pharmacol. Comm.* 1993, 3, 49; the selective GABA-B antagonist CGP 52432, which is described, e.g., in Lanza et al. *Eur. J. Pharmacol.* 1993, 237, 191; Froestl et al. *Pharmacol. Rev. Comm.* 1996, 8, 127; Bonanno et al. *Eur. J. Pharmacol.* 1998, 362, 143; and Libri et al. *Naunyn-Schmied. Arch. Pharmacol.* 1998, 358, 168; the selective GABA-B antagonist CGP 54626, which is described, e.g., in Brugger et al. *Eur. J. Pharmacol.* 1993, 235, 153; Froestl et al. *Pharmacol. Rev. Comm.* 1996, 8, 127; and Kaupmann et al. *Nature* 1998, 396, 683; the selective GABA-B antagonist CGP 55845, which is a GABA-receptor antagonist described, e.g., in Davies et al. *Neuropharmacology* 1993, 32, 1071; Froestl et al. *Pharmacol. Rev. Comm.* 1996, 8, 127; and Deisz *Neuroscience* 1999, 93, 1241; the selective GABA-B antagonist Saclofen, which is described, e.g., in Bowery, *TiPS,* 1989, 10, 401; and Kerr et al. *Neurosci Lett.* 1988; 92(1):92-6; the GABA-B antagonist 2-Hydroxysaclofen, which is described, e.g., in Kerr et al. *Neurosci. Lett.* 1988, 92, 92; and Curtis et al. *Neurosci. Lett.* 1988, 92, 97; the GABA-B antagonist SCH 50,911, which is described, e.g., in Carruthers et al., *Bioorg Med Chem Lett* 8: 3059-3064 (1998); Bolser et al. *J. Pharmacol. Exp. Ther.* 1996, 274, 1393; Hosford et al. *J. Pharmacol. Exp. Ther.* 1996, 274, 1399; and Ong et al. *Eur. J. Pharmacol.* 1998, 362, 35; the selective GABA-C antagonist TPMPA, which is described, e.g., in Schlicker et al., *Brain Res. Bull.* 2004, 63(2), 91-7; Murata et al., *Bioorg. Med. Chem. Lett.* 6: 2073 (1996); and Ragozzino et al., *Mol.Pharmacol.* 50: 1024 (1996); a GABA derivative, such as Pregabalin [(S)-(+)-3-isobutylgaba] or gabapentin [1-(aminomethyl)cyclohexane acetic acid]. Gabapentin is described, e.g., in U.S. Pat. No. 4,024,175; the lipid-soluble GABA agonist Progabide, which is metabolized in vivo into GABA and/or pharmaceutically active GABA derivatives in vivo. Progabide is described, e.g., in U.S. Pat. Nos. 4,094,992 and 4,361,583; the GAT1 inhibitor Tiagabine, which is described, e.g., in U.S. Pat. No. 5,010,090 and Andersen et al. *J. Med. Chem.* 1993, 36, 1716; the GABA transaminase inhibitor Valproic Acid (2-propylpentanoic acid or dispropylacetic acid), which is described, e.g., in U.S. Pat. No. 4,699,927 and Carraz et al., *Therapie,* 1965, 20, 419; the GABA transaminase inhibitor Vigabatrin, which is described, e.g., in U.S. Pat. No. 3,960,927; or Topiramate, which is described, e.g., in U.S. Pat. No. 4,513,006.

Additionally, the neurogenic agent in combination with a PDE agent may be a neurogenic sensitizing agent that is a reported anti-epileptic agent. Non-limiting examples of such agents include carbamazepine or tegretol (CAS RN 298-46-4), clonazepam (CAS RN 1622-61-3), BPA or 3-(p-Boronophenyl)alanine (CAS RN 90580-64-6), gabapentin or neurontin (CAS RN 60142-96-3), phenyloin (CAS RN 57-41-0), topiramate, lamotrigine or lamictal (CAS RN 84057-84-1), phenobarbital (CAS RN 50-06-6), oxcarbazepine (CAS RN 28721-07-5), primidone (CAS RN 125-33-7), ethosuximide (CAS RN 77-67-8), levetiracetam (CAS RN 102767-28-2), zonisamide, tiagabine (CAS RN 115103-54-3), depakote or divalproex sodium (CAS RN 76584-70-8), Felbamate (Na-channel and NMDA receptor antagonist), or pregabalin (CAS RN 148553-50-8).

In further embodiments, the neurogenic sensitizing agent may be a reported direct or indirect modulator of dopamine receptors. Non-limiting examples of such agents include the indirect dopamine agonists methylphenidate (CAS RN 113-45-1) or Methylphenidate hydrochloride (also known as ritalin CAS RN 298-59-9), amphetamine (CAS RN 300-62-9) and methamphetamine (CAS RN 537-46-2), and the direct dopamine agonists sumanirole (CAS RN 179386-43-7), roprinirole (CAS RN 91374-21-9), and rotigotine (CAS RN 99755-59-6). Additional non-limiting examples include 7-OH-DPAT, quinpirole, haloperidole, or clozapine.

Additional non-limiting examples include bromocriptine (CAS RN 25614-03-3), adrogolide (CAS RN 171752-56-0), pramipexole (CAS RN 104632-26-0), Ropinirole (CAS RN 91374-21-9), apomorphine (CAS RN 58-00-4) or apomorphine hydrochloride (CAS RN 314-19-2), lisuride (CAS RN 18016-80-3), Sibenadet hydrochloride or Viozan (CAS RN 154189-24-9), L-DOPA or Levodopa (CAS RN 59-92-7), Melevodopa (CAS RN 7101-51-1), etilevodopa (CAS RN 37178-37-3), Talipexole hydrochloride (CAS RN 36085-73-1) or Talipexole (CAS RN 101626-70-4), Nolomirole (CAS RN 90060-42-7), quinelorane (CAS RN 97466-90-5), pergolide (CAS RN 66104-22-1), fenoldopam (CAS RN 67227-56-9), Carmoxirole (CAS RN 98323-83-2), terguride (CAS RN 37686-84-3), cabergoline (CAS RN 81409-90-7), quinagolide (CAS RN 87056-78-8) or quinagolide hydrochloride (CAS RN 94424-50-7), sumanirole, docarpamine (CAS RN 74639-40-0), SLV-308 or 2(3H)-Benzoxazolone, 7-(4-methyl-1-piperazinyl)-monohydrochloride (CAS RN 269718-83-4), aripiprazole (CAS RN 129722-12-9), bifeprunox, lisdexamfetamine dimesylate (CAS RN 608137-33-3), safinamide (CAS RN 133865-89-1), or Adderall or Amfetamine (CAS RN 300-62-9).

In further embodiments, the neurogenic agent used in combination with a PDE agent may be a reported dual sodium and calcium channel modulator. Non-limiting examples of such agents include safinamide and zonisamide. Additional non-limiting examples include enecadin (CAS RN 259525-01-4), Levosemotiadil (CAS RN 116476-16-5), bisaramil (CAS RN 89194-77-4), SL-34.0829 (see U.S. Pat. No. 6,897,305), lifarizine (CAS RN 119514-66-8), JTV-519 (4-[3-(4-benzylpiperidin-1-yl)propionyl]-7-methoxy-2,3,4,5-tetrahydro-1,4-benzothiazepine monohydrochloride), and delapril.

In further embodiments, the neurogenic agent in used in combination with a PDE agent may be a reported calcium channel antagonist such as amlodipine (CAS RN 88150-42-9) or amlodipine maleate (CAS RN 88150-47-4), nifedipine (CAS RN 21829-25-4), MEM-1003 (CAS RN see Rose et al. "Efficacy of MEM 1003, a novel calcium channel blocker, in delay and trace eyeblink conditioning in older rabbits." *Neurobiol Aging.* 2006 Apr. 16; [Epub ahead of print]), isradipine (CAS RN 75695-93-1), felodipine (CAS RN 72509-76-3; 3,5-Pyridinedicarboxylic acid, 1,4-dihydro-4-(2,3-dichlorophenyl)-2,6-dimethyl-, ethyl methyl ester) or felodipine (CAS RN 86189-69-7; 3,5-Pyridinedicarboxylic acid, 4-(2,3-dichlorophenyl)-1,4-dihydro-2,6-dimethyl-, ethyl methyl ester, (+−)-), lemildipine (CAS RN 125729-29-5 or 94739-

29-4), clevidipine (CAS RN 166432-28-6 or 167221-71-8), verapamil (CAS RN 52-53-9), ziconotide (CAS RN 107452-89-1), monatepil maleate (CAS RN 132046-06-1), manidipine (CAS RN 89226-50-6), Furnidipine (CAS RN 138661-03-7), Nitrendipine (CAS RN 39562-70-4), Loperamide (CAS RN 53179-11-6), Amiodarone (CAS RN 1951-25-3), Bepridil (CAS RN 64706-54-3), diltiazem (CAS RN 42399-41-7), Nimodipine (CAS RN 66085-59-4), Lamotrigine, Cinnarizine (CAS RN 298-57-7), lacipidine (CAS RN 103890-78-4), nilvadipine (CAS RN 75530-68-6), dotarizine (CAS RN 84625-59-2), cilnidipine (CAS RN 132203-70-4), Oxodipine (CAS RN 90729-41-2), aranidipine (CAS RN 86780-90-7), anipamil (CAS RN 83200-10-6), ipenoxazone (CAS RN 104454-71-9), Efonidipine hydrochloride or NZ 105 (CAS RN 111011-53-1) or Efonidipine (CAS RN 111011-63-3), temiverine (CAS RN 173324-94-2), pranidipine (CAS RN 99522-79-9), dopropidil (CAS RN 79700-61-1), lercanidipine (CAS RN 100427-26-7), terodiline (CAS RN 15793-40-5), fantofarone (CAS RN 114432-13-2), azelnidipine (CAS RN 123524-52-7), mibefradil (CAS RN 116644-53-2) or mibefradil dihydrochloride (CAS RN 116666-63-8), SB-237376 (see Xu et al. "Electrophysiologic effects of SB-237376: a new antiarrhythmic compound with dual potassium and calcium channel blocking action." J Cardiovasc Pharmacol. 2003 41(3):414-21), BRL-32872 (CAS RN 113241-47-7), S-2150 (see Ishibashi et al. "Pharmacodynamics of S-2150, a simultaneous calcium-blocking and alpha1-inhibiting antihypertensive drug, in rats." J Pharm Pharmacol. 2000 52(3):273-80), nisoldipine (CAS RN 63675-72-9), semotiadil (CAS RN 116476-13-2), palonidipine (CAS RN 96515-73-0) orpalonidipine hydrochloride (CAS RN 96515-74-1), SL-87.0495 (see U.S. Pat. No. 6,897,305), YM430 (4-((S)-2-hydroxy-3-phenoxypropyl)amino)butyl methyl 2,6-dimethyl-((S)-4-(m-nitrophenyl))-1,4-dihydropyridine-3,5-dicarboxylate), barnidipine (CAS RN 104713-75-9), and AM336 or CVID (see Adams et al. "Omega-Conotoxin CVID Inhibits a Pharmacologically Distinct Voltage-sensitive Calcium Channel Associated with Transmitter Release from Preganglionic Nerve Terminals" J. Biol. Chem., 278(6): 4057-4062, 2003). An additional non-limiting example is NMED-160.

In other embodiments, the neurogenic agent used in combination with a PDE agent may be a reported modulator of a melatonin receptor. Non-limiting examples of such modulators include the melatonin receptor agonists melatonin, LY-156735 (CAS RN 118702-11-7), agomelatine (CAS RN 138112-76-2), 6-chloromelatonin (CAS RN 63762-74-3), Ramelteon (CAS RN 196597-26-9), 2-Methyl-6,7-dichloromelatonin (CAS RN 104513-29-3), and ML 23 (CAS RN 108929-03-9).

In yet further embodiments, the neurogenic agent in combination with a PDE agent may be a reported modulator of a melanocortin receptor. Non-limiting examples of such agents include a melanocortin receptor agonists selected from melanotan II (CAS RN 121062-08-6), PT-141 or Bremelanotide (CAS RN 189691-06-3), HP-228 (see Getting et al. "The melanocortin peptide HP228 displays protective effects in acute models of inflammation and organ damage." Eur J. Pharmacol. 2006 Jan. 24), or AP214 from Action Pharma A/S.

Additional embodiments include a combination of a PDE agent and a reported modulator of angiotensin II function, such as at an angiotensin II receptor. In some embodiments, the neurogenic sensitizing agent used with a PDE agent may be a reported inhibitor of an angiotensin converting enzyme (ACE). Non-limiting examples of such reported inhibitors include a sulfhydryl-containing (or mercapto-containing) agent, such as Alacepril, captopril (Capoten®), fentiapril, pivopril, pivalopril, or zofenopril; a dicarboxylate-containing agent, such as enalapril (Vasotec® or Renitec®) or enalaprilat, ramipril (Altace® or Tritace® or Ramace®), quinapril (Accupril®) or quinapril hydrochloride, perindopril (Coversyl®) or perindopril erbumine (Aceon®g), lisinopril (Lisodur® or Prinivil® or Zestril®); a phosphonate-containing (or phosphate-containing) agent, such as fosinopril (Monopril®), fosinoprilat, fosinopril sodium (CAS RN 88889-14-9), benazepril (Lotensin®) or benazepril hydrochloride, imidapril or imidapril hydrochloride, moexipril (Univasc®), or trandolapril (Mavik®). In other embodiments, a modulator is administered in the form of an ester that increases biovavailability upon oral administration with subsequent conversion into metabolites with greater activity.

Further embodiments include reported angiotensin II modulating entities that are naturally occurring, such as casokinins and lactokinins (breakdown products of casein and whey) which may be administered as such to obviate the need for their formation during digestion. Additional non-limiting embodiments of reported angiotensin receptor antagonists include candesartan (Atacand® or Ratacand®, 139481-59-7) or candesartan cilexetil; eprosartan (Teveten®) or eprosartan mesylate; irbesartan (Aprovel® or Karvea® or Avapro®); losartan (Cozaar® or Hyzaar®); olmesartan (Benicar®, CAS RN 144689-24-7) or olmesartan medoxomil (CAS RN 144689-63-4); telmisartan (Micardis® or Pritor®); or valsartan (Diovan®).

Additional non-limiting examples of a reported angiotensin modulator that may be used in a combination include nateglinide or starlix (CAS RN 105816-04-4); tasosartan or its metabolite enoltasosartan; omapatrilat (CAS RN 167305-00-2); or a combination of nateglinide and valsartan, amoldipine and benazepril (Lotrel 10-40 or Lotrel 5-40), or delapril and manidipine (CHF 1521).

Additionally, the agent used with a PDE agent may be a reported 5HT1a receptor agonist (or partial agonist) such as buspirone (buspar). In some embodiments, a reported 5HT1a receptor agonist is an azapirone, such as, but not limited to, tandospirone, gepirone and ipsapirone. Non-limiting examples of additional reported 5HT1a receptor agonists include flesinoxan(CAS RN 98206-10-1), MDL 72832 hydrochloride, U-92016A, (+)-UH 301, F 13714, F 13640, 6-hydroxy-buspirone (see US 2005/0137206), S-6-hydroxy-buspirone (see US 2003/0022899), R-6-hydroxy-buspirone (see US 2003/0009851), adatanserin, buspirone-saccharide (see WO 00/12067) or 8-hydroxy-2-dipropylaminotetralin (8-OHDPAT).

Additional non-limiting examples of reported 5HT1a receptor agonists include OPC-14523 (1-[3-[4-(3-chlorophenyl)-1-piperazinyl]propyl]-5-methoxy-3,4-dihydro-2[1H]-quinolinone monomethanesulfonate); BMS-181100 or BMY 14802 (CAS RN 105565-56-8); flibanserin (CAS RN 167933-07-5); repinotan (CAS RN 144980-29-0); lesopitron (CAS RN 132449-46-8); piclozotan (CAS RN 182415-09-4); Aripiprazole, Org-13011 (1-(4-trifluoromethyl-2-pyridinyl)-4-[4-[2-oxo-1-pyrrolidinyl]butyl]piperazine (E)-2-butene-dioate); SDZ-MAR-327 (see Christian et al. "Positron emission tomographic analysis of central dopamine D1 receptor binding in normal subjects treated with the atypical neuroleptic, SDZ MAR 327." Int J Mol. Med. 19981(1):243-7); MKC-242 ((S)-5-[3-[(1,4-benzodioxan-2-ylmethyl)amino]propoxy]-1,3-benzodioxole HCl); vilazodone; sarizotan (CAS RN 177975-08-5); roxindole (CAS RN 112192-04-8) or roxindole methanesulfonate (CAS RN 119742-13-1); alnespirone (CAS RN 138298-79-0); bromerguride (CAS RN 83455-48-5); xaliproden (CAS RN 135354-02-8); mazapertine succinate (CAS RN 134208-18-7) or mazapertine (CAS RN 134208-17-6); PRX-00023; F-13640 ((3-chloro-4-fluoro-phenyl)-[4-fluoro-4-[[(5-methyl-pyridin-2-ylmethyl)-amino]methyl]piperidin-1-yl]methanone, fumaric acid salt); eptapirone (CAS RN 179756-85-5); Ziprasidone (CAS RN 146939-27-7); Sunepitron (see Becker et al. "G protein-coupled receptors: In silico drug discovery in 3D" PNAS 2004 101(31):11304-11309); umespirone (CAS RN 107736-98-1); SLV-308; bifeprunox; and zalospirone (CAS RN 114298-18-9).

Yet further non-limiting examples include AP-521 (partial agonist from AsahiKasei) and Du-123015 (from Solvay).

Alternatively, the agent used with a PDE agent may be a reported 5HT4 receptor agonist (or partial agonist). In some embodiments, a reported 5HT4 receptor agonist or partial agonist is a substituted benzamide, such as cisapride; individual, or a combination of, cisapride enantiomers ((+) cisapride and (−) cisapride); mosapride; and renzapride as non-limiting examples. In other embodiments, the chemical entity is a benzofuran derivative, such as prucalopride. Additional embodiments include indoles, such as tegaserod, or benzimidazolones. Other non-limiting chemical entities reported as a 5HT4 receptor agonist or partial agonist include zacopride (CAS RN 90182-92-6), SC-53116 (CAS RN 141196-99-8) and its racemate SC-49518 (CAS RN 146388-57-0), BIMU1 (CAS RN 127595-43-1), TS-951 (CAS RN 174486-39-6), or ML10302 CAS RN 148868-55-7). Additional non-limiting chemical entities include metoclopramide, 5-methoxytryptamine, RS 67506, 2-[1-(4-piperonyl) piperazinyl]benzothiazole, RS66331, BIMU8, SB 205149 (the n-butyl quaternary analog of renzapride), or an indole carbazimidamide as described by Buchheit et al. ("The serotonin 5-HT4 receptor. 2. Structure-activity studies of the indole carbazimidamide class of agonists." J Med. Chem. (1995) 38(13):2331-8). Yet additional non-limiting examples include norcisapride (CAS RN 102671-04-5) which is the metabolite of cisapride; mosapride citrate; the maleate form of tegaserod (CAS RN 189188-57-6); zacopride hydrochloride (CAS RN 99617-34-2); mezacopride (CAS RN 89613-77-4); SK-951 ((+−)-4-amino-N-(2-(1-azabicyclo(3.3.0)octan-5-yl)ethyl)-5-chloro-2,3-dihydro-2-methylbenzo[b] furan-7-carboxamide hemifumarate); ATI-7505, a cisapride analog from ARYx Therapeutics; SDZ-216-454, a selective 5HT4 receptor agonist that stimulates cAMP formation in a concentration dependent manner (see Markstein et al. "Pharmacological characterisation of 5-HT receptors positively coupled to adenylyl cyclase in the rat hippocampus." *Naunyn Schmiedebergs Arch Pharmacol.* (1999) 359(6):454-9); SC-54750, or Aminomethylazaadamantane; Y-36912, or 4-amino-N-[1-[3-(benzylsulfonyl)propyl]piperidin-4-ylmethyl]-5-chloro-2-methoxybenzamide as disclosed by Sonda et al. ("Synthesis and pharmacological properties of benzamide derivatives as selective serotonin 4 receptor agonists." *Bioorg Med. Chem.* (2004) 12(10):2737-47); TKS159, or 4-amino-5-chloro-2-methoxy-N-[(2S,4S)-1-ethyl-2-hydroxymethyl-4-pyrrolidinyl] benzamide, as reported by Haga et al. ("Effect of TKS159, a novel 5-hydroxytryptamine-4 agonist, on gastric contractile activity in conscious dogs."; RS67333, or 1-(4-amino-5-chloro-2-methoxyphenyl)-3-(1-n-butyl-4-piperidinyl)-1-propanone; KDR-5169, or 4-amino-5-chloro-N-[1-(3-fluoro-4-methoxybenzyl)piperidin-4-yl]-2-(2-hydroxyethoxy)benzamide hydrochloride dihydrate as reported by Tazawa, et al. (2002) "KDR-5169, a new gastrointestinal prokinetic agent, enhances gastric contractile and emptying activities in dogs and rats." *Eur J Pharmacol* 434(3): 169-76); SL65.0155, or 5-(8-amino-7-chloro-2,3-dihydro-1,4-benzodioxin-5-yl)-3-[1-(2-phenyl ethyl)-4-piperidinyl]-1,3,4-oxadiazol-2(3H)-one monohydrochloride; and Y-34959, or 4-Amino-5-chloro-2-methoxy-N-[1-[5-(1-methylindol-3-ylcarbonylamino)pentyl]piperidin-4-ylmethyl]benzamide.

Other non-limiting reported 5HT4 receptor agonists and partial agonists for use in combination with a PDE agent include metoclopramide (CAS RN 364-62-5), 5-methoxytryptamine (CAS RN 608-07-1), RS67506 (CAS RN 168986-61-6), 2-[1-(4-piperonyl)piperazinyl]benzothiazole (CAS RN 155106-73-3), RS66331 (see Buccafusco et al. "Multiple Central Nervous System Targets for Eliciting Beneficial Effects on Memory and Cognition." (2000) Pharmacology 295(2):438-446), BIMU8 (endo-N-8-methyl-8-azabicyclo[3.2.1]oct-3-yl)-2,3-dehydro-2-oxo-3-(prop-2-yl)-1H-benzimid-azole-1-carboxamide), or SB 205149 (the n-butyl quaternary analog of renzapride). Compounds related to metoclopramide, such as metoclopramide dihydrochloride (CAS RN 2576-84-3) or metoclopramide dihydrochloride (CAS RN 5581-45-3) or metoclopramide hydrochloride (CAS RN 7232-21-5 or 54143-57-6) may also be used in a combination or method as described herein.

Additionally, the agent used with a PDE agent may be a reported 5HT3 receptor antagonist such as azasetron (CAS RN 123039-99-6); Ondansetron (CAS RN 99614-02-5) or Ondansetron hydrochloride (CAS RN 99614-01-4); Cilansetron (CAS RN 120635-74-7); Aloxi or Palonosetron Hydrochloride (CAS RN 135729-62-3); Palenosetron (CAS RN 135729-61-2 or 135729-56-5); Cisplatin (CAS RN 15663-27-1); Lotronex or Alosetron hydrochloride (CAS RN 122852-69-1); Anzemet or Dolasetron mesylate (CAS RN 115956-13-3); zacopride or R-Zacopride; E-3620 ([3(S)-endo]-4-amino-5-chloro-N-(8-methyl-8-azabicyclo[3.2.1-] oct-3-yl-2-[(1-methyl-2-butynyl)oxy]benzamide) or E-3620HCl (3(S)-endo-4-amino-5-chloro-N-(8-methyl-8-azabicyclo[3.2.1] oct-3-yl)-2-(1-methyl-2-butinyl)oxy)-benzamide-HCl); YM 060 or Ramosetron hydrochloride (CAS RN 132907-72-3); a thieno[2,3-d]pyrimidine derivative antagonist described in U.S. Pat. No. 6,846,823, such as DDP 225 or MCI-225 (CAS RN 135991-48-9); Marinol or Dronabinol (CAS RN 1972-08-3); or Lac Hydrin or Ammonium lactate (CAS RN 515-98-0); Kytril or Granisetron hydrochloride (CAS RN 107007-99-8); Bemesetron (CAS RN 40796-97-2); Tropisetron (CAS RN 89565-68-4); Zatosetron (CAS RN 123482-22-4); Mirisetron (CAS RN 135905-89-4) or Mirisetron maleate (CAS RN 148611-75-0); or renzapride (CAS RN 112727-80-7).

Additionally, the agent used with a PDE agent may be a reported 5HT2A/2C receptor antagonist such as Ketanserin (CAS RN 74050-98-9) or ketanserin tartrate; risperidone; olanzapine; adatanserin (CAS RN 127266-56-2); Ritanserin (CAS RN 87051-43-2); etoperidone; nefazodone; deramciclane (CAS RN 120444-71-5); Geoden or Ziprasidone hydrochloride (CAS RN 138982-67-9); Zeldox or Ziprasidone or Ziprasidone hydrochloride; EMD 281014 (7-[4-[2-(4-fluorophenyl)-ethyl]-piperazine-1-carbonyl]-1H-indole-3-carbonitrile HCl); MDL 100907 or M100907 (CAS RN 139290-65-6); Effexor XR (Venlafaxine formulation); Zomaril or Iloperidone; quetiapine (CAS RN 111974-69-7) or Quetiapine fumarate (CAS RN 111974-72-2) or Seroquel; SB 228357 or SB 243213 (see Bromidge et al. "Biarylcarbamoylindolines are novel and selective 5-HT(2C) receptor inverse agonists: identification of 5-methyl-1-[[2-[(2-methyl-3-pyridyl)oxy]-5-pyridyl]carbamoyl]-6-trifluoromethylindoline (SB-243213) as a potential antidepressant/anxiolytic agent." J Med. Chem. 2000 43(6):1123-34; SB 220453 or Tonabersat (CAS RN 175013-84-0); Sertindole (CAS RN 106516-24-9); Eplivanserin (CAS RN 130579-75-8) or Eplivanserin fumarate (CAS RN 130580-02-8); Lubazodone hydrochloride (CAS RN 161178-10-5); Cyproheptadine (CAS RN 129-03-3); Pizotyline or pizotifen (CAS RN 15574-96-6); Mesulergine (CAS RN 64795-35-3); Irindalone (CAS RN 96478-43-2); MDL 11939 (CAS RN 107703-78-6); or pruvanserin (CAS RN 443144-26-1).

Additional non-limiting examples of modulators include reported 5-HT2C agonists or partial agonists, such as m-chlorophenylpiperazine; or 5-HT2A receptor inverse agonists, such as ACP 103 (CAS RN: 868855-07-6), APD125 (from Arena Pharmaceuticals), AVE 8488 (from Sanofi-Aventis) or TGWOOAD/AA(from Fabre Kramer Pharmaceuticals).

Additionally, the agent used with a PDE agent may be a reported 5HT6 receptor antagonist such as SB-357134 (N-(2, 5-Dibromo-3-fluorophenyl)-4-methoxy-3-piperazin-1-yl-benzenesulfonamide); SB-271046 (5-chloro-N-(4-methoxy-3-(piperazin-1-yl)phenyl)-3-methylbenzo[b]thiophene-2-sulfonamide); Ro 04-06790 (N-(2,6-bis(methylamino) pyrimidin-4-yl)-4-aminobenzenesulfonamide); Ro 63-0563 (4-amino-N-(2,6 bis-methylamino-pyridin-4-yl)-benzene sulfonamide); clozapine or its metabolite N-desmethylclozapine; olanzapine (CAS RN 132539-06-1); fluperlapine (CAS RN 67121-76-0); seroquel (quetiapine or quetiapine fumarate); clomipramine (CAS RN 303-49-1); amitriptyline (CAS RN50-48-6); doxepin (CAS RN 1668-19-5); nortryptyline (CAS RN 72-69-5); 5-methoxytryptamine (CAS RN 608-07-1); bromocryptine (CAS RN 25614-03-3); octoclothepin (CAS RN 13448-22-1); chlorpromazine (CAS RN 50-53-3); loxapine (CAS RN 1977-10-2); fluphenazine (CAS RN 69-23-8); or GSK 742457 (presented by David Witty, "Early Optimisation of in vivo Activity: the discovery of 5-HT6 Receptor Antagonist 742457" GlaxoSmithKline at SCIpharm 2006, International Pharmaceutical Industry Conference in Edinburgh, 16 May 2006).

As an additional non-limiting example, the reported 5HT6 modulator may be SB-258585 (4-Iodo-N-[4-methoxy-3-(4-methyl-piperazin-1-yl)-phenyl]-benzen esulphonamide); PRX 07034 (from Predix Pharmaceuticals) or a partial agonist, such as E-6801 (6-chloro-N-(3-(2-(dimethylamino) ethyl)-1H-indol-5-yl)imidazo[2,1-b]thiazole-5-sulfonamide) or E-6837 (5-chloro-N-(3-(2-(dimethylamino)ethyl)-1H-indol-5-yl)naphthalene-2-sulfonamide).

Additionally, the agent used in combination with a PDE agent may be a reported compound (or "monoamine modulator") that modulates neurotransmission mediated by one or more monoamine neurotransmitters (referred to herein as "monoamines") or other biogenic amines, such as trace amines (TAs) as a non-limiting example. TAs are endogenous, CNS-active amines that are structurally related to classical biogenic amines (e.g., norepinephrine, dopamine (4-(2-aminoethyl)benzene-1,2-diol), and/or serotonin (5-hydroxytryptamine (5-HT), or a metabolite, precursor, prodrug, or analogue thereof. The methods of the disclosure thus include administration of one or more reported TAs in a combination with a PDE agent. Additional CNS-active monoamine receptor modulators are well known in the art, and are described, e.g., in the Merck Index, 12th Ed. (1996).

Certain food products, e.g., chocolates, cheeses, and wines, can also provide a significant dietary source of TAs and/or TA-related compounds. Non-limiting examples of mammalian TAs useful as constitutive factors include, but are not limited to, tryptamine, ρ-tyramine, m-tyramine, octopamine, synephrine or β-phenylethylamine (β-PEA). Additional useful TA-related compounds include, but are not limited to, 5-hydroxytryptamine, amphetamine, bufotenin, 5-methoxytryptamine, dihydromethoxytryptamine, phenylephrine, or a metabolite, precursor, prodrug, or analogue thereof.

In some embodiments, the constitutive factor is a biogenic amine or a ligand of a trace amine-associated receptor (TAAR), and/or an agent that mediates one or more biological effects of a TA. TAs have been shown to bind to and activate a number of unique receptors, termed TAARs, which comprise a family of G-protein coupled receptors (TAAR1-TAAR9) with homology to classical biogenic amine receptors. For example, TAAR1 is activated by both tyramine and β-PEA.

Thus non-limiting embodiments include methods and combination compositions wherein the constitutive factor is β-PEA, which has been indicated as having a significant neuromodulatory role in the mammalian CNS and is found at relatively high levels in the hippocampus (e.g., Taga et al., Biomed Chromatogr., 3(3): 118-20 (1989)); a metabolite, prodrug, precursor, or other analogue of β-PEA, such as the β-PEA precursor L-phenylalanine, the β-PEA metabolite β-phenylacetic acid (β-PAA), or the β-PEA analogues methylphenidate, amphetamine, and related compounds.

Most TAs and monoamines have a short half-life (e.g., less than about 30 s) due, e.g., to their rapid extracellular metabolism. Thus embodiments of the disclosure include use of a monoamine "metabolic modulator," which increases the extracellular concentration of one or more monoamines by inhibiting monoamine metabolism. In some embodiments, the metabolic modulator is an inhibitor of the enzyme monoamine oxidase (MAO), which catalyzes the extracellular breakdown of monoamines into inactive species. Isoforms MAO-A and/or MAO-B provide the major pathway for TA metabolism. Thus, in some embodiments, TA levels are regulated by modulating the activity of MAO-A and/or MAO-B. For example, in some embodiments, endogenous TA levels are increased (and TA signaling is enhanced) by administering an inhibitor of MAO-A and/or MAO-B, in combination with a PDE agent as described herein.

Non-limiting examples of inhibitors of monoamine oxidase (MAO) include reported inhibitors of the MAO-A isoform, which preferentially deaminates 5-hydroxytryptamine (serotonin) (5-HT) and norepinephrine (NE), and/or the MAO-B isoform, which preferentially deaminates phenylethylamine (PEA) and benzylamine (both MAO-A and MAO-B metabolize Dopamine (DA)). In various embodiments, MAO inhibitors may be irreversible or reversible (e.g., reversible inhibitors of MAO-A (RIMA)), and may have varying potencies against MAO-A and/or MAO-B (e.g., non-selective dual inhibitors or isoform-selective inhibitors). Non-limiting examples of MAO inhibitors useful in methods described herein include clorgyline, L-deprenyl, isocarboxazid (Marplan), ayahuasca, nialamide, iproniazide, iproclozide, moclobemide (Aurorix), phenelzine (Nardil), tranylcypromine (Pamate) (the congeneric of phenelzine), toloxatone, levo-deprenyl (Selegiline), harmala, RIMAs (e.g., moclobemide, described in Da Prada et al., J Pharmacol Exp Ther 248: 400-414 (1989); brofaromine; and befloxatone, described in Curet et al., J Affect Disord 51: 287-303 (1998)), lazabemide (Ro 19 6327), described in Ann. Neurol., 40(1): 99-107 (1996), and SL25.1131, described in Aubin et al., J. Pharmacol. Exp. Ther., 310: 1171-1182 (2004).

In additional embodiments, the monoamine modulator is an "uptake inhibitor," which increases extracellular monoamine levels by inhibiting the transport of monoamines away from the synaptic cleft and/or other extracellular regions. In some embodiments, the monoamine modulator is a monoamine uptake inhibitor, which may selectively/preferentially inhibit uptake of one or more monoamines relative to one or more other monoamines. The term "uptake inhibitors"

includes compounds that inhibit the transport of monoamines (e.g., uptake inhibitors) and/or the binding of monoamine substrates (e.g., uptake blockers) by transporter proteins (e.g., the dopamine transporter (DAT), the NE transporter (NET), the 5-HT transporter (SERT), and/or the extraneuronal monoamine transporter (EMT)) and/or other molecules that mediate the removal of extracellular monoamines. Monoamine uptake inhibitors are generally classified according to their potencies with respect to particular monoamines, as described, e.g., in Koe, *J. Pharmacol. Exp. Ther.* 199: 649-661 (1976). However, references to compounds as being active against one or more monoamines are not intended to be exhaustive or inclusive of the monoamines modulated in vivo, but rather as general guidance for the skilled practitioner in selecting compounds for use in therapeutic methods provided herein.

In embodiments relating to a biogenic amine modulator used in a combination or method with a PDE agent as disclosed herein, the modulator may be (i) a norepinephrine and dopamine reuptake inhibitor, such as bupropion (described, e.g., in U.S. Pat. Nos. 3,819,706 and 3,885,046), or (S,S)-hydroxybupropion (described, e.g., in U.S. Pat. No. 6,342, 496); (ii) selective dopamine reuptake inhibitors, such as medifoxamine, amineptine (described, e.g., in U.S. Pat. Nos. 3,758,528 and 3,821,249), GBR12909, GBR12783 and GBR13069, described in Andersen, *Eur J Pharmacol*, 166: 493-504 (1989); or (iii) a monoamine "releaser" which stimulates the release of monoamines, such as biogenic amines from presynaptic sites, e.g., by modulating presynaptic receptors (e.g., autoreceptors, heteroreceptors), modulating the packaging (e.g., vesicular formation) and/or release (e.g., vesicular fusion and release) of monoamines, and/or otherwise modulating monoamine release. Advantageously, monoamine releasers provide a method for increasing levels of one or more monoamines within the synaptic cleft or other extracellular region independently of the activity of the presynaptic neuron.

Monoamine releasers useful in combinations provided herein include fenfluramine or p-chloroamphetamine (PCA) or the dopamine, norepinephrine, and serotonin releasing compound amineptine (described, e.g., in U.S. Pat. Nos. 3,758,528 and 3,821,249).

Furthermore, the neurogenic agent in combination with a PDE agent may be a reported neurosteroid. Non-limiting examples of such a neurosteroid include pregnenolone and allopregnenalone.

Alternatively, the neurogenic sensitizing agent may be a reported non-steroidal anti-inflammatory drug (NSAID) or an anti-inflammatory mechanism targeting agent in general. Non-limiting examples of a reported NSAID include a cyclooxygenase inhibitor, such as indomethacin, ibuprofen, celecoxib, cofecoxib, naproxen, or aspirin. Additional non-limiting examples for use in combination with a PDE agent include rofecoxib, meloxicam, piroxicam, valdecoxib, parecoxib, etoricoxib, etodolac, nimesulide, acemetacin, bufexamac, diflunisal, ethenzamide, etofenamate, flobufen, isoxicam, kebuzone, lonazolac, meclofenamic acid, metamizol, mofebutazone, niflumic acid, oxyphenbutazone, paracetamol, phenidine, propacetamol, propyphenazone, salicylamide, tenoxicam, tiaprofenic acid, oxaprozin, lornoxicam, nabumetone, minocycline, benorylate, aloxiprin, salsalate, flurbiprofen, ketoprofen, fenoprofen, fenbufen, benoxaprofen, suprofen, piroxicam, meloxicam, diclofenac, ketorolac, fenclofenac, sulindac, tolmetin, xyphenbutazone, phenylbutazone, feprazone, azapropazone, flufenamic acid or mefenamic acid.

In additional embodiments, the neurogenic agent in combination with a PDE agent may be a reported agent for treating migraines. Non-limiting examples of such an agent include a triptan, such as almotriptan or almotriptan malate; naratriptan or naratriptan hydrochloride; rizatriptan or rizatriptan benzoate; sumatriptan or sumatriptan succinate; zolmatriptan or zolmitriptan, frovatriptan or frovatriptan succinate; or eletriptan or eletriptan hydrobromide. Embodiments of the disclosure may exclude combinations of triptans and an SSRI or SNRI that result in life threatening serotonin syndrome.

Other non-limiting examples include an ergot derivative, such as dihydroergotamine or dihydroergotamine mesylate, ergotamine or ergotamine tartrate; diclofenac or diclofenac potassium or diclofenac sodium; flurbiprofen; amitriptyline; nortriptyline; divalproex or divalproex sodium; propranolol or propranolol hydrochloride; verapamil; methysergide (CAS RN 361-37-5); metoclopramide; prochlorperazine (CAS RN 58-38-8); acetaminophen; topiramate; GW274150 ([2-[(1-iminoethyl) amino]ethyl]-L-homocysteine); or ganaxalone (CAS RN 38398-32-2).

Additional non-limiting examples include a COX-2 inhibitor, such as Celecoxib.

In other embodiments, the neurogenic agent in combination with a PDE agent may be a reported modulator of a nuclear hormone receptor. Nuclear hormone receptors are activated via ligand interactions to regulate gene expression, in some cases as part of cell signaling pathways. Non-limiting examples of a reported modulator include a dihydrotestosterone agonist such as dihydrotestosterone; a 2-quinolone like LG121071 (4-ethyl-1,2,3,4-tetrahydro-6-(trifluoromethyl)-8-pyridono[5,6-g]-quinoline); a non-steroidal agonist or partial agonist compound described in U.S. Pat. No. 6,017,924; LGD2226 (see WO 01/16108, WO 01/16133, WO 01/16139, and Rosen et al. "Novel, non-steroidal, selective androgen receptor modulators (SARMs) with anabolic activity in bone and muscle and improved safety profile." *J Musculoskelet Neuronal Interact.* 2002 2(3):222-4); or LGD2941 (from collaboration between Ligand Pharmaceuticals Inc. and TAP Pharmaceutical Products Inc.).

Additional non-limiting examples of a reported modulator include a selective androgen receptor modulator (SARM) such as andarine, ostarine, prostarin, or andromustine (all from GTx, Inc.); bicalutamide or a bicalutamide derivative such as GTx-007 (U.S. Pat. No. 6,492,554); or a SARM as described in U.S. Pat. No. 6,492,554.

Further non-limiting examples of a reported modulator include an androgen receptor antagonist such as cyproterone, bicalutamide, flutamide, or nilutamide; a 2-quinolone such as LG120907, represented by the following structure

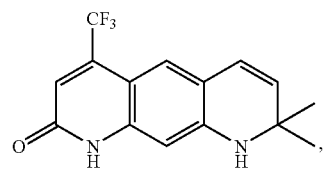

or a derivative compound represented by the following structure

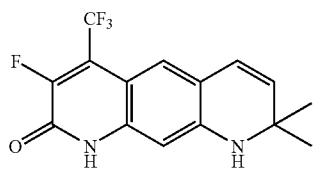

(see Allan et al. "Therapeutic androgen receptor ligands" *Nucl Recept Signal* 2003; 1: e009); a phthalamide, such as a modulator as described by Miyachi et al. ("Potent novel non-steroidal androgen antagonists with a phthalimide skeleton." *Bioorg. Med. Chem. Lett.* 1997 7:1483-1488); osaterone or osaterone acetate; hydroxyflutamide; or a non-steroidal antagonist described in U.S. Pat. No. 6,017,924.

Other non-limiting examples of a reported modulator include a retinoic acid receptor agonist such as all-trans retinoic acid (Tretinoin); isotretinoin (13-cis-retinoic acid); 9-cis retinoic acid; bexarotene; TAC-101 (4-[3,5-bis (trimethylsilyl) benzamide] benzoic acid); AC-261066 (see Lund et al. "Discovery of a potent, orally available, and isoform-selective retinoic acid beta2 receptor agonist." *J Med. Chem.* 2005 48(24):7517-9); LGD1550 ((2E,4E,6E)-3-methyl-7-(3, 5-di-ter-butylphen-yl)octatrienoic acid); E6060 (E6060 [4-{5-[7-fluoro-4-(trifluoromethyl)benzo[b]furan-2-yl]-1H-2-pyrrolyl}benzoic acid]; agonist 1 or 2 as described by Schapira et al. ("In silico discovery of novel Retinoic Acid Receptor agonist structures." *BMC Struct Biol.* 2001; 1: 1 (published online 2001 Jun. 4) where "Agonist 1 was purchased from Bionet Research (catalog number 1G-433S). Agonist 2 was purchased from Sigma-Aldrich (Sigma Aldrich library of rare chemicals. Catalog number S08503-1"); a synthetic acetylenic retinoic acid, such as AGN 190121 (CAS RN: 132032-67-8), AGN 190168 (or Tazarotene or CAS RN 118292-40-3), or its metabolite AGN 190299 (CAS RN 118292-41-4); Etretinate; acitretin; an acetylenic retinoate, such as AGN 190073 (CAS 132032-68-9), or AGN 190089 (or 3-Pyridinecarboxylic acid, 6-(4-(2,6,6-trimethyl-1-cyclohexen-1-yl)-3-buten-1-ynyl)-, ethyl ester or CAS RN 116627-73-7).

In further embodiments, the additional agent for use in combination with a PDE agent may be a reported modulator selected from thyroxin, tri-iodothyronine, or levothyroxine.

Alternatively, the additional agent is a vitamin D (1,25-dihydroxyvitamine D$_3$) receptor modulator, such as calcitriol or a compound described in Ma et al. ("Identification and characterization of noncalcemic, tissue-selective, nonsecosteroidal vitamin D receptor modulators." *J Clin Invest.* 2006 116(4):892-904) or Molnar et al. ("Vitamin D receptor agonists specifically modulate the volume of the ligand-binding pocket." *J Biol. Chem.* 2006 281(15):10516-26) or Milliken et al. ("EB1089, a vitamin D receptor agonist, reduces proliferation and decreases tumor growth rate in a mouse model of hormone-induced mammary cancer." *Cancer Lett.* 2005 229(2):205-15) or Yee et al. ("Vitamin D receptor modulators for inflammation and cancer." *Mini Rev Med. Chem.* 2005 5(8):761-78) or Adachi et al. "Selective activation of vitamin D receptor by lithocholic acid acetate, a bile acid derivative." *J Lipid Res.* 2005 46(1):46-57).

Furthermore, the additional agent may be a reported cortisol receptor modulator, such as methylprednisolone or its prodrug methylprednisolone suleptanate; PI-1020 (NCX-1020 or budesonide-21-nitrooxymethylbenzoate); fluticasone furoate; GW-215864; betamethasone valerate; beclomethasone; prednisolone; or BVT-3498 (AMG-311).

Alternatively, the additional agent may be a reported aldosterone (or mineralocorticoid) receptor modulator, such as Spironolactone or Eplerenone.

In other embodiments, the additional agent may be a reported progesterone receptor modulator such as Asoprisnil (CAS RN 199396-76-4); mesoprogestin or J1042; J956; medroxyprogesterone acetate (MPA); R5020; tanaproget; trimegestone; progesterone; norgestomet; melengestrol acetate; mifepristone; onapristone; ZK137316; ZK230211 (see Fuhrmann et al. "Synthesis and biological activity of a novel, highly potent progesterone receptor antagonist." *J Med. Chem.* 2000 43(26):5010-6); or a compound described in Spitz "Progesterone antagonists and progesterone receptor modulators: an overview." *Steroids* 2003 68(10-13):981-93.

In further embodiments, the additional agent may be a reported i) peroxisome proliferator-activated receptor (PPAR) agonist such as muraglitazar; tesaglitazar; reglitazar; GW-409544 (see Xu et al. "Structural determinants of ligand binding selectivity between the peroxisome proliferator-activated receptors." *Proc Natl Acad Sci USA.* 2001 98(24): 13919-24); or DRL 11605 (Dr. Reddy's Laboratories); ii) a peroxisome proliferator-activated receptor alpha agonist like clofibrate; ciprofibrate; fenofibrate; gemfibrozil; DRF-10945 (Dr. Reddy's Laboratories); iii) a peroxisome proliferator-activated receptor delta agonist such as GW501516 (CAS RN 317318-70-0); or iv) a peroxisome proliferator-activated gamma receptor agonist like a hydroxyoctadecadienoic acid (HODE); a prostaglandin derivative, such as 15-deoxy-Delta 12,14-prostaglandin J2; a thiazolidinedione (glitazone), such as pioglitazone, troglitazone; rosiglitazone or rosiglitazone maleate; ciglitazone; Balaglitazone or DRF-2593; AMG 131 (from Amgen); or G1262570 (from GlaxoWellcome). In additional embodiments, a PPAR ligand is a PPARγ antagonist such as T0070907 (CAS RN 313516-66-4) or GW9662 (CAS RN 22978-25-2).

In additional embodiments, the additional agent may be a reported modulator of an "orphan" nuclear hormone receptor. Embodiments include a reported modulator of a liver X receptor, such as a compound described in U.S. Pat. No. 6,924,311; a farnesoid X receptor, such as GW4064 as described by Maloney et al. ("Identification of a chemical tool for the orphan nuclear receptor FXR." *J Med. Chem.* 2000 43(16):2971-4); a RXR receptor; a CAR receptor, such as 1,4-bis[2-(3,5-dichloropyridyloxy)] benzene (TCPOBOP); or a PXR receptor, such as SR-12813 (tetra-ethyl 2-(3,5-di-tert-butyl-4-hydroxyphenyl)ethenyl-1,1-bisphosphonate).

In additional embodiments, the agent in combination with a PDE agent is ethyl eicosapentaenoate or ethyl-EPA (also known as 5,8,11,14,17-eicosapentaenoic acid ethyl ester or miraxion, CAS RN 86227-47-6), docosahexaenoic acid (DHA), or a retinoid acid drug. As an additional non-limiting example, the agent may be Omacor, a combination of DHA and EPA, or idebenone (CAS RN 58186-27-9).

In further embodiments, a reported nootropic compound may be used as an agent in combination with a PDE agent. Non-limiting examples of such a compound include Piracetam (Nootropil), Aniracetam, Oxiracetam, Pramiracetam, Pyritinol (Enerbol), Ergoloid mesylates (Hydergine), Galantamine or Galantamine hydrobromide, Selegiline, Centrophenoxine (Lucidril), Desmopressin (DDAVP), Nicergoline, Vinpocetine, Picamilon, Vasopressin, Milacemide, FK-960, FK-962, levetiracetam, nefiracetam, or hyperzine A (CAS RN: 102518-79-6).

Additional non-limiting examples of such a compound include anapsos (CAS RN 75919-65-2), nebracetam (CAS RN 97205-34-0 or 116041-13-5), metrifonate, ensaculin (or CAS RN 155773-59-4 or KA-672) or ensaculin HCl, Rokan (CAS RN 122933-57-7 or EGb 761), AC-3933 (5-(3-methoxyphenyl)-3-(5-methyl-1,2,4-oxadiazol-3-yl)-2-oxo-1,2-dihydro-1,6-naphthyridine) or its hydroxylated metabolite SX-5745 (3-(5-hydroxymethyl-1,2,4-oxadiazol-3-yl)-5-(3-methoxyphenyl)-2-oxo-1,2-dihydro-1,6-naphthyridine), JTP-2942 (CAS RN 148152-77-6), sabeluzole (CAS RN 104383-17-7), ladostigil (CAS RN 209394-27-4), choline alphoscerate (CAS RN 28319-77-9 or Gliatilin), Dimebon (CAS RN 3613-73-8), tramiprosate (CAS RN 3687-18-1), omigapil (CAS RN 181296-84-4), cebaracetam (CAS RN 113957-09-8), fasoracetam (CAS RN 110958-19-5), PD-151832 (see Jaen et al. "In vitro and in vivo evaluation of the subtype-selective muscarinic agonist PD 151832." *Life Sci.* 1995 56(11-12):845-52), Vinconate (CAS RN 70704-03-9), PYM-50028 PYM-50028 (Cogane) or PYM-50018 (Myogane) as described by Harvey ("Natural Products in Drug Discovery and Development. 27-28 Jun. 2005, London, UK." IDrugs. 2005 8(9):719-21), SR-46559A (3-[N-(2 diethyl-amino-2-methylpropyl)-6-phenyl-5-propyl), dihydroergocristine (CAS RN 17479-19-5), dabelotine (CAS RN 118976-38-8), zanapezil (CAS RN 142852-50-4).

Further non-limiting examples include NBI-113 (from Neurocrine Biosciences, Inc.), NDD-094 (from Novartis), P-58 or P58 (from Pfizer), or SR-57667 (from Sanofi-Synthelabo).

Moreover, an agent in combination with a PDE agent may be a reported modulator of the nicotinic receptor. Non-limiting examples of such a modulator include nicotine, acetylcholine, carbamylcholine, epibatidine, ABT-418 (structurally similar to nicotine, with an ixoxazole moiety replacing the pyridyl group of nicotine), epiboxidine (a structural analogue with elements of both epibatidine and ABT-418), ABT-594 (azetidine analogue of epibatidine), lobeline, SSR-591813, represented by the following formula

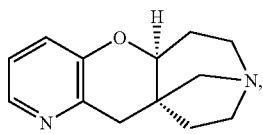

or SIB-1508 (altinicline).

In additional embodiments, an agent used in combination with a PDE agent is a reported aromatase inhibitor. Reported aromatase inhibitors include, but are not limited to, nonsteroidal or steroidal agents. Non-limiting examples of the former, which inhibit aromatase via the heme prosthetic group, include anastrozole (Arimidex®), letrozole (Femara®), or vorozole (Rivisor). Non-limiting examples of steroidal aromatase inhibitors AIs, which inactivate aromatase, include, but are not limited to, exemestane (Aromasin®), androstenedione, or formestane (lentaron).

Additional non-limiting examples of a reported aromatase for use in a combination or method as disclosed herein include aminoglutethimide, 4-androstene-3,6,17-trione (or "6-OXO"), or zoledronic acid or Zometa (CAS RN 118072-93-8).

Further embodiments include a combination of a PDE agent and a reported selective estrogen receptor modulator (SERM) may be used as described herein. Non-limiting examples include tamoxifen, raloxifene, toremifene, clomifene, bazedoxifene, arzoxifene, or lasofoxifene. Additional non-limiting examples include a steroid antagonist or partial agonist, such as centchroman, clomiphene, or droloxifene), In other embodiments, a combination of a PDE agent and a reported cannabinoid receptor modulator may be used as described herein. Non-limiting examples include synthetic cannabinoids, endogenous cannabinoids, or natural cannabinoids. In some embodiments, the reported cannabinoid receptor modulator is rimonabant (SR141716 or Acomplia), nabilone, levonantradol, marinol, or sativex (an extract containing both THC and CBD). Non-limiting examples of endogenous cannabinoids include arachidonyl ethanolamine (anandamide); analogs of anandamide, such as docosatetraenylethanolamide or homo-γ-linoenylethanolamide; N-acyl ethanolamine signalling lipids, such as the noncannabimimetic palmitoylethanolamine or oleoylethanolamine; or 2-arachidonyl glycerol. Non-limiting examples of natural cannabinoids include tetrahydrocannabinol (THC), cannabidiol (CBD), cannabinol (CBN), cannabigerol (CBG), cannabichromene (CBC), cannabicyclol (CBL), cannabivarol (CBV), tetrahydrocannabivarin (THCV), cannabidivarin (CBDV), cannabichromevarin (CBCV), cannabigerovarin (CBGV), or cannabigerol monoethyl ether (CBGM).

In yet further embodiments, an agent used in combination with a PDE agent is a reported FAAH (fatty acid amide hydrolase) inhibitor. Non-limiting examples of reported inhibitor agents include URB597 (3'-carbamoyl-biphenyl-3-yl-cyclohexylcarbamate); CAY10401 (1-oxazolo[4,5-b]pyridin-2-yl-9-octadecyn-1-one); OL-135 (1-oxo-1[5-(2-pyridyl)-2-yl]-7-phenylheptane); anandamide (CAS RN 94421-68-8); AA-5-HT (see Bisogno et al. "Arachidonoylserotonin and other novel inhibitors of fatty acid amide hydrolase." *Biochem Biophys Res Commun.* 1998 248(3):515-22); 1-Octanesulfonyl fluoride; or 0-2142 or another arvanil derivative FAAH inhibitor as described by Di Marzo et al. ("A structure/activity relationship study on arvanil, an endocannabinoid and vanilloid hybrid." *J Pharmacol Exp Ther.* 2002 300(3):984-91).

Further non-limiting examples include SSR 411298 (from Sanofi-Aventis), JNJ28614118 (from Johnson & Johnson), or SSR 101010 (from Sanofi-Aventis)

In additional embodiments, an agent in combination with a PDE agent may be a reported modulator of nitric oxide function. One non-limiting example is sildenafil (Viagra®).

In additional embodiments, an agent in combination with a PDE agent may be a reported modulator of prolactin or a prolactin modulator.

In additional embodiments, an agent in combination with a PDE agent is a reported anti-viral agent, with ribavirin and amantadine as non-limiting examples.

In additional embodiments, an agent in combination with a PDE agent may be a component of a natural product or a derivative of such a component. In some embodiments, the component or derivative thereof is in an isolated form, such as that which is separated from one or more molecules or macromolecules normally found with the component or derivative before use in a combination or method as disclosed herein. In other embodiments, the component or derivative is completely or partially purified from one or more molecules or macromolecules normally found with the component or derivative. Exemplary cases of molecules or macromolecules found with a component or derivative as described herein include a plant or plant part, an animal or animal part, and a food or beverage product.

Non-limiting examples such a component include folic acid; a flavinoid, such as a citrus flavonoid; a flavonol, such as Quercetin, Kaempferol, Myricetin, or Isorhamnetin; a flavone, such as Luteolin or Apigenin; a flavanone, such as Hesperetin, Naringenin, or Eriodictyol; a flavan-3-ol (including a monomeric, dimeric, or polymeric flavanol), such as (+)-Catechin, (+)-Gallocatechin, (−)-Epicatechin, (−)-Epigallocatechin, (−)-Epicatechin 3-gallate, (−)-Epigallocatechin 3-gallate, Theaflavin, Theaflavin 3-gallate, Theaflavin 3'-gallate, Theaflavin 3,3' digallate, a Thearubigin, or Proanthocyanidin; an anthocyanidin, such as Cyanidin, Delphinidin, Malvidin, Pelargonidin, Peonidin, or Petunidin; an isoflavone, such as daidzein, genistein, or glycitein; flavopiridol; a prenylated chalcone, such as Xanthohumol; a prenylated flavanone, such as Isoxanthohumol; a non-prenylated chalcone, such as Chalconaringenin; a non-prenylated flavanone, such as Naringenin; Resveratrol; or an anti-oxidant neutraceutical (such as any present in chocolate, like dark chocolate or unprocessed or unrefined chocolate).

Additional non-limiting examples include a component of Gingko biloba, such as a flavo glycoside or a terpene. In some embodiments, the component is a flavanoid, such as a flavonol or flavone glycoside, or a quercetin or kaempferol glycoside, or rutin; or a terpenoid, such as ginkgolides A, B, C, or M, or bilobalide.

Further non-limiting examples include a component that is a flavanol, or a related oligomer, or a polyphenol as described in US2005/245601AA, US2002/018807AA, US2003/180406AA, US2002/086833AA, US2004/0236123, WO9809533, or WO9945788; a procyanidin or derivative thereof or polyphenol as described in US2005/171029AA; a procyanidin, optionally in combination with L-arginine as described in US2003/104075AA; a low fat cocoa extract as described in US2005/031762AA; lipophilic bioactive compound containing composition as described in US2002/107292AA; a cocoa extract, such as those containing one or more polyphenols or procyanidins as described in US2002/004523AA; an extract of oxidized tea leaves as described in U.S. Pat. No. 5,139,802 or 5,130,154; a food supplement as described in WO 2002/024002.

Of course a composition comprising any of the above components, alone or in combination with a PDE agent as described herein is included within the disclosure.

In additional embodiments, an agent in combination with a PDE agent may be a reported calcitonin receptor agonist such as calcitonin or the 'orphan peptide' PHM-27 (see Ma et al. "Discovery of novel peptide/receptor interactions: identification of PHM-27 as a potent agonist of the human calcitonin receptor." *Biochem Pharmacol.* 2004 67(7): 1279-84). A further non-limiting example is the agonist from Kemia, Inc.

In an alternative embodiment, the agent may be a reported modulator of parathyroid hormone activity, such as parathyroid hormone, or a modulator of the parathyroid hormone receptor.

In additional embodiments, an agent in combination with a PDE agent may a reported antioxidant, such as N-acetylcysteine or acetylcysteine; disufenton sodium (or CAS RN 168021-79-2 or Cerovive); activin (CAS RN 104625-48-1); selenium; L-methionine; an alpha, gamma, beta, or delta, or mixed, tocopherol; alpha lipoic acid; Coenzyme Q; Benzimidazole; benzoic acid; dipyridamole; glucosamine; IRFI-016 (2(2,3-dihydro-5-acetoxy-4,6,7-trimethylbenzofuranyl) acetic acid); L-carnosine; L-Histidine; glycine; flavocoxid (or LIMBREL); baicalin, optionally with catechin (3,3',4',5,7-pentahydroxyflavan (2R,3S form)), and/or its stereo-isomer; masoprocol (CAS RN 27686-84-6); mesna (CAS RN 19767-45-4); probucol (CAS RN 23288-49-5); silibinin (CAS RN 22888-70-6); sorbinil (CAS RN 68367-52-2); spermine; tangeretin (CAS RN 481-53-8); butylated hydroxyanisole (BHA); butylated hydroxytoluene (BHT); propyl gallate (PG); tertiary-butylhydroquinone (TBHQ); nordihydroguaiaretic acid (CAS RN 500-38-9); astaxanthin (CAS RN 472-61-7); or an antioxidant flavonoid.

Additional non-limiting examples include a vitamin, such as vitamin A (Retinol) or C (Ascorbic acid) or E (including Tocotrienol and/or Tocopherol); a vitamin cofactors or mineral, such as Coenzyme Q10 (CoQ10), Manganese, or Melatonin; a carotenoid terpenoid, such as Lycopene, Lutein, Alpha-carotene, Beta-carotene, Zeaxanthin, Astaxanthin, or Canthaxantin; a non-carotenoid terpenoid, such as Eugenol; a flavonoid polyphenolic (or bioflavonoid); a flavonol, such as Resveratrol, Pterostilbene (methoxylated analogue of resveratrol), Kaempferol, Myricetin, Isorhamnetin, a Proanthocyanidin, or a tannin; a flavone, such as Quercetin, rutin, Luteolin, Apigenin, or Tangeritin; a flavanone, such as Hesperetin or its metabolite hesperidin, naringenin or its precursor naringin, or Eriodictyol; a flavan-3-ols (anthocyanidins), such as Catechin, Gallocatechin, Epicatechin or a gallate form thereof, Epigallocatechin or a gallate form thereof, Theaflavin or a gallate form thereof, or a Thearubigin; an isoflavone phytoestrogens, such as Genistein, Daidzein, or Glycitein; an anthocyanins, such as Cyanidin, Delphinidin, Malvidin, Pelargonidin, Peonidin, or Petunidin; a phenolic acid or ester thereof, such as Ellagic acid, Gallic acid, Salicylic acid, Rosmarinic acid, Cinnamic acid or a derivative thereof like ferulic acid, Chlorogenic acid, Chicoric acid, a Gallotannin, or an Ellagitannin; a nonflavonoid phenolic, such as Curcumin; an anthoxanthin, betacyanin, Citric acid, Uric acid, R-α-lipoic acid, or Silymarin.

Further non-limiting examples include 1-(carboxymethylthio)tetradecane; 2,2,5,7,8-pentamethyl-1-hydroxychroman; 2,2,6,6-tetramethyl-4-piperidinol-N-oxyl; 2,5-di-tert-butylhydroquinone; 2-tert-butylhydroquinone; 3,4-dihydroxyphenylethanol; 3-hydroxypyridine; 3-hydroxytamoxifen; 4-coumaric acid; 4-hydroxyanisole; 4-hydroxyphenylethanol; 4-methylcatechol; 5,6,7,8-tetrahydrobiopterin; 6,6'-methylenebis(2,2-dimethyl-4-methanesulfonic acid-1,2-dihydroquinoline); 6-hydroxy-2,5,7,8-tetramethylchroman-2-carboxylic acid; 6-methyl-2-ethyl-3-hydroxypyridine; 6—O-palmitoylascorbic acid; acetovanillone; acteoside; Actovegin; allicin; allyl sulfide; alpha-pentyl-3-(2-quinolinylmethoxy)benzenemethanol; alpha-tocopherol acetate; apolipoprotein A-IV; bemethyl; boldine; bucillamine; Calcium Citrate; Canthaxantin; crocetin; diallyl trisulfide; dicarbine; dihydrolipoic acid; dimephosphon; ebselen; Efamol; enkephalin-Leu, Ala(2)-Arg(6)-; Ergothioneine; esculetin; essential 303 forte; Ethonium; etofyllinclofibrate; fenozan; glaucine; H290-51; histidyl-proline diketopiperazine; hydroquinone; hypotaurine; idebenone; indole-3-carbinol; isoascorbic acid; kojic acid, lacidipine, Iodoxamide tromethamine; mexidol; morin; N,N'-diphenyl-4-phenylenediamine; N-isopropyl-N-phenyl-4-phenylenediamine; N-monoacetylcystine; nicaraven, nicotinoyl-GABA; nitecapone; nitroxyl; nobiletin; oxymethacil; p-tert-butyl catechol; phenidone; pramipexol; proanthocyanidin; procyanidin; prolinedithiocarbamate; Propyl Gallate; purpurogallin; pyrrolidine dithiocarbamic acid; rebamipide; retinol palmitate; salvin; Selenious Acid; sesamin; sesamol; sodium selenate; sodium thiosulfate; theaflavin; thiazolidine-4-carboxylic acid; tirilazad; tocopherylquinone; tocotrienol, alpha; a Tocotrienol; tricyclodecane-9-yl-xanthogenate; turmeric extract; U 74389F; U 74500A; U 78517F; ubiquinone 9; vanillin; vinpocetine; xylometazoline; zeta Carotene; zilascorb; zinc thionein; or zonisamide.

In additional embodiments, an agent in combination with a PDE agent may be a reported modulator of a norepinephrine receptor. Non-limiting examples include Atomoxetine (Strattera); a norepinephrine reuptake inhibitor, such as talsupram, tomoxetine, nortriptyline, nisoxetine, reboxetine (described, e.g., in U.S. Pat. No. 4,229,449), or tomoxetine (described, e.g., in U.S. Pat. No. 4,314,081); or a direct agonist, such as a beta adrenergic agonist.

Additional non-limiting examples include an alpha adrenergic agonist such as etilefrine or a reported agonist of the α2-adrenergic receptor (or α2 adrenoceptor) like clonidine (CAS RN 4205-90-7), yohimbine, mirtazepine, atipamezole, carvedilol; dexmedetomidine or dexmedetomidine hydrochloride; ephedrine, epinephrine; etilefrine; lidamidine; tetramethylpyrazine; tizanidine or tizanidine hydrochloride; apraclonidine; bitolterol mesylate; brimonidine or brimonidine tartrate; dipivefrin (which is converted to epinephrine in vivo); guanabenz; guanfacine; methyldopa; alphamethylnoradrenaline; mivazerol; natural ephedrine or D(−)ephedrine; any one or any mixture of two, three, or four of the optically active forms of ephedrine; CHF1035 or nolomirole hydrochloride (CAS RN 138531-51-8); or lofexidine (CAS RN 31036-80-3).

Alternative non-limiting examples include an adrenergic antagonist such as a reported antagonist of the α2-adrenergic receptor like yohimbine (CAS RN 146-48-5) or yohimbine hydrochloride, idazoxan, fluparoxan, mirtazepine, atipamezole, or RX781094 (see Elliott et al. "Peripheral pre and postjunctional alpha 2-adrenoceptors in man: studies with RX781094, a selective alpha 2 antagonist." *J Hypertens Suppl.* 19831(2):109-11).

Other non-limiting embodiments include a reported modulator of an α1-adrenergic receptor such as cirazoline; modafinil; ergotamine; metaraminol; methoxamine; midodrine (a prodrug which is metabolized to the major metabolite desglymidodrine formed by deglycination of midodrine); oxymetazoline; phenylephrine; phenylpropanolamine; or pseudoephedrine.

Further non-limiting embodiments include a reported modulator of a beta adrenergic receptor such as arbutamine, befunolol, cimaterol, higenamine, isoxsuprine, methoxyphenamine, oxyfedrine, ractopamine, tretoquinol, or TQ-1016 (from TheraQuest Biosciences, LLC), or a reported β1-adrenergic receptor modulator such as prenalterol, Ro 363, or xamoterol or a reported β1-adrenergic receptor agonist like dobutamine.

Alternatively, the reported modulator may be of a β2-adrenergic receptor such as levosalbutamol (CAS RN 34391-04-3), metaproterenol, MN-221 or KUR-1246 ((−)-bis(2-{[(2S)-2-({(2R)-2-hydroxy-2-[4-hydroxy-3-(2-hydroxyethyl) phenyl]ethyl}amino)-1,2,3,4-tetrahydronaphthalen-7-yl] oxy}-N,N-dimethylacetamide)monosulfate or bis(2-[[(2S)-2-([(2R)-2-hydroxy-2-[4-hydroxy-3-(2-hydroxyethyl)-phenyl]ethyl]amino)-1,2,3,4-tetrahydronaphthalen-7-yl]oxy]-N,N-dimethylacetamide) sulfate or CAS RN 194785-31-4), nylidrin, orciprenaline, pirbuterol, procaterol, reproterol, ritodrine, salmeterol, salmeterol xinafoate, terbutaline, tulobuterol, zinterol or bromoacetylalprenololmenthane, or a reported β2-adrenergic receptor agonist like albuterol, albuterol sulfate, salbutamol (CAS RN 35763-26-9), clenbuterol, broxaterol, dopexamine, formoterol, formoterol fumarate, isoetharine, levalbuterol tartrate hydrofluoroalkane, or mabuterol.

Additional non-limiting embodiments include a reported modulator of a 3-adrenergic receptor such as AJ-9677 or TAK677 ([3-[(2R)-[[(2R)-(3-chlorophenyl)-2-hydroxyethyl]amino]propyl]-1H-indol-7-yloxy]acetic acid), or a reported β3-adrenergic receptor agonist like SR58611A (described in Simiand et al., Eur J Pharmacol, 219:193-201 (1992), BRL 26830A, BRL 35135, BRL 37344, CL 316243 or ICI D7114.

Further alternative embodiments include a reported nonselective alpha and beta adrenergic receptor agonist such as epinephrine or ephedrine; a reported nonselective alpha and beta adrenergic receptor antagonist such as carvedilol; a β1 and β2 adrenergic receptor agonist such as isopreoterenol; or a β1 and β2 adrenergic receptor antagonist such as CGP 12177, fenoterol, or hexoprenaline.

In further embodiments, an agent in combination with a PDE agent may be a reported modulator of carbonic anhydrase. Non-limiting examples of such an agent include acetazolamide, benzenesulfonamide, benzolamide, brinzolamide, dichlorphenamide, dorzolamide or dorzolamide HCl, ethoxzolamide, flurbiprofen, mafenide, methazolamide, sezolamide, zonisamide, bendroflumethiazide, benzthiazide, chlorothiazide, cyclothiazide, dansylamide, diazoxide, ethinamate, furosemide, hydrochlorothiazide, hydroflumethiazide, mercuribenzoic acid, methyclothiazide, trichloromethazide, amlodipine, cyanamide, or a benzenesulfonamide. Additional non-limitinge examples of such an agent include (4s-Trans)-4-(Ethylamino)-5,6-Dihydro-6-Methyl-4-h-Thieno(2,3-B)Thiopyran-2-Sulfonamide-7,7-Dioxide; (4s-Trans)-4-(Methylamino)-5,6-Dihydro-6-Methyl-4-h-Thieno(2,3-B)Thiopyran-2-Sulfonamide-7,7-Dioxide; (R)—N-(3-Indol-1-yl-2-Methyl-Propyl)-4-Sulfamoyl-Benzamide; (S)—N-(3-Indol-1-yl-2-Methyl-Propyl)-4-Sulfamoyl-Benzamide; 1,2,4-Triazole; 1-Methyl-3-Oxo-1,3-Dihydro-Benzo[C]Isothiazole-5-Sulfonic Acid Amide; 2,6-Difluorobenzenesulfonamide; 3,5-Difluorobenzenesulfonamide; 3-Mercuri-4-Aminobenzenesulfonamide; 3-Nitro-4-(2-Oxo-Pyrrolidin-1-yl)-Benzenesulfonamide; 4-(Aminosulfonyl)-N-[(2,3,4-Trifluorophenyl)Methyl]-Benzamide; 4-(Aminosulfonyl)-N-[(2,4,6-Trifluorophenyl)Methyl]-Benzamide; 4-(Aminosulfonyl)-N-[(2,4-Difluorophenyl)Methyl]-Benzamide; 4-(Aminosulfonyl)-N-[(2,5-Difluorophenyl)Methyl]-Benzamide; 4-(Aminosulfonyl)-N-[(3,4,5-Trifluorophenyl)Methyl]-Benzamide; 4-(Aminosulfonyl)-N-[(4-Fluorophenyl)Methyl]-Benzamide; 4-(Hydroxymercury) Benzoic Acid; 4-Fluorobenzenesulfonamide; 4-Methylimidazole; 4-Sulfonamide-[1-(4-Aminobutane)] Benzamide; 4-Sulfonamide-[4-(Thiomethylaminobutane)] Benzamide; 5-Acetamido-1,3,4-Thiadiazole-2-Sulfonamide; 6-Oxo-8,9,10,11-Tetrahydro-7h-Cyclohepta[C][1] Benzopyran-3-O-Sulfamate; (4-sulfamoyl-phenyl)-thiocarbamic acid O-(2-thiophen-3-yl-ethyl) ester; (R)-4-ethylamino-3,4-dihydro-2-(2-methoylethyl)-2H-thieno[3,2-E]-1,2-thiazine-6-sulfonamide-1,1-dioxide; 3,4-dihydro-4-hydroxy-2-(2-thienymethyl)-2H-thieno[3,2-E]-1,2-thiazine-6-sulfonamide-1,1-dioxide; 3,4-dihydro-4-hydroxy-2-(4-methoxyphenyl)-2H-thieno[3,2-E]-1,2-thiazine-6-sulfonamide-1,1-dioxide; N-[(4-methoxyphenyl)methyl]2,5-thiophenedesulfonamide; 2-(3-methoxyphenyl)-2H-thieno-[3,2-E]-1,2-thiazine-6-sulfinamide-1,1-dioxide; (R)-3,4-didhydro-2-(3-methoxyphenyl)-4-methylamino-2H-thieno[3,2-E]-1,2-thiazine-6-sulfonamide-1,1-dioxide; (S)-3,4-dihydro-2-(3-methoxyphenyl)-4-methylamino-2H-thieno[3,2-E]-1,2-thiazine-6-sulfonamide-1,1-dioxide; 3,4-dihydro-2-(3-methoxyphenyl)-2H-thieno-[3,2-E]-1,2-thiazine-6-sulfonamide-1,1-dioxide; [2h-Thieno[3,2-E]-1,2-Thiazine-6-Sulfonamide,2-(3-Hydroxyphenyl)-3-(4-Morpholinyl)-, 1,1-Dioxide]; [2h-Thieno[3,2-E]-1,2-Thiazine-6-Sulfonamide,2-(3-Methoxyphenyl)-3-(4-Morpholinyl)-, 1,1-Dioxide]; Aminodi(Ethyloxy) Ethylaminocarbonylbenzenesulfonamide; N-(2,3,4,5,6-Pentafluoro-Benzyl)-4-Sulfamoyl-Benzamide; N-(2,6-Difluoro-Benzyl)-4-Sulfamoyl-Benzamide; N-(2-FLOURO-BENZYL)-4-SULFAMOYL-BENZAMIDE; N-(2-

Thienylmethyl)-2,5-Thiophenedisulfonamide; N-[2-(1H-INDOL-5-YL)-BUTYL]-4-SULFAMOYL-BENZAMIDE; N-Benzyl-4-Sulfamoyl-Benzamide; or Sulfamic Acid 2,3-O-(1-Methylethylidene)-4,5-O-Sulfonyl-Beta-Fructopyranose Ester.

In yet additional embodiments, an agent in combination with a PDE agent may be a reported modulator of a catechol-O-methyltransferase (COMT), such as floproprione, or a COMT inhibitor, such as tolcapone (CAS RN 134308-13-7), nitecapone (CAS RN 116313-94-1), or entacapone(CAS RN 116314-67-1 or 130929-57-6).

In yet further embodiments, an agent in combination with a PDE agent may be a reported modulator of hedgehog pathway or signaling activity such as cyclopamine, jervine, ezetimibe, regadenoson (CAS RN 313348-27-5, or CVT-3146), a compound described in U.S. Pat. No. 6,683,192 or identified as described in U.S. Pat. No. 7,060,450, or CUR-61414 or another compound described in U.S. Pat. No. 6,552,016.

In other embodiments, an agent in combination with a PDE agent may be a reported modulator of IMPDH, such as mycophenolic acid or mycophenolate mofetil (CAS RN 128794-94-5).

In yet additional embodiments, an agent in combination with a PDE agent may be a reported modulator of a sigma receptor, including sigma-1 and sigma-2. Non-limiting examples of such a modulator include an agonist of sigma-1 and/or sigma-2 receptor, such as (+)-pentazocine, SKF 10,047 (N-allylnormetazocine), or 1,3-di-o-tolylguanidine (DTG). Additional non-limiting examples include SPD-473 (from Shire Pharmaceuticals); a molecule with sigma modulatory activity as known in the field (see e.g., Bowen et al., *Pharmaceutica* Acta Helvetiae 74: 211-218 (2000)); a guanidine derivative such as those described in U.S. Pat. Nos. 5,489,709; 6,147,063; 5,298,657; 6,087,346; 5,574,070; 5,502,255; 4,709,094; 5,478,863; 5,385,946; 5,312,840; or 5,093,525; WO9014067; an antipsychotic with activity at one or more sigma receptors, such as haloperidol, rimcazole, perphenazine, fluphenazine, (−)-butaclamol, acetophenazine, trifluoperazine, molindone, pimozide, thioridazine, chlorpromazine and triflupromazine, BMY 14802, BMY 13980, remoxipride, tiospirone, cinuperone (HR 375), or WY47384.

Additional non-limiting examples include igmesine; BD1008 and related compounds disclosed in U.S. Publication No. 20030171347; cis-isomers of U50488 and related compounds described in de Costa et al., *J. Med. Chem.*, 32(8): 1996-2002 (1989); U101958; SKF10,047; apomorphine; OPC-14523 and related compounds described in Oshiro et al., *J Med. Chem.*; 43(2): 177-89 (2000); arylcyclohexamines such as PCP; (+)-morphinans such as dextrallorphan; phenylpiperidines such as (+)-3-PPP and OHBQs; neurosteroids such as progesterone and desoxycorticosterone; butryophenones; BD614; or PRX-00023. Yet additional non-limiting examples include a compound described in U.S. Pat. Nos. 6,908,914; 6,872,716; 5,169,855; 5,561,135; 5,395,841; 4,929,734; 5,061,728; 5,731,307; 5,086,054; 5,158,947; 5,116,995; 5,149,817; 5,109,002; 5,162,341; 4,956,368; 4,831,031; or 4,957,916; U.S. Publication Nos. 20050132429; 20050107432; 20050038011, 20030105079; 20030171355; 20030212094; or 20040019060; European Patent Nos. EP 503 411; EP 362 001-A1; or EP 461 986; International Publication Nos. WO 92/14464; WO 93/09094; WO 92/22554; WO 95/15948; WO 92/18127; 91/06297; WO01/02380; WO91/18868; or WO 93/00313; or in Russell et al., *J Med. Chem.*; 35(11): 2025-33 (1992) or Chambers et al., *J. Med. Chem.*; 35(11): 2033-9 (1992).

Further non-limiting examples include a sigma-1 agonist, such as IPAG (i-(4-iodophenyl)-3-(2-adamantyl)guanidine); pre-084; carbetapentane; 4-IBP; L-687,384 and related compounds described in Middlemiss et al., *Br. J. Pharm.*, 102: 153 (1991); BD 737 and related compounds described in Bowen et al., *J Pharmacol Exp Ther.*, 262(1): 32-40 (1992)); OPC-14523 or a related compound described in Oshiro et al., *J Med. Chem.*; 43(2): 177-89 (2000); a sigma-1 selective agonist, such as igmesine; (+)-benzomorphans, such as (+)-pentazocine and (+)-ethylketocyclazocine; SA-4503 or a related compound described in U.S. Pat. No. 5,736,546 or by Matsuno et al., *Eur J. Pharmacol.*, 306(1-3): 271-9 (1996); SK&F 10047; or ifenprodil; a sigma-2 agonist, such as haloperidol, (+)-5,8-disubstituted morphan-7-ones, including CB 64D, CB 184, or a related compound described in Bowen et al., *Eur. J. Parmacol.* 278:257-260 (1995) or Bertha et al., *J. Med. Chem.* 38:4776-4785 (1995); or a sigma-2 selective agonist, such as i-(4-fluorophenyl)-3-[4-[3-(4-fluorophenyl)-8-azabicyclo[3.2.1]oct-2-en-8-yl]-1-butyl]-1H-indole, Lu 28-179, Lu 29-253 or a related compound disclosed in U.S. Pat. No. 5,665,725 or 6,844,352, U.S. Publication No. 20050171135, International Patent Publication Nos. WO 92/22554 or WO 99/24436, Moltzen et al., *J. Med. Chem.*, 26; 38(11): 2009-17 (1995) or Perregaard et al., *J Med. Chem.*, 26; 38(11): 1998-2008 (1995).

Alternative non-limiting examples include a sigma-1 antagonist such as BD-1047 (N(−)[2-(3,4-dichlorophenyl) ethyl]-N-methyl-2-(dimethylamin-o)ethylamine), BD-1063 (1 (−)[2-(3,4-dichlorophenyl)ethyl]-4-methylpiperazine, rimcazole, haloperidol, BD-1047, BD-1063, BMY 14802, DuP 734, NE-100, AC915, or R-(+)-3-PPP. Particular non-limiting examples include fluoxetine, fluvoxamine, citalopram, sertaline, clorgyline, imipramine, igmesine, opipramol, siramesine, SL 82.0715, imcazole, DuP 734, BMY 14802, SA 4503, OPC 14523, panamasine, or PRX-00023.

Other non-limiting examples of an agent in combination with a PDE agent include acamprosate (CAS RN 77337-76-9); a growth factor, like LIF, EGF, FGF, bFGF or VEGF as non-limiting examples; octreotide (CAS RN 83150-76-9); an NMDA modulator like ketamine, DTG, (+)-pentazocine, DHEA, Lu 28-179 (1'-[4-[1-(4-fluorophenyl)-1H-indol-3-yl]-1-butyl]-spiro[isobenzofuran-1(3H), 4'piperidine]), BD 1008 (CAS RN 138356-08-8), ACEA1021 (Licostinel or CAS RN 153504-81-5), GV150526A (Gavestinel or CAS RN 153436-22-7), sertraline, clorgyline, or memantine as non-limiting examples; or metformin.

Of course a further combination therapy may also be that of a PDE agent, optionally in combination with one or more other neurogenic agents, with a non-chemical based therapy. Non-limiting examples include the use of psychotherapy for the treatment of many conditions described herein, such as the psychiatric conditions, as well as behavior modification therapy such as that use in connection with a weight loss program.

Having now generally described the invention, the same will be more readily understood through reference to the following examples which are provided by way of illustration, and are not intended to be limiting of the disclosed invention, unless specified.

EXAMPLES

Example 1

Effect of Combining Captopril and Ibudilast on Neuronal Differentiation of Human Neural Stem Cells Human neural stem cells (hNSCs) were isolated and grown in monolayer culture, plated, treated with varying concentrations of captopril and/or ibudilast (test compounds), and stained with TUJ-1 antibody, as described in U.S. Provisional Application No. 60/697,905 (incorporated by reference). Mitogen-free test media with a positive control for neuronal differentiation was used along with basal media without growth factors as a negative control.

Results are shown in FIG. 1, which shows concentration response curves of neuronal differentiation after background media values are subtracted. The concentration response curve of the combination of captopril and ibudilast is shown with the concentration response curves of captropril or ibudilast alone. The data is presented as a percent of neuronal positive control. The data indicate that the combination of captopril and ibudilast resulted in superior promotion of neuronal differentiation than either agent alone.

Example 2

Effect of Combining Captopril and Enoximone on Neuronal Differentiation of Human Neural Stem Cells Human neural stem cells (hNSCs) were isolated and grown in monolayer culture, plated, treated with varying concentrations of captopril and/or enoximone (test compounds), and stained with TUJ-1 antibody, as described in U.S. Provisional Application No. 60/697,905 (incorporated by reference).

Results are shown in FIG. 2, which shows concentration response curves of neuronal differentiation after background media values are subtracted. The concentration response curve of the combination of captopril and enoximone is shown with the concentration response curves of captropril or enoximone alone. The data is presented as a percent of neuronal positive control. The data indicate that the combination of captopril and enoximone resulted in superior promotion of neuronal differentiation than either agent alone.

Example 3

Effect of Combining Serotonin and Enoximone on Neuronal Differentiation of Human Neural Stem Cells Human neural stem cells (hNSCs) were isolated and grown in monolayer culture, plated, treated with varying concentrations of serotonin and/or enoximone (test compounds), and stained with TUJ-1 antibody, as described in Example 2.

Results are shown in FIG. 3, which shows concentration response curves of neuronal differentiation after background media values are subtracted. The concentration response curve of the combination of serotonin and enoximone is shown with the concentration response curves of serotonin or enoximone alone. The data is presented as a percent of neuronal positive control. The data indicate that the combination of serotonin and enoximone resulted in superior promotion of neuronal differentiation than either agent alone.

Example 4

Effect of Combining Serotonin and Rolipram on Neuronal Differentiation of Human Neural Stem Cells Human neural stem cells (hNSCs) were isolated and grown in monolayer culture, plated, treated with varying concentrations of serotonin and/or rolipram (test compounds), and stained with TUJ-1 antibody, as described in Examples 2 and 3.

Results are shown in FIG. 4, which shows concentration response curves of neuronal differentiation after background media values are subtracted. The concentration response curve of the combination of serotonin and rolipram is shown with the concentration response curves of serotonin or rolipram alone. The data is presented as a percent of neuronal positive control. The data indicate that the combination of serotonin and rolipram resulted in superior promotion of neuronal differentiation than either agent alone.

Example 5

Effect of Combining Buspirone and Rolipram on Neuronal Differentiation of Human Neural Stem Cells Human neural stem cells (hNSCs) were isolated and grown in monolayer culture, plated, treated with varying concentrations of buspirone and/or rolipram (test compounds), and stained with TUJ-1 antibody, as described in Examples 2 to 4.

Results are shown in FIG. 5, which shows concentration response curves of neuronal differentiation after background media values are subtracted. The concentration response curve of the combination of buspirone and rolipram is shown with the concentration response curves of buspirone or rolipram alone. The data is presented as a percent of neuronal positive control. The data indicate that the combination of buspirone and rolipram resulted in superior promotion of neuronal differentiation than either agent alone.

Example 6

Effect of Combining Ibudilast and Candesartan on Neuronal Differentiation of Human Neural Stem Cells Human neural stem cells (hNSCs) were isolated and grown in monolayer culture, plated, treated with varying concentrations of ibudilast and/or candesartan (test compounds), and stained with TUJ-1 antibody, as described in Example 1.

Results are shown in FIG. 6, which shows concentration response curves of neuronal differentiation after background media values are subtracted. The concentration response curve of the combination of ibudilast and candesartan is shown with the concentration response curves of ibudilast or candesartan alone. The data is presented as a percent of neuronal positive control. The data indicate that the combination of ibudilast and candesartan resulted in superior promotion of neuronal differentiation than either agent alone.

Example 7

Determination of Synergy

The presence of synergy was determined by use of a combination index (CI). The CI based on the $EC_{50}$ as used to determine whether a pair of compounds had an additive, synergistic (greater than additive), or antagonistic effect when run in combination. The CI is a quantitative measure of the nature of drug interactions, comparing the $EC_{50}$'s of two compounds, when each is assayed alone, to the $EC_{50}$ of each compound when assayed in combination. The combination index (CI) is equal to the following formula:

$$\frac{C1}{IC1} + \frac{C2}{IC2} + \frac{(C1*C2)}{(IC1*IC2)}$$

where C1 and C2 are the concentrations of a first and a second compound, respectively, resulting in 50% activity in neuronal differentiation when assayed in combination; and IC1 and IC2 are the concentrations of each compound resulting in 50% activity when assayed independently. A CI of less than 1 indicates the presence of synergy; a CI equal to 1 indicates an additive effect; and a CI greater than 1 indicates antagonism between the two compounds.

Non-limiting examples of combinations of a PDE inhibitor and an additional agent as described herein were observed to result in synergistic activity. The exemplary results, based on FIGS. 1 to 6, are shown in the following table.

| Figure | Combo | CI |
|---|---|---|
| FIG. 1 | Ibudilast-Captopril | 0.05 |
| FIG. 2 | Captopril-Enoximone | 0.50 |
| FIG. 3 | Serotonin-Enoximone | 0.22 |
| FIG. 4 | Serotonin-Rolipram | 0.35 |
| FIG. 5 | Buspirone-Rolipram | 0.42 |
| FIG. 6 | Ibudilast-Candesartan | 0.18 |

As the CI is less than 1 for each of these combinations, the two compounds have a synergistic effect in neuronal differentiation.

The above is based on the selection of $EC_{50}$ as the point of comparison for the two compounds. The comparison is not limited by the point used, but rather the same comparison may be made at another point, such as $EC_{20}$, $EC_{30}$, $EC_{40}$, $EC_{60}$, $EC_{70}$, $EC_{80}$, or any other EC value above, below, or between any of those points.

All references cited herein, including patents, patent applications, and publications, are hereby incorporated by reference in their entireties, whether previously specifically incorporated or not.

Having now fully provided the instant disclosure, it will be appreciated by those skilled in the art that the same can be performed within a wide range of equivalent parameters, concentrations, and conditions without departing from the spirit and scope of the disclosure and without undue experimentation.

While the disclosure has been described in connection with specific embodiments thereof, it will be understood that it is capable of further modifications. This application is intended to cover any variations, uses, or adaptations of the disclosure following, in general, the disclosed principles and including such departures from the disclosure as come within known or customary practice within the art to which the disclosure pertains and as may be applied to the essential features hereinbefore set forth.

What is claimed is:

1. A composition comprising rolipram and buspirone in concentrations effective to produce a synergistic effect in neurogenesis.

2. The composition of claim 1, wherein said composition is in a pharmaceutically acceptable formulation.

* * * * *